US012305218B2

(12) United States Patent
Ouellet et al.

(10) Patent No.: US 12,305,218 B2
(45) Date of Patent: *May 20, 2025

(54) OPTIMIZATION OF IN VITRO ISOLATION OF NUCLEIC ACIDS USING SITE-SPECIFIC NUCLEASES

(71) Applicant: DEPIXUS, Paris (FR)

(72) Inventors: Jimmy Ouellet, Lardy (FR); Jerome Maluenda, Saint Michel S/orge (FR)

(73) Assignee: DEPIXUS, Paris (FR)

( * ) Notice: Subject to any disclaimer, the term of this patent is extended or adjusted under 35 U.S.C. 154(b) by 1069 days.

This patent is subject to a terminal disclaimer.

(21) Appl. No.: 17/282,683

(22) PCT Filed: Nov. 18, 2019

(86) PCT No.: PCT/EP2019/081625

§ 371 (c)(1),
(2) Date: Apr. 2, 2021

(87) PCT Pub. No.: WO2020/099675

PCT Pub. Date: May 22, 2020

(65) Prior Publication Data

US 2021/0388414 A1 Dec. 16, 2021

(30) Foreign Application Priority Data

Nov. 16, 2018 (EP) .................................... 18306507

(51) Int. Cl.
*C12Q 1/6806* (2018.01)
*C12N 9/22* (2006.01)

(52) U.S. Cl.
CPC ............. *C12Q 1/6806* (2013.01); *C12N 9/22* (2013.01)

(58) Field of Classification Search
CPC ............ C12Q 1/6806; C12Q 2521/101; C12Q 2521/301; C12Q 2521/319; C12N 9/22
See application file for complete search history.

(56) References Cited

U.S. PATENT DOCUMENTS

| | | | |
|---|---|---|---|
| 10,081,829 | B1 | 9/2018 | Shuber et al. |
| 2016/0208241 | A1 | 7/2016 | Tsai et al. |

FOREIGN PATENT DOCUMENTS

| | | | |
|---|---|---|---|
| WO | 2011147929 A1 | 12/2011 |
| WO | 2011147931 A1 | 12/2011 |
| WO | 2013093005 A1 | 6/2013 |
| WO | 2014114687 A1 | 7/2014 |
| WO | 2015071474 A2 | 5/2015 |
| WO | 2016100955 A2 | 6/2016 |
| WO | 2016177808 A1 | 11/2016 |
| WO | 2018231985 A1 | 12/2018 |
| WO | 2019030306 A1 | 2/2019 |

OTHER PUBLICATIONS

Slaymaker et al., Rationally engineered Cas9 nucleases with improved specificity, Science, 2015, 351(6268): 84-86.
Zetsche et al., Cpf1 Is a Single RNA-Guided Endonuclease of a Class 2 CRISPR-Cas System, Cell, 2015, 163(3): 759-771.
Gao et al., Engineered Cpf1 variants with altered PAM specificities increase genome targeting range, Nat Biotechnol. 2017, 35(8): 789-792.
Cromwell et al., Incorporation of bridged nucleic acids into CRISPR RNAs improves Cas9 endonuclease specificity, Nat Commun. 2018, 9(1): 1448.
Orden Rueda et al., Mapping the sugar dependency for rational generation of a DNA-RNA hybrid-guided Cas9 endonuclease, Nat Commun. 2017, 8:1610.
Karvelis et al., Rapid characterization of CRISPR-Cas9 protospacer adjacent motif sequence elements, Genome Biology, 2015, 16:253.
Pingoud and Jeltsch, Rapid characterization of CRISPR-Cas9 protospacer adjacent motif sequence elements, Nucleic Acids Res, 2001, 29(18): 3705-3727.
Zhang et al., Optimizing the specificity of nucleic acid hybridization, Nat Chem, 2012, 4(3): 208-214.
Strohkendl et al., Kinetic Basis for DNA Target Specificity of CRISPRCas12a, Molecular Cell, 2018, 71:1-9.
Gahan, Circulating nucleic acids in plasma and serum: applications in diagnostic techniques for noninvasive prenatal diagnosis, Int J Womens Health. 2013, 5: 177-186.
Ghorbian and Ardekani, Non-Invasive Detection of Esophageal Cancer using Genetic Changes in Circulating Cell-Free DNA, Avicenna J Med Biotech. 2012, 4(1): 3-13.
Wojno et al., Reduced Rate of Repeated Prostate Biopsies Observed in ConfirmMDx Clinical Utility Field Study, American health & drug benefits, 2014, 7(3): 129.
Thermoscientific, "T4 DNA Polymerase: product information," 2016.

*Primary Examiner* — Paul J Holland
(74) *Attorney, Agent, or Firm* — Arrigo, Lee, Guttman & Mouta-Bellum LLP

(57) ABSTRACT

The present invention relates to a method of preparing a nucleic acid molecule comprising a target region for isolation from a sample, said method comprising the steps of contacting a population of nucleic acid molecules with a first Class 2 Type V Cas protein-gRNA complex, wherein the gRNA comprises a guide segment that is complementary to a first sequence within a nucleic acid molecule, said first sequence being located adjacent to said target region, thereby forming a Class 2 Type V Cas protein-gRNA-nucleic acid complex, and a protector molecule, contacting the population of nucleic acid molecules with at least one enzyme having exonuclease activity, recovering said nucleic acid molecule comprising the target region from the Class 2 Type V Cas protein-gRNA-nucleic acid complex formed in step a), and contacting the nucleic acid molecule of step c) with a processive polymerase, preferably a mesophilic or thermophilic polymerase, even more preferably a T4 DNA polymerase.

20 Claims, 21 Drawing Sheets

Figure 1:
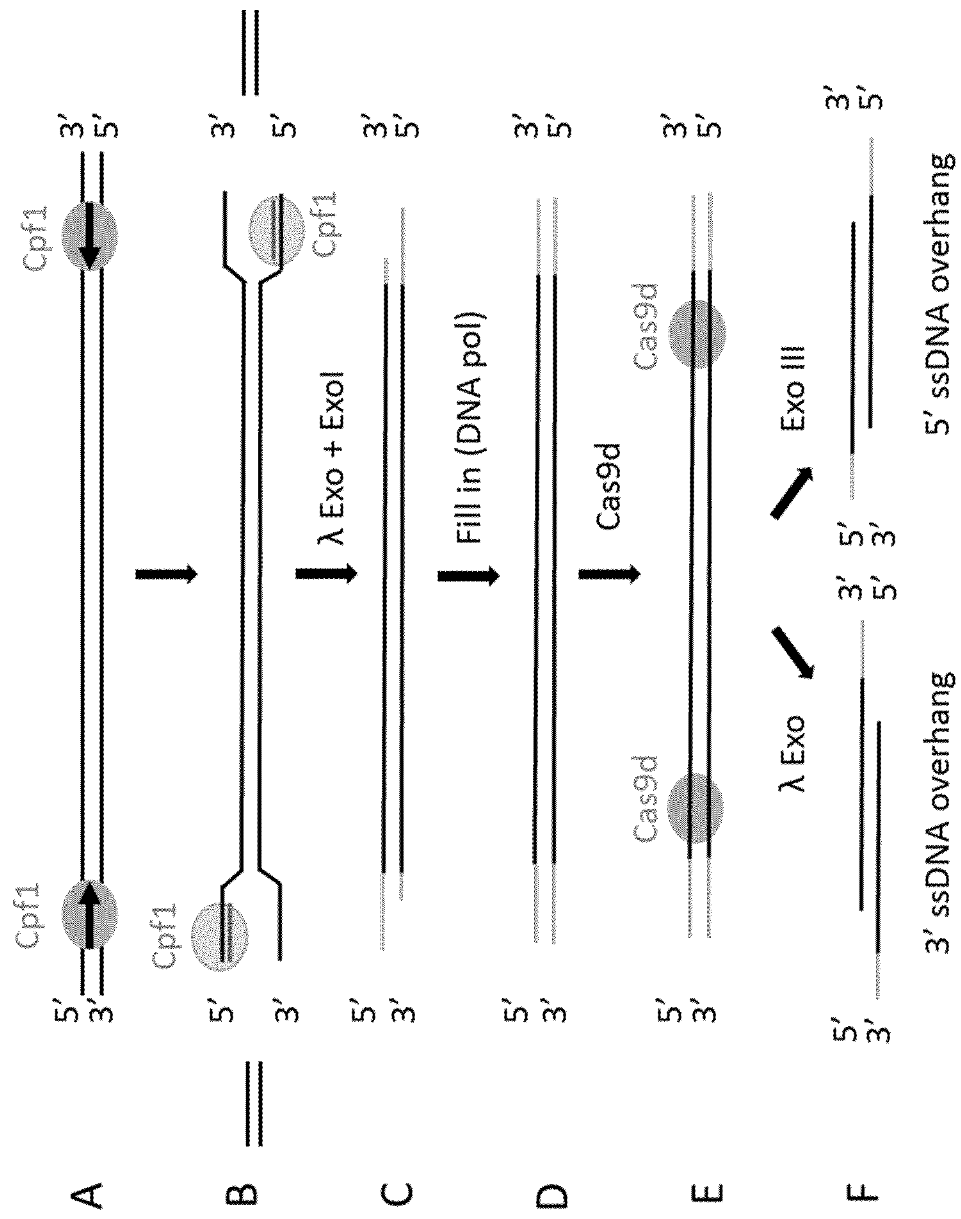

Specification includes a Sequence Listing.

| Site | Expected | Experimental | Distance | Hybridisation Rate | Hybridisation Time |
|---|---|---|---|---|---|
| CAAG | 4478 | 4482,4 | -4,4 | 0,1 | 2,08 |
| CAAG | 4355 | 4357,8 | -2,8 | 0,17 | 2,66 |
| CAAG | 4009 | 4007,1 | 1,9 | 0,15 | 2,64 |
| CAAG | 3954 | 3954,3 | -0,3 | 0,07 | 1,47 |
| CAAG[1] | 3798 | - | - | - | - |
| CAAG[1] | 3792 | 3792,8 | -0,8 | 0,29 | 2,76 |
| CAAG | 2498 | 2492,2 | 5,8 | 0,35 | 2,57 |
| CAAG | 2390 | 2387,5 | 2,5 | 0,14 | 1,12 |
| CAAG[2] | | 2236,6 | | 0,07 | 2,89 |
| CAAG | 1927 | 1921,1 | 5,9 | 0,13 | 3,04 |
| CAAG[1] | 1311 | 1310,6 | 0,4 | 0,17 | 2,87 |
| CAAG[1] | 1302 | - | - | - | - |
| CAAG | 1034 | 1033,6 | 0,4 | 0,09 | 2,16 |
| CAAG | 732 | 731,5 | 0,5 | 0,12 | 2,01 |
| CAAG | 597 | 603,3 | -6,3 | 0,15 | 1,2 |
| CAAG | 351 | 353,8 | -2,8 | 0,22 | 3,22 |

| Site | Expected | Experimental | Distance | Hybridisation Rate | Hybridisation Time |
|---|---|---|---|---|---|
| CCWGG | 3026 | 3029 | -3,0 | 0,22 | 4,42 |
| CCWGG | 2991 | 2995 | -4,0 | 0,2 | 1,89 |
| CCWGG | 2796 | 2796,1 | -0,1 | 0,19 | 2,78 |
| CCWGG | 2514 | 2510,5 | 3,5 | 0,29 | 2,33 |
| CCWGG | 2248 | 2243,5 | 4,5 | 0,54 | 4,1 |
| CCWGG | 2226 | 2221,9 | 4,1 | 0,23 | 1,66 |
| CCWGG | 1824 | 1825,9 | -1,9 | 0,05 | 0,69 |
| CCWGG | 976 | 979 | -3,0 | 0,07 | 2,44 |

| Site | Expected | Experimental | Distance | Hybridisation Rate | Hybridisation Time |
|---|---|---|---|---|---|
| CAAG | 1178 | 1177,8 | 0,2 | 0,08 | 0,39 |
| CAAG | 1067 | 1066 | 1,0 | 0,21 | 2 |
| CAAG | 1048 | 1049,5 | -1,5 | 0,15 | 0,48 |
| CAAG | 816 | 816,4 | -0,4 | 0,08 | 0,68 |
| CAAG | 563 | 562,9 | 0,1 | 0,07 | 0,29 |
| CAAG | 416 | 413,9 | 2,1 | 0,22 | 3,25 |
| CAAG | 333 | 333,4 | -0,4 | 0,07 | 0,4 |
| CAAG | 271 | 271,1 | -0,1 | 0,15 | 0,65 |
| CAAG | 208 | 209,1 | -1,1 | 0,41 | 1,34 |

| Site | Expected | Experimental | Distance | Hybridisation Rate | Hybridisation Time |
|---|---|---|---|---|---|
| CCWGG | 1237 | 1237,3 | -0,3 | 0,29 | 3,6 |
| CCWGG | 738 | 737,5 | 0,5 | 0,22 | 2,98 |
| CCWGG | 27 | 27,2 | -0,2 | 0,35 | 1,54 |

| Site | Expected | Experimental | Distance | Hybridisation Rate | Hybridisation Time |
|---|---|---|---|---|---|
| CAAG | 1300 | 1300,9 | -0,9 | 0,12 | 3,89 |
| CAAG | 1123 | 1124,5 | -1,5 | 0,04 | 1,12 |
| CAAG[1] | 897 | - | - | - | - |
| CAAG[1] | 888 | 885,3 | 2,7 | 0,22 | 1,15 |
| CAAG | 435 | 430,9 | 4,1 | 0,23 | 3,7 |
| CAAG | 359 | 357,2 | 1,8 | 0,16 | 0,47 |
| CAAG | 333 | 338 | -5,0 | 0,11 | 1,06 |
| CAAG | 320 | 320 | 0,0 | 0,2 | 0,96 |
| CAAG | 177 | 178,2 | -1,2 | 0,43 | 2,72 |

| Site | Expected | Experimental | Distance | Hybridisation Rate | Hybridisation Time |
|---|---|---|---|---|---|
| CCWGG | 1211 | 1210,1 | 0,9 | 0,07 | 0,44 |
| CCWGG | 1187 | 1188,9 | -1,9 | 0,1 | 0,97 |
| CCWGG | 1090 | 1089,7 | 0,3 | 0,18 | 1,38 |
| CCWGG | 585 | 583,7 | 1,3 | 0,22 | 1,7 |
| CCWGG | 119 | 117,7 | 1,3 | 0,34 | 2,69 |
| CCWGG | 50 | 51,9 | -1,9 | 0,14 | 4,66 |

| Site | Expected | Experimental | Distance | Hybridisation Rate | Hybridisation Time |
|---|---|---|---|---|---|
| CAAG | 684 | 684,2 | -0,2 | 0,17 | 1,08 |
| CAAG | 571 | 570,8 | 0,2 | 0,12 | 0,4 |
| CAAG | 417 | 416,8 | 0,2 | 0,1 | 0,5 |
| CAAG | 314 | 314,2 | -0,2 | 0,28 | 2,01 |

| Site | Expected | Experimental | Distance | Hybridisation Rate | Hybridisation Time |
|---|---|---|---|---|---|
| CCWGG | 481 | 480,5 | 0,5 | 0,04 | 0,36 |
| CCWGG | 445 | 445,6 | -0,6 | 0,05 | 0,31 |
| CCWGG | 334 | 333,9 | 0,1 | 0,06 | 0,45 |
| CCWGG | 326 | 325,9 | 0,1 | 0,07 | 0,55 |

| | Replicate | Starting DNA (μg) | Number of FOV | Number of HP | HP per FOV | HP per Flow cell | HP on Beads | Dilution Factor | Total HP | Efficacy Estimation | Fold Increase in Efficacy |
|---|---|---|---|---|---|---|---|---|---|---|---|
| Without End Repair | #1 | 2 | 10 | 1 | 0.1 | $8 \times 10^2$ | $4 \times 10^3$ | 0.25X | $1 \times 10^3$ | $2.6 \times 10^{-4}$% | N/A |
| | #2 | 2 | 20 | 12 | 0.6 | $4.8 \times 10^3$ | $2.4 \times 10^4$ | 0.05X | $1.2 \times 10^3$ | $3.1 \times 10^{-4}$% | N/A |
| With End Repair | #1 | 5 | 5 | 147 | 29.4 | $2.4 \times 10^5$ | $12 \times 10^5$ | 100X | $12 \times 10^7$ | 12.00% | 42000x |
| | #2 | 5 | 6 | 107 | 17.8 | $1.4 \times 10^5$ | $7 \times 10^5$ | 100X | $7 \times 10^7$ | 7.00% | 25000x |
| | #3 | 5 | 5 | 107 | 21.4 | $1.7 \times 10^5$ | $8.5 \times 10^5$ | 100X | $8.5 \times 10^7$ | 9.00% | 32000x |

Fig. 9

| Gene | Target | Disease | Chr | Start | End | Target Size |
|---|---|---|---|---|---|---|
| FMR1 | GCC-repeat | Fragile X syndrome | X | 147911033 | 147912743 | 1710 |
| C9orf72 | CpG+GGGGCC-repeat | amyotrophic lateral sclerosis | 9 | 27572678 | 27574118 | 1440 |
| SEPT9.1 | CpG | colorectal cancer | 17 | 77372516 | 77374810 | 2294 |
| SEPT9.2 | CpG | colorectal cancer | 17 | 77450851 | 77451948 | 1097 |
| CNRIP1 | CpG | colorectal cancer | 2 | 68319021 | 68320292 | 1271 |
| FBN1 | CpG | colorectal cancer | 15 | 48644393 | 48646658 | 2265 |
| INA | CpG | colorectal cancer | 10 | 103276677 | 103278492 | 1815 |
| MAL | CpG | colorectal cancer | 2 | 95024889 | 95026822 | 1933 |
| SNCA | CpG | colorectal cancer | 4 | 89836537 | 89837940 | 1403 |
| SPG20 | CpG | colorectal cancer | 13 | 36345467 | 36347222 | 1755 |
| HTT | CpG+CAG-repeat | huntington | 4 | 3073479 | 3075121 | 1642 |
| EGFR | CpG | lung cancer | 7 | 55018205 | 55020556 | 2351 |
| NDRG4.1 | CpG | myofibromatosis | 16 | 58462874 | 58465447 | 2573 |
| NDRG4.2 | CpG | myofibromatosis | 16 | 58500516 | 58501908 | 1392 |
| DMPK | CTG-repeat | Myotonic dystrophy | 19 | 45770028 | 45772277 | 2249 |

Fig. 10

| DNA Sample | [1]Starting Material (μg) | [2]Amount in Flowcell (%) | [3]Flowcell Analyzed | [4]Quantity Analyzed (μg) | [5]Molecules identified | | | | | | [6]Repeat Size (FMR1) | |
|---|---|---|---|---|---|---|---|---|---|---|---|---|
| | | | | | Total | Other | Sept9.1 | SEPT9.2 | C9orf72 | FMR1 | Allele 1 | Allele 2 |
| HEK | 10 | 10% | 100% | 1.000 | 26 | 0 | 5 | 5 | N/A | 16 | 31-35 | |
| NA06896 Replicate1 | 8.5 | 35% | 100% | 2.975 | 175 | 0 | 3 | 30 | 93 | 49 | 21-28 | 110-242 |
| NA06896 Replicate2 | 6.8 | 5% | 100% | 0.306 | 59 | 0 | 1 | 7 | 31 | 20 | 24-28 | 120-208 |
| NA07537 | 16 | 20% | 50% | 1.600 | 58 | 0 | 1 | 7 | 27 | 23 | 31 | 290-370 |

Fig. 13

| | | | | Methylated Molecules | | | | | |
|---|---|---|---|---|---|---|---|---|---|
| | | | | WT n=11 | | Pre-Mutated n=9 | | Full-Mutated n=3 | |
| Site Number | Position within HP | Sequence | Chr Position | Nb | Ratio | Nb | Ratio | Nb | Ratio |
| 1 | 276 | CG | 147911340 | 1 | 0.09 | 0 | 0.00 | 0 | 0.00 |
| 2 | 300 | CG | 147911364 | 3 | 0.27 | 3 | 0.33 | 0 | 0.00 |
| 3 | 306 | CG | 147911370 | 1 | 0.09 | 3 | 0.33 | 0 | 0.00 |
| 4 | 321 | CT | 147911385 | 0 | 0.00 | 1 | 0.11 | 0 | 0.00 |
| 5 | 326 | CG | 147911390 | 2 | 0.18 | 1 | 0.11 | 0 | 0.00 |
| 6 | 346 | CA | 147911410 | 0 | 0.00 | 1 | 0.11 | 0 | 0.00 |
| 7 | 388 | CT | 147911452 | 0 | 0.00 | 2 | 0.22 | 0 | 0.00 |
| 8 | 397 | CA | 147911461 | 0 | 0.00 | 2 | 0.22 | 0 | 0.00 |
| 9 | 409 | CG | 147911473 | 3 | 0.27 | 2 | 0.22 | 1 | 0.33 |
| 10 | 428 | CG | 147911492 | 5 | 0.45 | 2 | 0.22 | 0 | 0.00 |
| 11 | 440 | CT | 147911504 | 0 | 0.00 | 1 | 0.11 | 0 | 0.00 |
| 12 | 443 | CG | 147911507 | 3 | 0.27 | 2 | 0.22 | 0 | 0.00 |
| 13 | 448 | CT | 147911512 | 0 | 0.00 | 1 | 0.11 | 0 | 0.00 |
| 14 | 456 | CG | 147911520 | 4 | 0.36 | 3 | 0.33 | 0 | 0.00 |
| 15 | 510 | CG | 147911574 | 4 | 0.36 | 4 | 0.44 | 0 | 0.00 |
| 16 | 512 | CG | 147911576 | 4 | 0.36 | 4 | 0.44 | 0 | 0.00 |
| 17 | 529 | CG | 147911593 | 3 | 0.27 | 2 | 0.22 | 1 | 0.33 |
| 18 | 543 | CG | 147911607 | 3 | 0.27 | 2 | 0.22 | 0 | 0.00 |
| 19 | 563 | CG | 147911627 | 6 | 0.55 | 2 | 0.22 | 0 | 0.00 |
| 20 | 593 | CG | 147911657 | 6 | 0.55 | 3 | 0.33 | 0 | 0.00 |
| 21 | 605 | CG | 147911669 | 5 | 0.45 | 2 | 0.22 | 0 | 0.00 |
| 22 | 607 | CG | 147911671 | 5 | 0.45 | 2 | 0.22 | 0 | 0.00 |
| 23 | 617 | CG | 147911681 | 4 | 0.36 | 3 | 0.33 | 0 | 0.00 |
| 24 | 625 | CA | 147911689 | 1 | 0.09 | 1 | 0.11 | 0 | 0.00 |
| 25 | 628 | CG | 147911692 | 5 | 0.45 | 5 | 0.56 | 0 | 0.00 |
| 26 | 639 | CT | 147911703 | 0 | 0.00 | 1 | 0.11 | 0 | 0.00 |
| 27 | 644 | CG | 147911708 | 5 | 0.45 | 4 | 0.44 | 0 | 0.00 |
| 28 | 660 | CG | 147911724 | 4 | 0.36 | 3 | 0.33 | 0 | 0.00 |
| 29 | 662 | CG | 147911726 | 3 | 0.27 | 3 | 0.33 | 0 | 0.00 |
| 30 | 666 | CG | 147911730 | 4 | 0.36 | 2 | 0.22 | 0 | 0.00 |
| 31 | 670 | CG | 147911734 | 2 | 0.18 | 3 | 0.33 | 0 | 0.00 |
| 32 | 675 | CG | 147911739 | 4 | 0.36 | 3 | 0.33 | 0 | 0.00 |
| 33 | 677 | CG | 147911741 | 4 | 0.36 | 3 | 0.33 | 0 | 0.00 |
| 34 | 679 | CG | 147911743 | 4 | 0.36 | 3 | 0.33 | 0 | 0.00 |
| 35 | 690 | CG | 147911754 | 5 | 0.45 | 2 | 0.22 | 0 | 0.00 |
| 36 | 695 | CG | 147911759 | 2 | 0.18 | 2 | 0.22 | 0 | 0.00 |
| 37 | 703 | CG | 147911767 | 4 | 0.36 | 2 | 0.22 | 0 | 0.00 |
| 38 | 707 | CG | 147911771 | 3 | 0.27 | 3 | 0.33 | 0 | 0.00 |
| 39 | 714 | CA | 147911778 | 1 | 0.09 | 2 | 0.22 | 0 | 0.00 |
| 40 | 720 | CG | 147911784 | 2 | 0.18 | 2 | 0.22 | 0 | 0.00 |
| 41 | 722 | CG | 147911786 | 1 | 0.09 | 2 | 0.22 | 0 | 0.00 |
| 42 | 728 | CG | 147911792 | 2 | 0.18 | 2 | 0.22 | 0 | 0.00 |
| 43 | 730 | CG | 147911794 | 2 | 0.18 | 0 | 0.00 | 0 | 0.00 |
| 44 | 732 | CG | 147911796 | 2 | 0.18 | 1 | 0.11 | 0 | 0.00 |
| 45 | 746 | CA | 147911810 | 0 | 0.00 | 3 | 0.33 | 0 | 0.00 |

Fig. 15

| | | | | Methylated Molecules | | | | | |
|---|---|---|---|---|---|---|---|---|---|
| | | | | WT n=11 | | Pre-Mutated n=9 | | Full-Mutated n=3 | |
| Site Number | Position within HP | Sequence | Chr Position | Nb | Ratio | Nb | Ratio | Nb | Ratio |
| 46 | 750 | CT | 147911814 | 5 | 0.45 | 1 | 0.11 | 0 | 0.00 |
| 47 | 760 | CG | 147911824 | 5 | 0.45 | 4 | 0.44 | 0 | 0.00 |
| 48 | 766 | CG | 147911830 | 5 | 0.45 | 5 | 0.56 | 0 | 0.00 |
| 49 | 780 | CG | 147911844 | 3 | 0.27 | 3 | 0.33 | 0 | 0.00 |
| 50 | 782 | CG | 147911846 | 3 | 0.27 | 3 | 0.33 | 0 | 0.00 |
| 51 | 798 | CG | 147911862 | 3 | 0.27 | 4 | 0.44 | 0 | 0.00 |
| 52 | 807 | CG | 147911871 | 3 | 0.27 | 2 | 0.22 | 2 | 0.67 |
| 53 | 812 | CG | 147911876 | 4 | 0.36 | 2 | 0.22 | 2 | 0.67 |
| 54 | 815 | CA | 147911879 | 1 | 0.09 | 1 | 0.11 | 0 | 0.00 |
| 55 | 820 | CA | 147911884 | 3 | 0.27 | 2 | 0.22 | 0 | 0.00 |
| 56 | 829 | CA | 147911893 | 4 | 0.36 | 3 | 0.33 | 0 | 0.00 |
| 57 | 833 | CG | 147911897 | 3 | 0.27 | 2 | 0.22 | 0 | 0.00 |
| 58 | 838 | CG | 147911902 | 4 | 0.36 | 3 | 0.33 | 0 | 0.00 |
| 59 | 843 | CG | 147911907 | 3 | 0.27 | 4 | 0.44 | 0 | 0.00 |
| 60 | 851 | CG | 147911915 | 4 | 0.36 | 4 | 0.44 | 0 | 0.00 |
| 61 | 856 | CA | 147911920 | 2 | 0.18 | 4 | 0.44 | 0 | 0.00 |
| 62 | 865 | CG | 147911929 | 3 | 0.27 | 5 | 0.56 | 0 | 0.00 |
| 63 | 875 | CG | 147911939 | 6 | 0.55 | 6 | 0.67 | 0 | 0.00 |
| 64 | 880 | CG | 147911944 | 5 | 0.45 | 6 | 0.67 | 0 | 0.00 |
| 65 | 892 | CG | 147911956 | 4 | 0.36 | 5 | 0.56 | 0 | 0.00 |
| 66 | 899 | CT | 147911963 | 0 | 0.00 | 4 | 0.44 | 0 | 0.00 |
| 67 | 903 | CG | 147911967 | 4 | 0.36 | 5 | 0.56 | 0 | 0.00 |
| 68 | 913 | CG | 147911977 | 5 | 0.45 | 7 | 0.78 | 0 | 0.00 |
| 69 | 917 | CG | 147911981 | 4 | 0.36 | 4 | 0.44 | 0 | 0.00 |
| 70 | 920 | CG | 147911984 | 3 | 0.27 | 2 | 0.22 | 0 | 0.00 |
| 71 | 925 | CG | 147911989 | 4 | 0.36 | 5 | 0.56 | 0 | 0.00 |
| 72 | 928 | CG | 147911992 | 4 | 0.36 | 5 | 0.56 | 0 | 0.00 |
| 73 | 931 | CG | 147911995 | 5 | 0.45 | 3 | 0.33 | 0 | 0.00 |
| 74 | 935 | CG | 147911999 | 1 | 0.09 | 5 | 0.56 | 0 | 0.00 |
| 75 | 937 | CG | 147912001 | 0 | 0.00 | 2 | 0.22 | 0 | 0.00 |
| 76 | 941 | CG | 147912005 | 3 | 0.27 | 4 | 0.44 | 0 | 0.00 |
| 77 | 944 | CG | 147912008 | 3 | 0.27 | 3 | 0.33 | 0 | 0.00 |
| 78 | 947 | CG | 147912011 | 3 | 0.27 | 3 | 0.33 | 0 | 0.00 |
| 79 | 953 | CG | 147912017 | 4 | 0.36 | 5 | 0.56 | 0 | 0.00 |
| 80 | 957 | CT | 147912021 | 2 | 0.18 | 1 | 0.11 | 0 | 0.00 |
| 81 | 959 | CG | 147912023 | 4 | 0.36 | 3 | 0.33 | 0 | 0.00 |
| 82 | 962 | CG | 147912026 | 3 | 0.27 | 5 | 0.56 | 0 | 0.00 |
| 83 | 963 | CT | 147912027 | 3 | 0.27 | 2 | 0.22 | 0 | 0.00 |
| 84 | 968 | CA | 147912032 | 3 | 0.27 | 3 | 0.33 | 0 | 0.00 |
| 85 | 975 | CG | 147912039 | 4 | 0.36 | 3 | 0.33 | 0 | 0.00 |
| 86 | 979 | CG | 147912043 | 3 | 0.27 | 5 | 0.56 | 0 | 0.00 |
| 87 | 985 | CG | 147912049 | 4 | 0.36 | 5 | 0.56 | 0 | 0.00 |

Fig. 15 (cont.)

SEQUENCE LISTING

```
<160> NUMBER OF SEQ ID NOS: 160

<210> SEQ ID NO 1
<211> LENGTH: 44
<212> TYPE: RNA
<213> ORGANISM: Artificial
<220> FEATURE:
<223> OTHER INFORMATION: Generic single guide RNA for Cpf1
<220> FEATURE:
<221> NAME/KEY: misc_feature
<222> LOCATION: (21)..(44)
<223> OTHER INFORMATION: n is a, c, g, or u

<400> SEQUENCE: 1

uaauuucuac ucuuguagau nnnnnnnnnn nnnnnnnnnn nnnn                    44


<210> SEQ ID NO 2
<211> LENGTH: 42
<212> TYPE: RNA
<213> ORGANISM: Artificial
<220> FEATURE:
<223> OTHER INFORMATION: Generic crRNA sequence for Cas9
<220> FEATURE:
<221> NAME/KEY: misc_feature
<222> LOCATION: (1)..(20)
<223> OTHER INFORMATION: n is a, c, g, or u

<400> SEQUENCE: 2

nnnnnnnnnn nnnnnnnnnn guuuuagagc uaugcuguuu ug                      42


<210> SEQ ID NO 3
<211> LENGTH: 89
<212> TYPE: RNA
<213> ORGANISM: Artificial
<220> FEATURE:
<223> OTHER INFORMATION: Generic tracrRNA sequence for Cas9

<400> SEQUENCE: 3

guuggaacca uucaaaacag cauagcaagu uaaaauaagg cuaguccguu aucaacuuga    60

aaaaguggca ccgagucggu gcuuuuuuu                                      89
```

<210> SEQ ID NO 4
<211> LENGTH: 94
<212> TYPE: RNA
<213> ORGANISM: Artificial
<220> FEATURE:
<223> OTHER INFORMATION: Generic single guide RNA for Cas9
<220> FEATURE:
<221> NAME/KEY: misc_feature
<222> LOCATION: (1)..(20)
<223> OTHER INFORMATION: n is a, c, g, or u

<400> SEQUENCE: 4

```
nnnnnnnnnn nnnnnnnnnn guuuuagagc uagaaaguua aaauaaggcu aguccguuau     60

caacuugaaa aaguggcacc gagucggugc uuuu                                 94
```

<210> SEQ ID NO 5
<211> LENGTH: 2161
<212> TYPE: DNA
<213> ORGANISM: Homo sapiens

<400> SEQUENCE: 5

```
agaggtcgtg gcactgagat gggtctggca gatcccagcg tccaggccca gcccctatag     60

tgtcagctcc ctcctctggg gacccccttg cttgtgcccc tctgggtccc agcacatccc    120

aggcctgcag ggagggggag aggaagagac tgactcactg gccaggtccc ccaggggctg    180

gagaggctgg agaggcagga gctggatcag atctgaatcc agaggctctc ggaggaagag    240

ctcagggtga gctgcgcccc catcccctgc ccctcctctc ctgctccttc tcccttccat    300

ggtcccagcc agcaagcacc tggggtagag gggacaaacc caggtggctg tgttccagcc    360

ctggctgcag gtctgaatgg ctttctgggg tggctggcca tgctccctga gagcccagct    420

gtggcgatgt ctgagcaggt aggtggggga gcacctagga agcaggggtg tcaggcagag    480

cacaaggaga gagggtgtcc aggtcagttt caggacctgg ctgagaggag gggctcctc     540

acgggcaccg cctctggcaa gcacagggac aagggcaagg acggcatggc cagaggtccc    600

tgggagcctc ttcccctctc ttcttcctag cagctccccc tcactcttcc cagggacct     660

gtcactttcc tttagcgtgt ggcagctcct tggcgtccct cccgtgcctt caggttgctt    720

ctgcgccggg cctgccgctg ggcgccccta tctctgcctg ccccctcctc ctgctcccct    780

cgccctgccc ccttggagca attccccacc gagcctccct tcccaggcag tcgaggtccc    840

tccctacctc tgccccgcgc tctgggaggc tccttgttcc gcgaccacaa agcccctttg    900

atcctctgct cggctctgag ccatgtgacc cggtgggcgg gccgcggctc tcggcgcgtc    960

cagcgcagcc cgacgttccg ctgctggggt gagtcctgct cctttgttct tcccagcctt   1020

gcaccactgg ctcgggggct ctcaggtggc gcggccgcga ggcggaccct gatggccatg   1080

gtggcggtgc cgggagccac gctgtccctg ggccccggcc cgaggccggc aggaccgagc   1140

ggggtcccca ggagaggggt ggcggggagc tcgatctcca cgcggggacc agattttcgg   1200

cctcaaaata gaagaatagg gctttgtgtg gtcacagcta tctctttgta aatatttggc   1260

caactaagct gagtggctaa gttctcctgc tgcccggagc ttcttggaac atgtttcctt   1320

ttcgcaaggg gtttccctgg cttccaggag ggccaggaag aaattcgaat tggccaccgc   1380

tttctctaaa atcactccgc tcaagttatc acccctctgg gctcccgaag accggctggc   1440

tggaggctgg agatagtctc aatgctcgaa atgccgtaac cgaagctccc cgcggcgccg   1500

gcactgggat ccagggagct gctgctacag cgcagctctg gattcctgga tgtgttggat   1560

atgtgcaggg cgttcctggg aggagcgggg agggagggtg ctgctggcgg ggctggtctg   1620
```

```
cgtgtgcttt gcttctctac aatggcatgc tgcgtgtcgg ccatgcagag gcatgtcagt   1680

gagcaggggc tgagggatct ccctaacgga cctgctttca gagggtcttt tcatgctggg   1740

agaaccccag agactaaatc atgcagccaa cggggtggtc cccggcctca aagcagggag   1800

gggcgaggag ctttgtaggc aatgccatct gctcctgaaa cgccgtccca gtgactctgg   1860

ggactgactc agcctccagc ctgctgcact tcatccctgg cccctctctc tttgcttttt   1920

catgtgaaat ctgctgtgtt ttggtcagag gtttggggaa cagctctctg ctcatctaag   1980

ataagtttgt aattcctttc ctggagaaaa atatgccacc cggaagcagg ttgagcagtg   2040

gttttctggc aggtctgttc ggggctgtgg agacagcacc tgctggatca ggatggagtt   2100

ggaatttggt ttggatccca catgagaaaa cccgttggaa gaggaggaag cagaaaaagg   2160

c                                                                  2161


<210> SEQ ID NO 6
<211> LENGTH: 20
<212> TYPE: DNA
<213> ORGANISM: Artificial
<220> FEATURE:
<223> OTHER INFORMATION: Oligonucleotide for PCR amplification PS1131
      (Fwd SEPT9.2)

<400> SEQUENCE: 6

agaggtcgtg gcactgagat                                                20


<210> SEQ ID NO 7
<211> LENGTH: 20
<212> TYPE: DNA
<213> ORGANISM: Artificial
<220> FEATURE:
<223> OTHER INFORMATION: Oligonucleotide for PCR amplification PS1132
      (Rev SEPT9.2)

<400> SEQUENCE: 7

gccttttct gcttcctcct                                                 20


<210> SEQ ID NO 8
<211> LENGTH: 24
<212> TYPE: RNA
<213> ORGANISM: Artificial
<220> FEATURE:
<223> OTHER INFORMATION: Target specific sequence of the Cpf1-SEPT9.2-
      crRNA#1

<400> SEQUENCE: 8

uccccucuac cccaggugcu ugcu                                           24


<210> SEQ ID NO 9
<211> LENGTH: 24
<212> TYPE: RNA
<213> ORGANISM: Artificial
<220> FEATURE:
<223> OTHER INFORMATION: Target specific sequence of the Cpf1-SEPT9.2-
      crRNA#2

<400> SEQUENCE: 9

ucuaaaauca cuccgcucaa guua                                           24


<210> SEQ ID NO 10
<211> LENGTH: 20
<212> TYPE: RNA
<213> ORGANISM: Artificial
<220> FEATURE:
```

```
<223> OTHER INFORMATION: Target specific sequence of the Cas9-SEPT9.2-
      crRNA#1

<400> SEQUENCE: 10

ggcaaggacg gcauggccag                                                  20


<210> SEQ ID NO 11
<211> LENGTH: 20
<212> TYPE: RNA
<213> ORGANISM: Artificial
<220> FEATURE:
<223> OTHER INFORMATION: Target specific sequence of the Cas9-SEPT9.2-
      crRNA#2

<400> SEQUENCE: 11

aaacauguuc caagaagcuc                                                  20


<210> SEQ ID NO 12
<211> LENGTH: 5225
<212> TYPE: DNA
<213> ORGANISM: Escherichia coli

<400> SEQUENCE: 12

cagacggtaa ttgttcacct tcgccaaatt cacgacggcg gatcatctgt tccagctctt      60

cttccaccat ttcggagagt tttttacgcg ccagcgggcg gctacgcaag ttgcgaccaa     120

ttgcaggtga agaatcttcg gtttgcgaat caaatgcgtt cataaggccc attctgtaag     180

gtcagtgtga ttaacatcat cagtgacatc ctatcacagg attgaaagta ggggaaaatg     240

gcagggtttt ctctttgtgc ctcatcatta ccataattaa cggaataatt aactattgcg     300

aaaaattaat gtaacgcaga taaaaacatc ccgtttgaat tatttataag actattcacg     360

agcattatga atattatgaa tgtgttctta caaaataatc ataagcgcat attttttaat     420

gaaaaatcac ctcacctaca attaaaaaca cgacatccgc accataaata gccttgcaaa     480

aaatataaca tcgttgtttt caatctgccg tttatgggat tgaccgtttt cttttgacac     540

ggagttcaac aatgttcggc ataattatat ctgtcatcgt attaattacg atgggctatt     600

tgatcctgaa aaactacaaa cctcaggtgg tgctggctgc cgcaggtatc ttcctgatga     660

tgtgcggtgt ctggttaggg ttcggtggtg tactcgatcc caccaaaagc agcggctact     720

tgatcgtcga tatttataat gaaatcctgc gcatgctgtc caaccgcatt gccggattgg     780

ggctgtcgat tatggcggtg ggcggttatg cccgctacat ggagcgcata ggggccagtc     840

gcgcgatggt gagcttgtta agccgcccgt taaaactcat tcgctcgccg tatattattc     900

tgtcggcaac ttacgtcatc ggccaaatca tggcgcagtt tattaccagc gcctccggtc     960

tgggtatgtt gctgatggtc accttatttc cgacgctggt gagtctggga gtaagtcgtc    1020

tctctgcggt ggcagttatc gcaaccacga tgtccattga gtgggggatt ctggaaacga    1080

actccatttt tgctgcccag gtagcgggaa tgaaaattgc cacatacttc ttccactacc    1140

agcttccggt cgcctcttgc gtcattatct cggtggcgat ctcccacttt ttcgtgcaac    1200

gcgcttttga caaaaaagat aaaaatatca atcacgaaca ggcagagcaa aaagctctcg    1260

ataatgtccc gccgctctat tacgccattt tacctgtgat gccgttaatc ctgatgctcg    1320

gctcgctgtt cctcgcccac gtcgggctga tgcagtcaga actgcatctg gtggtggtga    1380

tgttactgag tttgactgtg acgatgtttg ttgagttctt ccgcaagcat aacttgcgcg    1440

aaacaatgga cgatgtgcag gcgttttttg acggcatggg tacgcagttt gccaacgtgg    1500

taacgctggt ggtcgcgggt gaaatatttg cgaaaggctt aacgacgatt ggcactgtcg    1560
```

```
atgcggttat caggggggcg gagcattctg gtctgggcgg tattggcgtg atgattatta   1620
tggcgctggt cattgccatt tgtgccattg tgatgggctc tggcaatgcg ccgtttatgt   1680
catttgccag tcttattccg aatatcgcag ccggactaca tgtaccagcg gttgtaatga   1740
ttatgccgat gcattttgcc acgacgctag cgcgcgcggt ttcgccgatt actgcggtgg   1800
tggtcgttac gtcaggaatt gcaggcgttt cgccttttgc ggtggtgaag cggacagcga   1860
tccccatggc agtcggtttc gtggtgaata tgattgccac aatcacgcta ttttattaag   1920
tcattaaaaa gacaaaacag gccgcctggg cctgttttgt attacttcac aacgcgtaat   1980
gccggtcgac caccgcgtgg tggctgcgga ggttcatcgt caggatgagt gtcatcatcg   2040
tgatctggct tgtcgccatc aataaccgac ataacggttt cgttgtctgc cgatgcctct   2100
tcatcattca tgatgctggt atcttcatcg taggcagctt caggctcaaa catcgtgcct   2160
gcgccatttt cacgggcgta gatagccagc acggcagcca gcggcacaga aacctgacgc   2220
ggaatgccac caaagcgcgc gttaaagcgc acctcatcat tcgccagttc cagattgccg   2280
acagcacgcg gcgcaatgtt gagtacgatt tgcccgtcac gcgcatattc cataggaacc   2340
tgcacgccag ggagcgtcac atccaccacc aggtgcggcg tgagctggtt atccagcaac   2400
cactcataga atgcacgcag cagataggga cgacgtggtg ttagctgtga caaatccata   2460
cagattaact ccggcccaga cgcatttcac gttctgcttc agttaaagaa gcaaggaaag   2520
agtcacgctc aaagacgcgg gtcatatagc ctttcagctc tttcgcaccc gggccgctga   2580
actcgatgcc cagttgcggc agacgccaca gcagcggagc aagatagcaa tcgaccaggc   2640
tgaactcatc gctcaggaag tacggcttct gaccgaagac cggcgcaatc gccagcagtt   2700
cttcgcgcag ttgcttacgt gcggcatctg cttcagaagc tgaaccgttg atgatggtgt   2760
tcatcagcgt gtaccagtct ttttcgatgc gatgcatgta cagacggctt tcaccgcgag   2820
ctaccgggta aacaggcatc agtggcggat gcgggaaacg ctcatccaga tattccataa   2880
tgatgcgaga ttcccacagg gtcagctcac gatccaccag ggtcggaacg ctctgattcg   2940
ggttgaggtc aatcagatcc tgaggcggat tgtccttttc cacgtgttcg atctcgaaac   3000
ttacaccttt ctcagccagc acaatgcgga cctgatggct atagatgtca gtaggaccgg   3060
aaaacagcgt cattaccgaa cgtttgttgg cagcgacagc catgaaaacc tccaggtata   3120
gtcagaattt ttactgctac cagccaccag gtggccagtc agaagttgtg ttacccaata   3180
aggaacgact ctctttgttc gaaaatcaaa caaaaaatga gcaatacccg acatttgggc   3240
agaaaattgg atgatagttt accagatttt gcgaccattg tggtgagtcg atgccggaaa   3300
tggggaaaaa gagatgcgct ttagtctgaa atagttgact tagtccctta ttggcgatgt   3360
ggtttttgtt ttacctgtct gtcaggtggc agcaaaaagc aactttccag tttttacgct   3420
gattcagatt ttagctataa aaaaacccgc cgaagcgggt tttttcgaaa attgttttct   3480
gccggagcag aagccaatta acgtttggag aactgcggac gacgacgtgc tttacgcaga   3540
ccgactttct tacgttcaac ctgacgagcg tcacgagtaa cgaagccagc tttacgcagt   3600
tcagaacgca gggactcgtc gtattccatc agagcgcggg tgataccgtg acggatcgca   3660
ccagcctgac cagagatacc accaccttta acggtgatgt acaggtccag tttctcaacc   3720
atgtcgacca gttccagcgg ctgacgaact accatgcggg cagtttcacg accgaagtac   3780
tgttccagag aacgttggtt gattacgatt ttaccgttgc ccggtttgat gaaaacgcga   3840
gctgcggaac ttttgcggcg accagtgccg tagtattgat tttcagccat tgcctataat   3900
```

```
cccgattaga tgtcaagaac ttgcggttgc tgtgccgcgt ggttgtgctc gttacccgcg   3960

taaactttca gtttacggaa catagcacga cccagcgggc cttttggcaa catgccttta   4020

accgcgattt caatcacacg ctcaggacgg cgagcaatca tctcttcaaa ggtcgcttgt   4080

ttgataccac cgatgtggcc ggtgtggtga tagtacactt tgtcagtacg cttgttgccg   4140

gttacagcaa ctttgtcagc gttcagaacg atgatgtaat caccggtatc tacgtgcgga   4200

gtgtattccg ctttgtgctt accgcgcagg cgacgagcca gttcagtagc cagacggccc   4260

agagttttac cggtcgcgtc aacaacatac cagtcgcgtt ttacggtttc tggtttagct   4320

gtaaaagttt tcattaaaag cttacccaat aaatagttac acgttggtga acacccaaac   4380

gtcttcaatt gttgaggttc acacgacaaa gtccggcaaa cctacccctt cgaatagcct   4440

atgccagcac acaaaaagtt ttgggaaaaa aactttcttg taacgtgggg tcgcaggatt   4500

atagagaagt cggggtcaaa gatcgacccc tttttgtgat ttgtgacagg ttttaacccg   4560

ccaaatgctc gcgcttcaga tactcttcgc tttgcatctc ttgcagacgt gacaggcaac   4620

gctggaactc aaacttcagc cgatcgccct gataaatttc atacagcggc acttctgcac   4680

tcaccactaa tttgacatgg cgctcgtaaa actcatccac cagcgcaata aagcgccgcg   4740

cttcgctctc catcaaccgc gtcataactg gtacatcaaa caacatgacc gtatgaaaga   4800

gacgtgagag cgcaatatag tcatgctgac tgcgggcgtc gacgcacagc gtagtaaaag   4860

agaccgccag cgtctggttc tcgacgccca ttgttgctaa tggccgatgg ttgatttcta   4920

acgtcggtga attttctcgt ttcccccccg ccagcgccaa ccatagttta tccatttgcg   4980

cccgggtttc atcgtgaagt ggcgaaagcc acagatgcgc ctgagtgagt gtacgcagac   5040

gataatcaac accagcgtcc acgttcatta catcacaatg ctgtttaatg gcatcgattg   5100

caggcagaaa acgcgcacgt tgcaggccat ttcgataaag ttcatccggc ggaatatttg   5160

acgtcgctac cagggtaata ccgcgagcga acagggcttt catcagaccg ccaagtagca   5220

tggca                                                               5225
```

```
<210> SEQ ID NO 13
<211> LENGTH: 24
<212> TYPE: RNA
<213> ORGANISM: Artificial
<220> FEATURE:
<223> OTHER INFORMATION: Target specific sequence of the Cpf1-Ecoli#1-
      crRNA#1 (Target#1)

<400> SEQUENCE: 13

gcgaaggnga acaauuaccg ucug                                            24
```

```
<210> SEQ ID NO 14
<211> LENGTH: 24
<212> TYPE: RNA
<213> ORGANISM: Artificial
<220> FEATURE:
<223> OTHER INFORMATION: Target specific sequence of the Cpf1-Ecoli#1-
      crRNA#2 (Target#1)

<400> SEQUENCE: 14

aucagaccgc caaguagcau ggca                                            24
```

```
<210> SEQ ID NO 15
<211> LENGTH: 1643
<212> TYPE: DNA
<213> ORGANISM: Escherichia coli

<400> SEQUENCE: 15
```

```
ttgctaaaga catacgggtt ctccgaaaat taatatttcc aaatttatca agtgcttaaa     60

taattaaatc tgtgctaaaa accaggtaag gatcagtagg tcagcactgc cgcctggact    120

gagatttcgt tcgatacact ccctgtcgaa ctgccggaga taatcgagat cggcgggggt    180

tcgaatgccc ccttttgca ataatgtttg cgcctcgcgc tgtagccagc gcaggccccc    240

ctcgccaccg cgcgatgcaa cgttggtatc gccgttgatc gccatcagta ggagcaaggt    300

atcgagcaat gccagttcag gatctaaccc ctgatccagc agagtgaggt aatgcggcaa    360

ggcgtgattg atcaccagtg gataacccgc ttcggcttca ccgcgtgcgc cggtaaggcc    420

aagctgttgg tacaaccgtt gacctgccgt cagttgtgaa ttattggtac gcagttcgcg    480

atcggtcagg ccacggcaga aacttgccgc cgtagaacaa acggttgttg gcgttaccgg    540

ttggttgagt tgaagcaaac ggccaattgc cgcacatagc agccctaaag aaaaaatgct    600

gcctttatgc gtgtttacgc ccgcagtggc gcggaacata tcaccttcgc aagccatacc    660

aattgggcgt aatccgtgga gtaccgcttc tggtgccatt tccgcactac aggcaccaaa    720

ttcaatgaaa cggggtagcc agccctgaat cgccagcgcg ctgcggtgga aatcttccag    780

cgccatatct ttgtgcgcac cgcagttaat gcgatccacg aggcctggtt tcggtgacag    840

attgacttca gtcagcatgg cgcgccagcc cagcagggcg tactcatcga ttaatgacgt    900

cgcaagcttt gtggttttag ttgacgttgc aggcatcgac atcgttcagc agtgcctcca    960

tgcggttgag taaatcggtc agttgatggg tttttccacg cgcgcagacg gctgcgcttt   1020

gttcgcacaa caggcagcgg cgaggcggca gtgaatagtc gcggcgggag agaatttcgc   1080

cttcgggcgt caggacatcg atatcccata accgcccgag aggatgacta tgttcaagct   1140

caatggtggc gagcttgagg tcgcgagccg gggcggcaat gctcaacatg ccctccggcc   1200

cgctggcgga aaccagtgca gcctgctcct gaatttgcca gccctgtttt gcggctaagg   1260

cacgcaaggc tgtcacgcca tgattaaaaa ttcggcgtgt gacctcgctg tctttaatcg   1320

gcccaggcgc aaccacggta aaggagacca gtggaacagg atggcgcttg agccagacgt   1380

gttgccgtgc ttgcctttca tcccggctga cgagcagctc gggaattgat accgcatggt   1440

ggctggcgag ttcaggaagc aggtgcatgg cttattcctt cacctgatgc acaacatcga   1500

tcaccgagcc atcgcggtaa cgcacaacgg caacgacgcg gtctgtgaat tcaatcggct   1560

gtggttcacc ggtcagcaga cgcgcacgtt cgcgcagcca ctcaatggaa accactttaa   1620

tgcccgcttc ctgcagacgt tct                                            1643
```

```
<210> SEQ ID NO 16
<211> LENGTH: 24
<212> TYPE: RNA
<213> ORGANISM: Artificial
<220> FEATURE:
<223> OTHER INFORMATION: Target specific sequence of the Cpf1-Ecoli#2-
      crRNA#1 (Target#2)

<400> SEQUENCE: 16

ggagaacccg uaugucuuua gcaa                                            24


<210> SEQ ID NO 17
<211> LENGTH: 24
<212> TYPE: RNA
<213> ORGANISM: Artificial
<220> FEATURE:
<223> OTHER INFORMATION: Target specific sequence of the Cpf1-Ecoli#2-
      crRNA#2 (Target#2)
```

<400> SEQUENCE: 17
augcccgcuu ccugcagacg uucu 24

<210> SEQ ID NO 18
<211> LENGTH: 806
<212> TYPE: DNA
<213> ORGANISM: Escherichia coli

<400> SEQUENCE: 18
gtcctttgct tgcgtttagt atcctaaact ggatacccgc ctgatcgatc gctttcgcca 60
tcagaccgcc gagtgcatcc acttctttta ccagatgtcc cttcccaata ccgccgatcg 120
ccgggttgca gctcatctgc cccagagtgt cgatattgtg tgtcaaaagc agagtctgtt 180
gacccatacg cgccgcggcc atcgcggcct cggtgcctgc atgacccccg ccaatgatga 240
tgacgtcaaa aggatccgga taaaacatgg tgattgcctc gcataacgcg gtatgaaaat 300
ggattgaagc ccgggccgtg gattctactc aactttgtcg gcttgagaaa gacctgggat 360
cctgggtatt aaaaagaaga tctatttatt tagagatctg ttctattgtg atctcttatt 420
aggatcgcac tgccctgtgg ataacaagga tccggctttt aagatcaaca acctggaaag 480
gatcattaac tgtgaatgat cggtgatcct ggaccgtata agctgggatc agaatgaggg 540
gttatacaca actcaaaaac tgaacaacag ttgttctttg gataactacc ggttgatcca 600
agcttcctga cagagttatc cacagtagat cgcacgatct gtatacttat ttgagtaaat 660
taacccacga tcccagccat tcttctgccg gatcttccgg aatgtcgtga tcaagaatgt 720
tgatcttcag tgtttcgcct gtctgttttg caccggaatt tttgagttct gcctcgagtt 780
tatcgatagc ccccacaaaag gtgtca 806

<210> SEQ ID NO 19
<211> LENGTH: 24
<212> TYPE: RNA
<213> ORGANISM: Artificial
<220> FEATURE:
<223> OTHER INFORMATION: Target specific sequence of the Cpf1-oriC-crRNA#1 (Target oriC)

<400> SEQUENCE: 19
ggauacuaaa cgcaagcaaa ggac 24

<210> SEQ ID NO 20
<211> LENGTH: 24
<212> TYPE: RNA
<213> ORGANISM: Artificial
<220> FEATURE:
<223> OTHER INFORMATION: Target specific sequence of the Cpf1-oriC-crRNA#2 (Target oriC)

<400> SEQUENCE: 20
ucgauagccc cacaaaaggu guca 24

<210> SEQ ID NO 21
<211> LENGTH: 20
<212> TYPE: RNA
<213> ORGANISM: Artificial
<220> FEATURE:
<223> OTHER INFORMATION: Target specific sequence of the Cas9-Ecoli#1-crRNA#1 (Target#1)

<400> SEQUENCE: 21
caucagugac auccuaucac 20

-continued

<210> SEQ ID NO 22
<211> LENGTH: 20
<212> TYPE: RNA
<213> ORGANISM: Artificial
<220> FEATURE:
<223> OTHER INFORMATION: Target specific sequence of the Cas9-Ecoli#1-crRNA#2 (Target#1)

<400> SEQUENCE: 22
ccggaugaac uuuaucgaaa 20

<210> SEQ ID NO 23
<211> LENGTH: 20
<212> TYPE: RNA
<213> ORGANISM: Artificial
<220> FEATURE:
<223> OTHER INFORMATION: Target specific sequence of the Cas9-Ecoli#2-crRNA#1 (Target#2)

<400> SEQUENCE: 23
ccggagauaa ucgagaucgg 20

<210> SEQ ID NO 24
<211> LENGTH: 20
<212> TYPE: RNA
<213> ORGANISM: Artificial
<220> FEATURE:
<223> OTHER INFORMATION: Target specific sequence of the Cas9-Ecoli#2-crRNA#2 (Target#2)

<400> SEQUENCE: 24
gaacgugcgc gucugcugac 20

<210> SEQ ID NO 25
<211> LENGTH: 24
<212> TYPE: RNA
<213> ORGANISM: Artificial
<220> FEATURE:
<223> OTHER INFORMATION: Target specific sequence of the Cas9-oriC-crRNA#1 (Target oriC)

<400> SEQUENCE: 25
ggauacuaaa cgcaagcaaa ggac 24

<210> SEQ ID NO 26
<211> LENGTH: 24
<212> TYPE: RNA
<213> ORGANISM: Artificial
<220> FEATURE:
<223> OTHER INFORMATION: Target specific sequence of the Cas9-oriC-crRNA#12 (Target oriC)

<400> SEQUENCE: 26
ucgauagccc cacaaaaggu guca 24

<210> SEQ ID NO 27
<211> LENGTH: 1550
<212> TYPE: DNA
<213> ORGANISM: Escherichia coli

<400> SEQUENCE: 27
cgacaacctg aacggttggg cgaagaaaga gaatctgaaa aactacgttg tctatgaaac 60
gacgcgtaat ggtcagccgt ggtatgtcct ggtttctggc gtgtacgctt cgaaagaaga 120
ggcgaaaaaa gcggtatcta cattgccagc agatgtccag gccaaaaacc cgtgggcgaa 180

```
accgctgcgt caggtacagg ccgatctgaa gtaatcaagg ttatctcccg caatggttta    240

tcgttgcggg agttgcctga agcgctggat gctgtcggag ctttctccac agccggagaa    300

ggtgtaatta gttagtcagc atgaagaaaa atcgcgcttt tttgaagtgg gcagggggca    360

agtatcccct gcttgatgat attaaacggc atttgcccaa gggcgaatgt ctggttgagc    420

cttttgtagg tgccgggtcg gtgtttctca acaccgactt ttctcgttat atccttgccg    480

atatcaatag cgacctgatc agtctctata acattgtgaa gatgcgtact gatgagtacg    540

tacaggccgc acgcgagctg tttgttcccg aaacaaattg cgccgaggtt tactatcagt    600

tccgcgaaga gttcaacaaa agccaggatc cgttccgtcg ggcggtactg tttttatatt    660

tgaaccgcta cggttacaac ggcctgtgtc gttacaatct gcgcggtgag tttaacgtgc    720

cgttcggccg ctacaaaaaa ccctatttcc cggaagcaga gttgtatcac ttcgctgaaa    780

aagcgcagaa tgcctttttc tattgtgagt cttacgccga tagcatggcg cgcgcagatg    840

atgcatccgt cgtctattgc gatccgcctt atgcaccgct gtctgcgacc gccaacttta    900

cggcgtatca cacaaacagt tttacgcttg aacaacaagc gcatctggcg gagatcgccg    960

aaggtctggt tgagcgccat attccagtgc tgatctccaa tcacgatacg atgttaacgc   1020

gtgagtggta tcagcgcgca aaattgcatg tcgtcaaagt tcgacgcagt ataagcagca   1080

acggcggcac acgtaaaaag gtggacgaac tgctggcttt gtacaaacca ggagtcgttt   1140

cacccgcgaa aaaataattc tcaaggagaa gcggatgaaa cagtatttga ttgcccccctc   1200

aattctgtcg gctgattttg cccgcctggg tgaagatacc gcaaaagccc tggcagctgg   1260

cgctgatgtc gtgcattttg acgtcatgga taaccactat gttcccaatc tgacgattgg   1320

gccaatggtg ctgaaatcct tgcgtaacta tggcattacc gcccctatcg acgtacacct   1380

gatggtgaaa cccgtcgatc gcattgtgcc tgatttcgct gccgctggtg ccagcatcat   1440

tacctttcat ccagaagcct ccgagcatgt tgaccgcacg ctgcaactga ttaaagaaaa   1500

tggctgtaaa gcgggtctgg tatttaaccc ggcgacacct ctgagctatc              1550
```

<210> SEQ ID NO 28
<211> LENGTH: 24
<212> TYPE: RNA
<213> ORGANISM: Artificial
<220> FEATURE:
<223> OTHER INFORMATION: Target specific sequence of the Cpf1-dam-crRNA#1 (Target dam)

<400> SEQUENCE: 28

```
uucgcccaac cguucagguu gucg                                            24
```

<210> SEQ ID NO 29
<211> LENGTH: 24
<212> TYPE: RNA
<213> ORGANISM: Artificial
<220> FEATURE:
<223> OTHER INFORMATION: Target specific sequence of the Cpf1-dam-crRNA#2 (Target dam)

<400> SEQUENCE: 29

```
gcugccgcug gugccagcau cauu                                            24
```

<210> SEQ ID NO 30
<211> LENGTH: 24
<212> TYPE: RNA
<213> ORGANISM: Artificial
<220> FEATURE:
<223> OTHER INFORMATION: Target specific sequence of the Cas9-damcrRNA#1 (Target dam)

<400> SEQUENCE: 30
uucgcccaac cguucagguu gucg 24

<210> SEQ ID NO 31
<211> LENGTH: 24
<212> TYPE: RNA
<213> ORGANISM: Artificial
<220> FEATURE:
<223> OTHER INFORMATION: Target specific sequence of the Cas9-dam-
crRNA#2 (Target dam)

<400> SEQUENCE: 31
gcugccgcug gugccagcau cauu 24

<210> SEQ ID NO 32
<211> LENGTH: 51
<212> TYPE: DNA
<213> ORGANISM: Artificial
<220> FEATURE:
<223> OTHER INFORMATION: PS1150 (5'Biotin for the Ecoli Target #1 )

<400> SEQUENCE: 32
tggtcaagca tgccgctttt cggttcccgg gtgaagaatc ttcggtttgc g 51

<210> SEQ ID NO 33
<211> LENGTH: 50
<212> TYPE: DNA
<213> ORGANISM: Artificial
<220> FEATURE:
<223> OTHER INFORMATION: PS1219 (5'Biotin for the Ecoli Target #2 )

<400> SEQUENCE: 33
tggtcaagca tgccgctttt cggttcccgg atcagtaggt cagcactgcc 50

<210> SEQ ID NO 34
<211> LENGTH: 50
<212> TYPE: DNA
<213> ORGANISM: Artificial
<220> FEATURE:
<223> OTHER INFORMATION: PS1396 (5'Biotin for the Ecoli Target oriC )

<400> SEQUENCE: 34
tggtcaagca tgccgctttt cggttcccgg atacccgcct gatcgatcgc 50

<210> SEQ ID NO 35
<211> LENGTH: 53
<212> TYPE: DNA
<213> ORGANISM: Artificial
<220> FEATURE:
<223> OTHER INFORMATION: PS1395  (5'Biotin for the Ecoli Target dam )

<400> SEQUENCE: 35
tggtcaagca tgccgctttt cggttcccgc tacgttgtct atgaaacgac gcg 53

<210> SEQ ID NO 36
<211> LENGTH: 46
<212> TYPE: DNA
<213> ORGANISM: Artificial
<220> FEATURE:
<223> OTHER INFORMATION: PS1421 (3'Phosphate surface for the Ecoli
Target #1 )

<400> SEQUENCE: 36
tgacgaggtc tccattcgcg ttcagacggt aattgttcac cttcgc 46

<210> SEQ ID NO 37
<211> LENGTH: 46
<212> TYPE: DNA
<213> ORGANISM: Artificial
<220> FEATURE:
<223> OTHER INFORMATION: PS1422 (3'Phosphate surface for the Ecoli Target #2 )

<400> SEQUENCE: 37
tgacgaggtc tccattcatc ttttgctaaa gacatacggg ttctcc 46

<210> SEQ ID NO 38
<211> LENGTH: 46
<212> TYPE: DNA
<213> ORGANISM: Artificial
<220> FEATURE:
<223> OTHER INFORMATION: PS1425 (3'Phosphate surface for the Ecoli Target oriC )

<400> SEQUENCE: 38
tgacgaggtc tccattccgc cggtcctttg cttgcgttta gtatcc 46

<210> SEQ ID NO 39
<211> LENGTH: 46
<212> TYPE: DNA
<213> ORGANISM: Artificial
<220> FEATURE:
<223> OTHER INFORMATION: PS1423 (3'Phosphate surface for the Ecoli Target dam )

<400> SEQUENCE: 39
tgacgaggtc tccattcaac tacgacaacc tgaacggttg ggcgaa 46

<210> SEQ ID NO 40
<211> LENGTH: 29
<212> TYPE: DNA
<213> ORGANISM: Artificial
<220> FEATURE:
<223> OTHER INFORMATION: PS1420 (oligonucleotide for surface adaptor with 5' phosphate)

<400> SEQUENCE: 40
gaatccactt cctaatctgt catcttctg 29

<210> SEQ ID NO 41
<211> LENGTH: 57
<212> TYPE: DNA
<213> ORGANISM: Artificial
<220> FEATURE:
<223> OTHER INFORMATION: PS867 (oligonucleotide for surface adaptor)

<400> SEQUENCE: 41
gtgtcttttg gtctttctgg tgctcttcga atcagaagat gacagattag gaagtgg 57

<210> SEQ ID NO 42
<211> LENGTH: 48
<212> TYPE: DNA
<213> ORGANISM: Artificial
<220> FEATURE:
<223> OTHER INFORMATION: PS1268 (Loop for the Ecoli Target #1 )

<400> SEQUENCE: 42
gtattagctg aggaccgata ccgatgccat gctacttggc ggtctgat 48

<210> SEQ ID NO 43

<211> LENGTH: 48
<212> TYPE: DNA
<213> ORGANISM: Artificial
<220> FEATURE:
<223> OTHER INFORMATION: PS1221 (Loop for the Ecoli Target #2 )

<400> SEQUENCE: 43
gtattagctg aggaccgatc tggcagaacg tctgcaggaa gcgggcat 48

<210> SEQ ID NO 44
<211> LENGTH: 46
<212> TYPE: DNA
<213> ORGANISM: Artificial
<220> FEATURE:
<223> OTHER INFORMATION: PS1378 (Loop for the Ecoli Target oriC )

<400> SEQUENCE: 44
tgacgaggtc tcctttagaa tatgacacct tttgtggggc tatcga 46

<210> SEQ ID NO 45
<211> LENGTH: 46
<212> TYPE: DNA
<213> ORGANISM: Artificial
<220> FEATURE:
<223> OTHER INFORMATION: PS1424 (Loop for the Ecoli Target dam )

<400> SEQUENCE: 45
tgacgaggtc tcctttaaag gtaatgatgc tggcaccagc ggcagc 46

<210> SEQ ID NO 46
<211> LENGTH: 26
<212> TYPE: DNA
<213> ORGANISM: Artificial
<220> FEATURE:
<223> OTHER INFORMATION: PS421 Loop oligonucleotide with 5' phosphate

<400> SEQUENCE: 46
taaagcactg agatttttct cagtgc 26

<210> SEQ ID NO 47
<211> LENGTH: 2250
<212> TYPE: DNA
<213> ORGANISM: Homo sapiens

<400> SEQUENCE: 47
cccagagcag ggcgtcatgc acaagaaagc tttgcacttt gcgaaccaac gataggtggg 60
ggtgcgtgga ggatggaaca cggacggccc ggcttgctgc cttcccaggc ctgcagtttg 120
cccatccacg tcagggcctc agcctggccg aaagaaagaa atggtctgtg atccccccag 180
cagcagcagc agcagcagca gcagcagcag cagcagcagc agcagcagca gcagcagcat 240
tcccggctac aaggaccctt cgagccccgt tcgccggccg cggacccggc ccctccctcc 300
ccggccgcta gggggcgggc ccggatcaca ggactggagc tgggcggaga cccacgctcg 360
gagcggttgt gaactggcag gcggtgggcg cggcttctgt gccgtgcccc gggcactcag 420
tcttccaacg ggccccgga gtcgaagaca gttctagggt tcagggagcg cgggcggctc 480
ctgggcggcg ccagactgcg gtgagttggc cggcgtgggc caccaaccca atgcagccca 540
gggcggcggc acgagacaga acaacggcga acaggagcag ggaaagcgcc tccgataggc 600
caggcctagg gacctgcggg gagagggcga ggtcaacacc cggcatgggc ctctgattgg 660
ctcctgggac tcgccccgcc tacgcccata ggtgggcccg cactcttccc tgcgccccgc 720
ccccgcccca acagcctaca gctgttgtta gtccactcgc acgcctcgaa tcccgtccga 780
actcgtcatt ggctgcttcc tagcggcctg tgttgattgg ctgcccgaag atccgccctc 840
ctgccgtggg cccagccccg caaatgcgca gctaagcggg tggcaagggg cgggtggagc 900
gcggggcgcg acggcggagg ggggcgtggg cagccggacg taccctggca gggagcagca 960
ggtggcggcg gtgcatgggg cctggcccca ccagcgggca ctggcccaca gccacggccg 1020
gggggccatc tagctggaga gagaagggac aggtgacccg atcggagccc agcccagccc 1080
tcagcggtgg ggcgagagac agcgagggga atcgaggttg gggaggttat ctagggagat 1140
cccggaggga atctggtgag gcctgaacgg agggagatct ggggctgaat aaagggcttc 1200
tgccctctaa agtcgcaaag acgtagggtg agccctatat ctggacgggg agaccaggag 1260
ccagggaggg gatctgcaga atgggcagca ggtctgaggc aggggaaaga gaggggtctt 1320
acatgggaag gtggatccgt ggcccgggga ctggggaccc ccgtgacagc tggaaggaga 1380
agaaagaggc atagggcgcg tggaggggcg aaggagggcg gtggcgcggc gtgccccagc 1440
gtgggtccct tccctcctcc aggtgtctat acacgccccg cggagcagac ggcccacctc 1500
ctcccggtcc tccggggaag gggacacatg agggactcac ctgtggctcc ctctgcctgc 1560
agcaactcca tccgctcctg caactgccgg acgtgtgcct ctaggtcccg gttccgagcc 1620
tctgcctcgc gtagttgact gtggggaggt aaggacggtg agtccgtccg ggccggacga 1680
gaggggatgc caagggttgc caccggcccg catcccggcc ccggccccgg ccccgatccc 1740
gacctggcga agttctggtt gtccgtgcgg atggcctcca tctcccggct caggctctgc 1800
cgggtgagca cctcctcctc cagggcttcc tggagctccc gcagcgtcac ctcggcctca 1860
gcctctgccg cagggacagc cgctggaact gccacttcag cctgtgtatg gggaccaggc 1920
ttaaggctgc ctgtggctcc tggaagactc aggacttggg cactggttcc aggctaggaa 1980
tccttgttta tcccctactc ctccgtcccc tcaacatttc tggaatcccc atagctcctg 2040
caatgatcca agcccctcc cttccctacc tccctcagcc ccatccctga gtctggtcct 2100
ctaaatctac acagggacca gagggctggt gctcaaacac taacacaacc tatgtccctc 2160
tgctgctcaa aatccctcca gctccctaat gccctcacga caaaaggcct tgctgggttt 2220
tgtttcctgc tggcctctcc agccttctca 2250

<210> SEQ ID NO 48
<211> LENGTH: 1487
<212> TYPE: DNA
<213> ORGANISM: Homo sapiens

<400> SEQUENCE: 48
aatgcactta acagtgtctt acggtaaaaa caaaatttca tccaccaatt atgtgttgag 60
cgcccactgc ctaccaagca caaacaaaac cattcaaaac cacgaaatcg tcttcacttt 120
ctccagatcc agcagcctcc cctattaagg ttcgcacacg ctattgcgcc aacgctcctc 180
cagagcgggt cttaagataa aagaacagga caagttgccc cgccccattt cgctagcctc 240
gtgagaaaac gtcatcgcac atagaaaaca gacagacgta acctacggtg tcccgctagg 300
aaagagaggt gcgtcaaaca gcgacaagtt ccgcccacgt aaaagatgac gcttggtgtg 360
tcagccgtcc ctgctgcccg gttgcttctc ttttgggggc ggggtctagc aagagcaggt 420
gtgggtttag gaggtgtgtg tttttgtttt tcccaccctc tctccccact acttgctctc 480
acagtactcg ctgagggtga acaagaaaag acctgataaa gattaaccag aagaaaacaa 540
ggagggaaac aaccgcagcc tgtagcaagc tctggaactc aggagtcgcg cgctaggggc 600

```
cggggccggg gccggggcgt ggtcggggcg ggcccggggg cgggcccggg gcggggctgc    660

ggttgcggtg cctgcgcccg cggcggcgga ggcgcaggcg gtggcgagtg ggtgagtgag    720

gaggcggcat cctggcgggt ggctgtttgg ggttcggctg ccgggaagag gcgcgggtag    780

aagcgggggc tctcctcaga gctcgacgca tttttacttt ccctctcatt tctctgaccg    840

aagctgggtg tcgggctttc gcctctagcg actggtggaa ttgcctgcat ccgggccccg    900

ggcttcccgg cggcggcggc ggcggcggcg gcgcagggac aagggatggg gatctggcct    960

cttccttgct ttcccgccct cagtacccga gctgtctcct tcccggggac ccgctgggag   1020

cgctgccgct gcgggctcga gaaaagggag cctcgggtac tgagaggcct cgcctggggg   1080

aaggccggag ggtgggcggc gcgcggcttc tgcggaccaa gtcggggttc gctaggaacc   1140

cgagacggtc cctgccggcg aggagatcat gcgggatgag atgggggtgt ggagacgcct   1200

gcacaatttc agcccaagct tctagagagt ggtgatgact tgcatatgag ggcagcaatg   1260

caagtcggtg tgctccccat tctgtgggac atgacctggt tgcttcacag ctccgagatg   1320

acacagactt gcttaaagga agtgactatt gtgacttggg catcacttga ctgatggtaa   1380

tcagttgtct aaagaagtgc acagattaca tgtccgtgtg ctcattgggt ctatctggcc   1440

gcgttgaaca ccaccaggct ttgtattcag aaacaggagg gaggtcc                 1487
```

<210> SEQ ID NO 49
<211> LENGTH: 1272
<212> TYPE: DNA
<213> ORGANISM: Homo sapiens

<400> SEQUENCE: 49

```
aagcgagaat ggaggaatac aagccaaagg gaaggaaggg gacgaaggcg gacagggagt     60

gacctcttcc tccaaccccc gggcccgctg ggagcggcgc gaggccagag gcccttgaga    120

ggctcgggct gtcctggggg cctcagtcct ctgcctgtac cccatggggg accctgctgc    180

caccaggcgc cccgcactca ctcgacctgc agcgtgctgg gtttaatctt cacctcaacc    240

ttgtaggagg agccggtgag cagcttgatg gtgcggttct ggccgaagcg ctgcccgtcc    300

accttgtaaa agaccgggcc gtcattaggc tggatgcgca gcgcgatgga gaggcgcacg    360

aggcccggca ggtcccccat gtctgggcga gggtctggcg cggcggctcc gggggggcgga    420

ggacagcgcc ggctgcggcc gagtggctgg agcgcgaggg gcggagagga agcgcgggga    480

gggtgaggga ggtggtggag ctgaggctgc cgctaggaac ccgcgccgtc gccgccgtcc    540

gcccgggctt ttgaggagca gctccttagg ctgtggcccc cctccccact cggcgaggaa    600

gcgggcccaa gagacggctc caaggccgcg cgcttcccca tcccccgctc cagtgctgcg    660

ccctccacgc acccgaaggc tcgctctggc ccgcaggccg ccgcgcagat ccgcgcagct    720

gggggcgagg gagttaatcc tgtttacgca ccacaatccc cttcagctgg ggaagcggac    780

atttaggctc ctcctagaac agccccgggc aggaggagga gaggtttggg aggcactggg    840

aaggcgctgg agttaagcga ccactatgcc aaggagcgag acccccggaa tctggatacc    900

gcctcggcca gctacgtgag gtggacactg ctgctcgcgg atccggcgcc agccaggcgg    960

gaggaggctg aggggggta aagggaggcg ggaagggggg acaggaaacc gctagccggt   1020

gatttaaatt tcaggaaata tgagtctttc caaagcttag ggaaatggc cgaggaaagg   1080

cgcaattcca cgtgatggag ccacgctgga tgaggaatgg atgcaagagg aagaaaataa   1140

ccatattcaa ggagctacat cttcttgtgg gtgtacattt ccattatacg tatgctcgtc   1200

ccaaaaatga cacatacata aatatatgta atgaatcaca tatatttaca cagattttga   1260
```

agggtgagct at 1272

<210> SEQ ID NO 50
<211> LENGTH: 2352
<212> TYPE: DNA
<213> ORGANISM: Homo sapiens

<400> SEQUENCE: 50
gggcagtggg acacttagcc tctctaaaag cacctccacg gctgtttgtg tcaagccttt 60
attccaagag cttcactttt gcgaagtaat gtgcttcaca cattggcttc aaagtaccca 120
tggctggttg caataaacat taaggaggcc tgtctctgca cccggagttg ggtgccctca 180
tttcagatga tttcgagggt gcttgacaag atctgaagga ccctcggact ttagagcacc 240
acctcggacg cctggcaccc ctgccgcgcg ggcacggcga cctcctcagc tgccaggcca 300
gcctctgatc cccgagaggg tcccgtagtg ctgcagggga ggtggggacc cgaataaagg 360
agcagtttcc ccgtcggtgc cattatccga cgctggctct aaggctcggc cagtctgtct 420
aaagctggta caagtttgct ttgtaaaaca aaagaaggga aagggggaag gggaccctgg 480
cacagatttg gctcgacctg gacataggct gggcctgcaa gtccgcgggg accgggtcca 540
gaggggcagt gctgggaacg cccctctcgg aaattaactc ctcagggcac ccgctcccct 600
cccatgcgcc gccccactcc cgccggagac taggtcccgc gggggccacc gctgtccacc 660
gcctccggcg gccgctggcc ttgggtcccc gctgctggtt ctcctccctc ctcctcgcat 720
tctcctcctc ctctgctcct cccgatccct cctccgccgc ctggtccctc ctcctcccgc 780
cctgcctccc cgcgcctcgg cccgcgcgag ctagacgtcc gggcagcccc cggcgcagcg 840
cggccgcagc agcctccgcc ccccgcacgg tgtgagcgcc cgacgcggcc gaggcggccg 900
gagtcccgag ctagccccgg cggccgccgc cgcccagacc ggacgacagg ccacctcgtc 960
ggcgtccgcc cgagtccccg cctcgccgcc aacgccacaa ccaccgcgca cggccccctg 1020
actccgtcca gtattgatcg ggagagccgg agcgagctct tcggggagca gcgatgcgac 1080
cctccgggac ggccggggca gcgctcctgg cgctgctggc tgcgctctgc ccggcgagtc 1140
gggctctgga ggaaaagaaa ggtaagggcg tgtctcgccg gctcccgcgc cgcccccgga 1200
tcgcgccccg gaccccgcag cccgcccaac cgcgcaccgg cgcaccggct cggcgcccgc 1260
gcccccgccc gtcctttcct gtttccttga gatcagctgc gccgccgacc gggaccgcgg 1320
gaggaacggg acgtttcgtt cttcggccgg gagagtctgg ggcgggcgga ggaggagacg 1380
cgtgggacac cgggctgcag gccaggcggg gaacggccgc cgggacctcc ggcgccccga 1440
accgctccca actttcttcc ctcactttcc ccgcccagct gcgcaggatc ggcgtcagtg 1500
ggcgaaagcc gggtgctggt gggcgcctgg ggccggggtc ccgcacgtgc gccccgcgct 1560
gtcttcccag ggcgcgacgg ggtcctggcg cgcacccgag gggcgggcgc tgcccacccg 1620
ccgagactgc actgtttagg gaagctgagg aaggaaccca aaaatacagc ctcccctcgg 1680
accccgcggg acaggcggct ttctgagagg acctccccgc ctccgccctc cgcgcaggtc 1740
tcaaactgaa gccggcgccc gccagcctgg ccccggcccc tctccaggtc cccgcgatcc 1800
tcgttcccca gtgtggagtc gcagcctcga cctgggagct gggagaactc gtctaccacc 1860
acctgcggct cccggggagg ggtggtgctg gcggcggtta gtttcctcgt tggcaaaagg 1920
caggtggggt ccgacccgcc ccttgggcgc agaccccggc cgctcgcctc gcccggtgcg 1980
ccctcgtctt gcctatccaa gagtgccccc cacctcccgg ggaccccagc tccctcctgg 2040
gcgcccgcgc cgaaagcccc aggctctcct tcgatggccg cctcgcggag acgtccgggt 2100
ctgctccacc tgcagccctt cggtcgcgcc tgggcttcgc ggtggagcgg gacgcggctg 2160
tccggccact gcaggggggg atcgcgggac tcttgagcgg aagccccgga agcagagctc 2220
atcctggcca acaccatggt gtttcaaaat ggggctcaca gcaaacttct cctcaaaacc 2280
cggagacttt ctttcttgga tgtctctttt tgctgtttga agaatttgag ccaaccaaaa 2340
tattaaacct gt 2352

<210> SEQ ID NO 51
<211> LENGTH: 1711
<212> TYPE: DNA
<213> ORGANISM: Homo sapiens

<400> SEQUENCE: 51
tgaggtttgt ttcacagtgg aatgtaaagg gttgcaagga ggtgcatcgg cccctgtgga 60
caggacgcat gactgctaca cacgtgttca ccccaccctc tggcacaggg tgcacataca 120
gtaggggcag aaatgaacct caagtgctta acacaatttt taaaaaatat atagtcaagt 180
gaaagtatga aaatgagttg aggaaaggcg agtacgtggg tcaaagctgg gtctgaggaa 240
aggctcacat tttgagatcc cgactcaatc catgtccctt aaagggcaca gggtgtctcc 300
acagggccgc ccaaaatctg gtgagagagg gcgtagacgc ctcaccttct gcctctacgg 360
gtcacaaaag cctgggtcac cctggttgcc actgttccta gttcaaagtc ttcttctgtc 420
taatccttca cccctattct cgccttccac tccacctccc gctcagtcag actgcgctac 480
tttgaaccgg accaaaccaa accaaaccaa accaaaccaa accagaccag acaccccctc 540
ccgcggaatc ccagagaggc cgaactggga taaccggatg catttgattt cccacgccac 600
tgagtgcacc tctgcagaaa tgggcgttct ggccctcgcg aggcagtgcg acctgtcacc 660
gcccttcagc cttcccgccc tccaccaagc ccgcgcacgc ccggcccgcg cgtctgtctt 720
tcgacccggc accccggccg gttcccagca gcgcgcatgc gcgcgctccc aggccacttg 780
aagagagagg gcggggccga ggggctgagc ccgcgggggg agggaacagc gttgatcacg 840
tgacgtggtt tcagtgttta cacccgcagc gggccggggg ttcggcctca gtcaggcgct 900
cagctccgtt tcggtttcac ttccggtgga gggccgcctc tgagcgggcg gcgggccgac 960
ggcgagcgcg ggcggcggcg gtgacggagg cgccgctgcc agggggcgtg cggcagcgcg 1020
gcggcggcgg cggcggcggc ggcggcggag gcggcggcgg cggcggcggc ggcggcggct 1080
gggcctcgag cgcccgcagc ccacctctcg gggggcgggct cccggcgcta gcagggctga 1140
agagaagatg gaggagctgg tggtggaagt gcggggctcc aatggcgctt tctacaaggt 1200
acttggctct agggcaggcc ccatcttcgc ccttccttcc ctccctttttc ttcttggtgt 1260 cggcgggagg caggcccggg gccctcttcc cgagcaccgc gcctgggtgc cagggcacgc 1320
tcggcgggat gttgttggga gggaaggact ggacttgggg cctgttggaa gcccctctcc 1380
gactccgaga ggccctagcg cctatcgaaa tgagagacca gcgaggagag ggttctcttt 1440
cggcgccgag ccccgccggg gtgagctggg gatgggcgag ggccggcggc aggtactaga 1500
gccgggcggg aagggccgaa atcggcgcta agtgacggcg atggcttatt ccccctttcc 1560
taaacatcat ctcccagcgg gatccgggcc tgtcgtgtgg gtagttgtgg aggagcgggg 1620
ggcgcttcag ccgggccgcc tcctgcagcg ccaagagggc ttcaggtctc ctttggcttc 1680
tcttttccgg tctagcattg ggacttcgga g 1711

<210> SEQ ID NO 52
<211> LENGTH: 2266
<212> TYPE: DNA
<213> ORGANISM: Homo sapiens

<400> SEQUENCE: 52

```
aaccacgtcc tctcctttgg ggcagaaatc tctgggagta ggggcaaggt agtttaacca     60
cgaacggggt ggggactaaa caaccctagc acctctaagg tgcccccagg aggtcttgcc    120
aaggagtctt ccacagggag agtcatcctg cccgttgttc tggatcttga aacttgggag    180
acccacacca aaggagggaa ccggttcctt taccctttaa gcgcgtcgtg tcctccaccg    240
cctcttctct tggcccgact ggctctggtt tccttcacgt tcccagcctc caaattggcg    300
tccgccccat ggctcgtgta ggacgctaaa agcacggtaa atcccagggc gatctccagc    360
agacgccctc gacgcatgat gccgagccgc caccggctcc cgccgcctct tgccgcgccc    420
ggggctcggt ctgcggccgc cgctgcgccc tgaagcgcac cgcgccgccg gggtcccgct    480
atcccgccgc ccgtccccccg ggccgggctc ctcccgcctt ctccaggcgc tgctcccact    540
tcaggcggcc cctgccagct gcaacacaga gacaaatccc cgaggcgggg agactttcag    600
ggcatcggga tgctgaagcc tcgcggtccc cattcccaag cccaacccgt gcgccgcctg    660
cgcgtggcgc agttaatttg ggtaagggaa gaccgtttgg tccacagctg gctggaaagc    720
ccaggccccc ggcggcagca gccccggccg atccctcggc ctcccgggcc ccgccagaag    780
agcgcggcgc aaagtaccca tatccccagc ggtcctaagc cccgggcgag ctctctgggt    840
ttattttttt tagcggcacg aattgcgcgc gatgcgcgct ctgaacgccc cactcctcag    900
cctgccctct ccgccaggct ggaagccagc cgcgccgtcc ccgccgactc cgggcgatgc    960
caccgccccc cgaacatctg acgcggagcc cggcaccaag agccccgggc caggaagctg   1020
tcaggcaggg gagggccagc gccagctgtg gacgttccgg gacagcccct caccccagtc   1080
cctgtccctg ccctcggcgc ggcgcaaacg caaaagcctc cgtggccgca gctccagccc   1140
cggtggccgc ccgacccccg tcgggacccc ggctgcaccc actggagaag cggcggctcc   1200
gactcccgag gaggcggcgg cggctgctcc cagtcgtggc cgctacagcc actgctcggc   1260
tccgctcgca gctgtcccag ctgtggctcc tgtccgcttg tggcacccac agtctctgcc   1320
gcggctcccg cagcccccctc ctttccccac ctcttcaagt atcgtccgcg cagcggtttc   1380
tcgcgagaga aatacttttt ttaaaaaaag aaagaaaaag aaaatgacac cccctccttc   1440
gtcgccctca tcaccacccc accccccggc cccatccatc ctccctttcc actccccttt   1500
gccagcctcc gcctcggtgc ggggcctctc gctcgcagga ttagcgcagt gggaggaggc   1560
agaggtgatc aggtcctgcc cggcctggga ctttttgtct tgaggtgggg aggggagaaa   1620
tgggaagagg tggagtagcg gttttagccc gctctgcggc tgcgaggttt agatccgaga   1680
ttaacctctc ccgcgatagg tgaagcccta ccggagcaga aagctgttcc acctgcacca   1740
agaatgcgcg ctggagacgg ttgccccgga ggccctggcc cgagagaaaa ccagtccccg   1800
ctgcccgcgc ctcccggtag cgcgctccct gcgcctctcc cgccggacac tcagcagacg   1860
ccggaggccg ggaggctaag actgggcgcg tcgcaggccg ggaccgcggc agaggctgct   1920
gtgccgaccg aggagagggc tctgccgccc ccacttgccc tgggtgtcga gagcccactc   1980
cagacgcggc tcttctgagg ctcaattcaa gccacccagg cctgaatcca gggtgctctc   2040
tctaagtcgg tgtccaaccc aggggcctgt aaatgttgga acctaggatg taggatggga   2100
gcggtgaagg gatggtcctc ttgcccagcc cagattaaga ctggggttca tctggaggac   2160
```

```
tctacttaca ccctcccggt cccctcgccc tcccccacac acagctgcct ctccccagga   2220

tatgcgcggc acagtgaatt tagtggcttt gaaaggtata gtattt                  2266


<210> SEQ ID NO 53
<211> LENGTH: 1643
<212> TYPE: DNA
<213> ORGANISM: Homo sapiens

<400> SEQUENCE: 53

ggtcagagca ggggtgcact cccataaaga aacgccccca ggtcgggact cattcctgtg     60

ggcggcatct tgtggccata gctgcttctc gctgcactaa tcacagtgcc tctgtgggca    120

gcaggcgctg accacccagg cctgccccag accctctcct cccttccggg gcgctgcgct    180

gggaccgatg gggggcgcca ggcctgtgga caccgccctg caggggcctc tccagctcac    240

tgggggtggg gtgggggtca cacttggggt cctcaggtcg tgccgaccac gcgcattctc    300

tgcgctctgc gcaggagctc gcccaccctc tccccgtgca gagagccccg cagctggctc    360

cccgcagggc tgtccgggtg agtatggctc tggccacggg ccagtgtggc gggagggcaa    420

accccaaggc cacctcggct cagagtccac ggccggctgt cgccccgctc caggcgtcgg    480

cgggggatcc tttccgcatg ggcctgcgcc cgcgctcggc gccccctcca cggccccgcc    540

ccgtccatgg ccccgtcctt catgggcgag cccctccatg gccctgcccc tccgcgcccc    600

acccctccct cgccccacct ctcaccttcc tgccccgccc ccagcctccc cacccctcac    660

cggccagtcc cctcccctat cccgctccgc ccctcagccg ccccgcccct cagccggcct    720

gcctaatgtc cccgtcccca gcatcgcccc gccccgcccc cgtctcgccc cgcccctcag    780

gcggcctccc tgctgtgccc cgccccggcc tcgccacgcc cctacctcac cacgcccccc    840

gcatcgccac gcccccgca tcgccacgcc tcccttacca tgcagtcccg ccccgtccct    900

tcctcgtccc gcctcgccgc gacacttcac acacagcttc gcctcacccc attacagtct    960

caccacgccc cgtcccctct ccgttgagcc ccgcgccttc gcccgggtgg ggcgctgcgc   1020

tgtcagcggc cttgctgtgt gaggcagaac ctgcgggggc aggggcgggc tggttccctg   1080

gccagccatt ggcagagtcc gcaggctagg gctgtcaatc atgctggccg gcgtggcccc   1140

gcctccgccg gcgcggcccc gcctccgccg gcgcagcgtc tgggacgcaa ggcgccgtgg   1200

gggctgccgg gacgggtcca agatggacgg ccgctcaggt tctgctttta cctgcggccc   1260

agagccccat tcattgcccc ggtgctgagc ggcgccgcga gtcggcccga ggcctccggg   1320

gactgccgtg ccgggcggga gaccgccatg gcgaccctgg aaaagctgat gaaggccttc   1380

gagtccctca agtccttcca gcagcagcag cagcagcagc agcagcagca gcagcagcag   1440

cagcagcagc agcagcaaca gccgccaccg ccgccgccgc cgccgccgcc tcctcagctt   1500

cctcagccgc cgccgcaggc acagccgctg ctgcctcagc cgcagccgcc cccgccgccg   1560

cccccgccgc cacccggccc ggctgtggct gaggagccgc tgcaccgacc gtgagtttgg   1620

gcccgctgca gctccctgtc ccg                                           1643


<210> SEQ ID NO 54
<211> LENGTH: 1816
<212> TYPE: DNA
<213> ORGANISM: Homo sapiens

<400> SEQUENCE: 54

ctctgcaggt cctcactgta actggaaaaa cacgacctcg ccctcgggaa ggctttctgt     60

gcgcctcacc tcaggatgag ggtgggtgta ggggacacct cccagaaacc cctaacctcc    120
```

```
cagtcggtta aagaagaggg gatagggtca agggatgcga cagagctgtg tggtttccgg    180

atgggaaacc tcagtcgttt aggcacccct ccgctcgagt cacttccgaa gcagtcgatt    240

cttggggaga agcgctgcgg aaaggggcga ctccgatgca gatggccctg tcccggcgcc    300

ccaggtcgtc gcgcgcgcag ctgcggtagt cactgcgcct ccccgccccc actcctggat    360

gccccccttc cctctcccgg ccagactctg agcaggagct ccgcccccag cgcgccgccc    420

cagccccggc gccttaaaag ccgggcgcac cgccccgccg cgccctgcct gccgcacctc    480

tcctttcttc tgtagctcgc gttgaagccg cacgtccggc cccgatcccg gcaccatgag    540

cttcggctcg gagcactacc tgtgctcctc ctcctcctac cgcaaggtgt tcggggatgg    600

ctctcgcctg tccgcccgcc tctctggggc cggcggcgcg ggcggcttcc gctcgcagtc    660

gctgtcccgc agcaatgtgg cctcctcggc cgcctgctcc tcggcctcgt cgctcggcct    720

cggcctggcc tatcgccggc cgccggcgtc cgacgggctg gacctgagcc aggcggcggc    780

gcgcaccaac gagtacaaga tcatccgcac caacgagaag gagcagctgc agggcctcaa    840

cgaccgcttc gccgtgttca tcgagaaggt gcatcagctg gagacgcaga accgcgcgtt    900

ggaggccgag ctggccgcgc tgcgacagcg ccacgctgag ccgtcgcgcg tcggcgagct    960

cttccagcgc gagctgcgcg acctgcgcgc gcagctggag gaggccagct cggctcgctc   1020

gcaggccctg ctggagcgcg acgggctggc ggaggaggtg cagcggctgc gggcgcgctg   1080

cgaggaggag agccgcggac gcgaaggcgc cgagcgcgcc ctgaaggcgc agcagcgcga   1140

cgtggacggc gccacgctgg cccgcctgga cctggagaag aaggtggagt cgctgctgga   1200

cgagctggcc ttcgtacgcc aggtgcacga cgaggaggta gccgagctgc tggccacgct   1260

gcaggcgtcg tcgcaggccg cggccgaggt ggacgtgact gtggctaaac cagacctgac   1320

ctcggctctg agggagatcc gcgcccagta tgagtccctg gccgctaaga acctgcagtc   1380

cgcggaagaa tggtacaagt ccaagtttgc caacctgaac gagcaggcgg cgcgcagcac   1440

cgaggccatc cgggccagcc gcgaggagat ccacgagtat cggcgccagc tgcaggcgcg   1500

caccatcgag atcgagggcc tgcgcggggc caacgagtcc ttggagaggc agatcctgga   1560

gctggaggag cggcacagtg ccgaggtagc tggctaccag gtaagggccg gggctgggcg   1620

tggggagggg tgccctgccc tcttccgcgc gtaccctctt cctctggtaa aactgggccc   1680

caggacttaa ggggagggca aaagagagga gagaagagcc gcggctggag gcgctggtta   1740

acaaaaaacc ctggagtctt taatgttaat tttagggaac gcccctcatt tatgtccctg   1800

ccccagccct tcaaac                                                   1816
```

<210> SEQ ID NO 55
<211> LENGTH: 1934
<212> TYPE: DNA
<213> ORGANISM: Homo sapiens

<400> SEQUENCE: 55

```
aaacaccggc agtcaacagg caggcaaaga acctgggggt gggggtagca gcggtcccac     60

cctcaaaagg cccgggctgc ccagaccaag agaaagcgat gaatctcttc tggtaacgtc    120

ccttcctgtc gcatggattc aaggccgacc tgccccagca ccaccaccag cagccttctg    180

ctggggccgg cacagctggg agcaacctcc tactctcagg cagacgcgca gcaccaagca    240

gagaggcccg gtgcaggatc ccagcgccga accagcgccg gctcagtgga cgcggaaggg    300

gccggcggcc gcggccggtc ccatccccca ctgcagaccc ccagcctgtg gcggtggtcc    360
```

```
agttccgcca ggaaaccgcc gcctggagct gtgggtcgcg cacattaacg catccagcgg    420
aaaaatgaag gagacccaaa ttcaaagtta aagtaatggt gacccgagag gtgccttgat    480
gagaaggttt ggggtcccgg ttactgatgg ttatcattct tacgagatgc tggtcaccta    540
cgaagggaga aaggcacgag gagcgcctga ccaaagtggt tttgccctgc ttcccgcaag    600
aggtggcacc cacggctgga acgcaggagt cagacccaca gtccccagct ctggacgccc    660
gcagcggggc ctcgaagagg ttcagggcgg tgcccgcggc gctcgggccg ggtctcccgg    720
ggcgtggggc ggggggcggg gttgggcggc ggccggggct cctccctctt ctgccccggg    780
ctcccctgct cttaacccgc gcgcggggc gcccaggcca ctgggctccg cggagccagc    840
gagaggtctg cgcggagtct gagcggcgct cgtcccgtcc caaggccgac gccagcacgc    900
cgtcatggcc cccgcagcgg cgacgggggg cagcaccctg cccagtggct tctcggtctt    960
caccaccttg cccgacttgc tcttcatctt tgagtttgtg agtggctcct ggccggggaa   1020
gggacggggt gggctgagcc gtgcgctctc tcgggcgccc agcacagctg tcggacggga   1080
tccgctagct gcgcaggttc tgggagcatc ggggcagcag gcgcagggcg gggactaagc   1140
cagggaagtc ccctcccacc tccggtcctt tgtgcccttc tagaccaaca gaatgagggg   1200
aacagtctac aggactatgg aggaaaaact gggttcccaa ctggggtcag atgtaggcag   1260
cggggcaggg ggggacggct cttggttcgc tggtcccaaa gctgcgcgcg gggcccactt   1320
gacgcgcgca gcgccaccga agctcccgcc gcgctttgcg cggttgggta gaagtgcgca   1380
gcttttacaa gggagaaggt ttcgttaaaa aagaaaaaaa aatcagcaag agaaacatta   1440
gtattaccaa ccgagatttg gagatgagag ggagctgaat ccggtttatt ttcttctggc   1500
cttttaaagt ttctggcgag ggaacgtatt tgcgaccaat tcgatctgga aatgaggcca   1560
tcgtttgctt ggccgcagtc cttctgcccc gtgtgcgggg tgggggtgga ggagatgggg   1620
ggtgggggt gggggtggc ggcgagagcg atccgcgcgc ctcgactgac cttgggcagg   1680
cccggggcct ctgcacctgc ggtcggtccc gccttgcacg cacggtctct gcctgaggct   1740
gcaggaaagc gcttcctact gagaactcct gataagcgct cacggtgtcg cgaagccgaa   1800
gtgacctccc tcagcctcaa ctccccgggg gccgctggcc ttcacctggg aggggtgtgc   1860
cctgtatgtc ctgtgggtgc ggtccgtcac cgcctgaggg acaccttttc cggcacccca   1920
ccctcagaag tgtc                                                     1934
```

<210> SEQ ID NO 56
<211> LENGTH: 2574
<212> TYPE: DNA
<213> ORGANISM: Homo sapiens

<400> SEQUENCE: 56

```
ctggagtggg acttcatctg ggaccaaagg agggctggtg aggggagtgg caggagggag     60
gagtgcctcg gggccccgag caggatgagc ctgaggaaga gacgggtccc catgttccct    120
ttcccgctca gataatggag gtgaattgag gggagcagag acctccccac cttcagggtg    180
ggaccctgag ggaccaggac acctttgcta ggggatgtcc ctcctcactc ctgcacaagt    240
tcctcaagga caccctcggg ctccgaaaac ggggggaggg ggacgacgcc ccagaggccc    300
ctgagcccct ggttcttccc gaccctaagg gcttttctcc ctcggttccc aggcggcgac    360
ggcgggtagc gcgaagcagc aggcgcaggg gcgctgggat ggggatgtct ctgcaggtct    420
aaggttcccc ttgggagtct aaacaaagac tacggcagcg ccgtcccctc ccccgggaac    480
ccgacgccgc gcggccacag gggcctgga ggggcgggca gggcctcgca gcgcacccag    540
```

```
cacagtccgc gcggcggagc gggtgagaag tcggcggggg cgcggatcga ccggggtgtc    600

ccccaggctc cgcgtcgcgg tccccgctcg ccctcccgcc cgcccaccgg gcaccccagc    660

cgcgcagaag gcggaagcca cgcgcgaggg accgcggtcc gtccgggact agccccaggc    720

ccggcaccgc cccgcgggcc gagcgcccac acccgccaaa cccacgcggg cacgcccccg    780

cggcgcaccg cccccagccc ggcctccgcc cctgcagccg cgggcacgcg gaggggctcc    840

tggctgcccg cacctgcacc cgcgcgtcgg cggcgccgaa gccccgctcc ccgcctgcgc    900

gtctgtctcg tccgcatctc cgcggtgagt cggcggcgcc ctcgcccctg agcccagggc    960

cagcttctct cgccgccgcg gctgctgcgc gcgtccccgc ccagcccagc ccagccccga   1020

gcacgacccc agccccacgc acgaccctag ccccgcgagt cccgcaccga ctcgctcccg   1080

ccccatttcg cctccgcggg ggcggcgccc cctcctcccc gcggctcccg ctctccttcc   1140

tcgccttccc ggccgcgctg gggacccccca gccgccgtcc gcgacccccc accgcgacgc   1200

ccggaggcgg cggggtctct ttgttcgggc ggcgggcacg ggggaccacc tcccacggtg   1260

tcaccgcacc caccccgcgc ccttcctccg cctcctggag ttcaccggga ccaggtggcg   1320

gcgggtgcct ttttggggggt gcgcggccat gcaattggtg gattttttta aaccgttttg   1380

gagggggggag cgcggcgttg gggcgggag agcgctcctg gctgtgagct gctcctgccg   1440

cttcgctccg cgctctcctg ccgctccgct ccgggtctcc cgcgctcctc tccccggctc   1500

ggccgagcgc gctgccccga cgccgccacc cagagccggg ccgcgccggg cgccgagatg   1560

aaggtgctgg gacaccggct ggagctgctc acaggtaccg cccgcctgcc ccgcagccgg   1620

ccgccacttt ccgagttgga gcggactccg ggcgcggcgg ccggggactg gggcggctcg   1680

ggtctgagca ggaaggggtg cggaccccaa ctaagtccta gttttgtgct acctgtttgt   1740

gtgcggagcc cagccccggg agaggacttg aggttgtggc gagtccctgg cgctggcgtc   1800

cgggctgcgg gagcaccggt caggggggtgg ccccatgggg tctctgacca gcggagctcg   1860

gattaggacc ctgaaagcta gctcagggct cctgccctcc aatcagtgtc gcttgtcccc   1920

taagaaagga cccgtgggct tctggcagga cccgcgccat ggacctctta tttctgcgcc   1980

ctgtgacaat ctgagccgtc tttctctggg ggagaagttt cttgctggga gtggaggcga   2040

cgccaagtgg cctgggaagt gggaagccag attggaccct actgactggg gaccctcagc   2100

cttggggctc ctctggagaa gtgatcagtt gccctgctgg aaactcacat ccagggggca   2160

gtggctggag agcaagagcg aacggtcagg aagaggaggt gggaaaggga gcagggacgg   2220

gggggaggat tcgaggagtg acttctgtgt tctccccggt gtggagagac ccagacagga   2280

ggaaaggaaa gcaacccggt ttcctccagc tctgggactt ataggtgctc catccgtgta   2340

tgtcagatga gcacagattc cagtaagtgt cctccgacac ctgggggagg gggctgatca   2400

ctgccttcca ggaccttaat gtccgatgag ggagcagagc cccggagccc tgttacaagg   2460

ctggaagggg cagccgtctg tgggtgcgct caggaaacgg tggaatccga gtcgggggca   2520

gcttttgaag acctcgaaaa acaatttttg ttaatgaaga aggaggtggc atta         2574
```

<210> SEQ ID NO 57
<211> LENGTH: 1393
<212> TYPE: DNA
<213> ORGANISM: Homo sapiens

<400> SEQUENCE: 57

```
ggggggtggg tgacatatct gcaggaaatg gaacgtggaa ggcactgtct gacttggctg     60
```

cattgcccgt gtggacccgg gcgctagtgc ctgcatgtcc ctctgaccgt gtgccctctg 120
gtgtgcgctt ggatggtgtc tgccttggtg atgcctgggg ccatcaggcc agggggcggg 180
ggtgtccttg gtgagccccc gaggctgtgt gcccagtgtg cgtgccgggt ctgtgcgtgc 240
aggggctgcc gtcccagtgg gcggccgtct agcttgtttg gatggctgcg ccagtgtgat 300
gggaaggaca ggcggcctct tccttaggag ccacctcaca gttcccaggg ctctgctgcg 360
ccagccgggc agaggcaagg aggtctgggc cacacaggaa tgacagcctt tcaggcaggg 420
gtccctgctg gggaggaacg aggaggggtt gcctgcctgc cttattttgt aggtggggga 480
aggcaacgct ggagccgtga agctggcagg gctaggggac cccaggtgga gcccagggca 540
cctcctctcg ccggggcatc aggtaccccg gccccattct tcctcaggag ggagaggcag 600
gggcagactc acccccaccc ccgggcccca cacgcctgcc ctgccggttc cgcagacgat 660
aggtcacccc gcacgcacgg aggtgacgac gtcagcacct gcccgcccat gcagaccctg 720
tcccctgaat tattgatgcg gctgacaggc cgaaccacag caccaccagc accaactccc 780
acaccggcgc aaagcccggc tcaaagcccc actcccctcc agtgctcaag gtcacaggcg 840
aggggagacg gaccgaccga gaggagccgc cacagccccc tcccctgctg ccgcagtgct 900
tcccgcctgc gcctacctgg aggcggggcc ggctctgacg tcacccagag ccaatgggag 960
tgctcggccc tgagggttgg gggcctcaga gtgcaccgcg ctgtggccct tgtggggctg 1020
cccttgcgca gcgctccaag ggacggggat gtttggcttc gatcaggctg aactgagtcc 1080
tgagctctcc gcagagggtg agagaaggcg ttagggaggt tcgcagcagg gttcagcgaa 1140
ggtcactgga cttcgtagga caggtagccc ggtgacgccc aggcccagcc ccagcccttc 1200
ccatcctggg agatgagccc tagtagagcc tgatcacgtc acctcagggg gatggggaca 1260
ggggcggcca caccagggct gggagaagac agtggggcct cctcagcagc agagagcaga 1320
cacccctcac acccctcagg cggacccgca cgctgcgggt ctgggtttgg aaggcaccgc 1380
cctgggctct cga 1393

<210> SEQ ID NO 58
<211> LENGTH: 2295
<212> TYPE: DNA
<213> ORGANISM: Homo sapiens

<400> SEQUENCE: 58
ctccttcctt cacaccttcc ttcggaaacg tctgctcctg acaaggtcta cttcctgctc 60
tcaggaggcc cttattgtgg aggaagggag gcgtcgcccg tccctggctt ctctgacagc 120
cgtgttccat ccccgccctg tgccccttct cccggacagt gccttctcca gggctcaccc 180
aggagggtgc agcggtggcc cccggggcgg tggtcgtggt gggggtgtta gctgcagggg 240
tgccctcggt gggtgggagt tggtggcctc tcgctggtgc catgggactc gcatgttcgc 300
cctgcgcccc tcggctcttg agcccacagg ccgggatcct gcctgccagc cgcgtgcgct 360
gccgtttaac ccttgcaggc gcagagcgcg cggcggcggt gacagagaac tttgtttggc 420
tgcccaaata cagcctcctg cagaaggacc ctgcgcccgg ggaaggggag gaatctcttc 480
ccctctgggc gcccgccctc ctcgccatgg cccggcctcc acatccgccc acatctggcc 540
gcagcggggc gcccgggggg aggggctgag gccgcgtctc tcgccgtccc ctgggcgcgg 600
gccaggcggg gaggaggggg gcgctccggt cgtgtgccca ggactgtccc ccagcggcca 660
ctcgggcccc agccccccag gcctggcctt gacaggcggg cggagcagcc agtgcgagac 720
agggaggccg gtgcgggtgc gggaacctga tccgcccggg aggcgggggc ggggcggggg 780

```
cgcagcgcgc ggggaggggc cggcgcccgc cttcctcccc cattcattca gctgagccag    840

ggggcctagg ggctcctccg gcggctagct ctgcactgca ggagcgcggg cgcggcgccc    900

cagccagcgc gcagggcccg ggccccgccg ggggcgcttc ctcgccgctg ccctccgcgc    960

gacccgctgc ccaccagcca tcatgtcgga ccccgcggtc aacgcgcagc tggatgggat   1020

catttcggac ttcgaaggtg ggtgctgggc tggctgctgc ggccgcggac gtgctggaga   1080

ggaccctgcg ggtgggcctg gcgcgggacg gggtgcgct gaggggagac gggagtgcgc    1140

tgaggggaga cgggacccct aatccaggcg ccctcccgct gagagcgccg cgcgcccccg   1200

gccccgtgcc cgcgccgcct acgtggggga ccctgttagg ggcacccgcg tagaccctgc   1260

gcgccctcac aggaccctgt gctcgttctg cgcactgccg cctgggtttc cttcctttta   1320

ttgttgtttg tgtttgccaa gcgacagcga cctcctcgag ggctcgcgag gctgcctcgg   1380

aactctccag gacgcacagt ttcactctgg gaaatccatc ggtcccctcc ctttggctct   1440

ccccggcggc tctcgggccc cgcttggacc cggcaacggg atagggaggt cgttcctcac   1500

ctccgactga gtggacagcc gcgtcctgct cgggtggaca gccctcccct cccccacgcc   1560

agtttcgggg ccgccaagtt gtgcagcccg tgggccggga gcaccgaacg gacacagccc   1620

aggtcgtggc agggtctaga gtgggatgtc ccatggcccc catccaggcc tggggatatc   1680

ctcatccgcc tcccagaatc gggccgtggg ggacagaagg ggcctgcgtg cgggcaggga   1740

gagtattttg gctctctcct gtcttcgggg tttacaaagt gtgttgggac ttgcggggct   1800

gctctgtcca agcctgggtc tggcgtccgc gtctctgagc ctgtgagtgc gtgcgctttc   1860

ctgcgtcctc ttgactgccg gtgctggggc tctgcgtcct gcgtccgcgg gagtaaatac   1920

agcaggcgaa ggggaagctc acacaatggt ctccagcgct ctggggcagg gcttctgagg   1980

ggcgggcctg cctctgccgg gacctggagc ccccgcccct cggagaggct cctaggctga   2040

cttgggcaga gccctctggt gggccgggag ggggaaaggc tgtgttgaaa tgagcaaact   2100

gtccaggtgt caggccaagc tgggaggtga ccagcctgag gtcctccccg ctccatggcc   2160

agaaccaggg ctgacatctg ggtgtcctga gcccagctgc ccacacggcc cacctggggt   2220

cagccctatc tgagtggggg aggcggggcc tcctggggga ccagaacttt ggctggacgc   2280

caagcagagt gccag                                                    2295
```

<210> SEQ ID NO 59
<211> LENGTH: 1404
<212> TYPE: DNA
<213> ORGANISM: Homo sapiens

<400> SEQUENCE: 59

```
agaagggaat atcagaagca ggacgaaagc caggtcaagt ctctttcctt aggctcccca     60

aagggacaag tactcacctc ccagagacct ggcccagcgg gtcctcatgg cagcaccacc    120

ccctcccggt gcccacgacc attcgtctcc catccggcgt tctccaggat ttccaaagac    180

gcccgtttag atccacaggt acttacctga gtccctctgc ttctccacaa ctccgactcc    240

tccccgcctc tctctttttt taaaaaaaaa atttaaacaa ttcccaaata atatttaata    300

ggaaagaaga aggaaaagga gcgcacagga agggcggagg cggcacccgg gggggactgt    360

ccccagagga ggccgctgtg agccggcgac gcgaggctgg gggagtggga ggcaaacccg    420

ctaacctgtc gtcgaatggc cactcccagt tctccgctca cgagggtgga aaggcagaag    480

gcttgaaggc aaggcgtgag ggagcgccca ggacgctctc ggaggggccg ggccggggtc    540
```

```
tgcgctgcag cccgcacgca cctcacttcc gcgtcgcggc gctcggtcgc tcgccccctc    600

tcttgggccc cttctggtcg tcgccgtcct cctcctccta gtcctcctcc ttctccttct    660

cctcggctct ccgcccccac cgctgatttg tcagcgcttc tgcccgcccc tctcccggcg    720

ctcgctgctt tccctgcagc gtgctcctcg tccctatctc ggatggggat ggggcagggg    780

gcgcggggtg agccatcaac tccagccgcc tgcctggccg cgcaaggcgg gaaagtgggg    840

gcgcttttgc gcctcacgtt aagtttaggg tcacgagcac tcttgtggag atcgggagcg    900

gttgggctag ggatgatgcc tcttcctctt tccccttccc ctcccttctt gtccccgcct    960

ttcctctggg tcctcccggg gaccaccccc taccccctcgt cagagtcgcc ctgggagagc   1020

cgagggcctg agggtcgacc accaagggca gagcctatcc cttggggagc tgctggagga   1080

gacaggcagc gccgggaggt ggctcacacc gcaccgccga gagcgctttg ccctcgcatc   1140

gctgaaattt aatcacggtc acaggttaca acgttagggg tcgctttagt tcaaatatct   1200

tcaaggtttt cgtttgctct taatctagga agagccggaa agggtcctga gggtgaaagg   1260

gagactacta aggaagagtc acaggttgag gaggcaggag aaggctcagc aaatcctctt   1320

tccacgccac tatcaccatt ttcctttcca ccaatcagcg cctgccagac gctgattttc   1380

ccatcagtgg aacaaggaat aaat                                           1404
```

```
<210> SEQ ID NO 60
<211> LENGTH: 1756
<212> TYPE: DNA
<213> ORGANISM: Homo sapiens

<400> SEQUENCE: 60

caaaggctgt aacaacctgg aacgcaaatt cgttaaatta tgatacaata aggccaacct     60

cgaggatcct cggtggacta ctagcgcact tccttacaat tagaaagtga aaaactgggt    120

cagccctaga gtcacgcaat aatgctgcgt cacgaaactg cgcattccaa gagaaacttt    180

tctcaggccc agaattaagt cggagggatc cgccgcgcag ctcaatccct aggaagcatg    240

aaagaatgta ttgtaaagag taaaatcacg cgcaatccat cccaatataa ccgcagttgt    300

tcgtgggcct tcttgcagag aaaggctgcc caaccttgac ggggccatgg gcgctgcggg    360

agggcaaaag accacagaga tctgcgaagc caaagtaaac aacggggttg gggcggcgag    420

aatgatcaat agcgatgctc cgaaaggact ccgcgatagg aatcgagcgg gaaggattcc    480

ctccatccta acagtccatg ggttaagagg ccgaagcttc cctaaatacc acactcccgc    540

gagagaaggg actgagaaca acttctcaaa ctattctctc tcgaaatcgc tcccttcctc    600

gaaaattcca tctctgagac tcggatgagg tccccacccc ctccaccctt gtcccgtgac    660

cgtcgcccgc tcagcctccc agccgagtcc gcggggcctg gggcgcccac cccgcccacc    720

caagggaccg cgcaggggtg aactccccccg cgccccacct gcgccttcca gacctcgggc    780

gccccggcgt tgcctcgaga gctccctgcg cggccgccgc ggcacggacc agctcccact    840

cccttacact gggcgccgct gcgctcgccg ggggccggtc ccgaggttcc caaggcctcg    900

cgcgcgcgct tgccgtggca accaagacgt tccacgacgc gcgctctcga acgcttcgcg    960

tcacgcggcc gcgcggcccc gcccgtcggc ctcgctcccg ccacagagcc cgcagcacgc   1020

cgccgccgca gcctaggtca cgtgagtacc cacgcgcgcg tcttgccagc ggattcatca   1080

ccggcctgct cagactaggt tctgcccact ctgaccttct aaatggtacg tgggaggacg   1140

tccgtcccct tcggacccaa gagtcaccgt aacactctag aaggggagaa aaggagcgag   1200

ggcggcaggc gacagagaac ctcgcgagtc agcggccccg cgcagacccc cccaggcacg   1260
```

```
gtcccctgcg gccacgtcgg ctgctcggcg cctgcgcaat ctctttctct ccagcgaaac   1320

cgaggcctcc ggagagccta gtagagagtg tgggcagtga gcgcttgtag ccgctagagg   1380

gagcgctggg cacagtgcac gagagacaat aaaggctgat tatcccctca atgtctctgc   1440

agcctgagct ttgtgacttc tgtatccaga gcacagttaa tttccaaaag cccgcctgca   1500

ccacgtgttt taagtcttgg tgtgtgtgta aagtctatat cactatcata aaactgttag   1560

ttcctgattc cgggatacaa agagtaaaat caagatgaac atactttacc cttcttgaca   1620

agtgttttta aattagtaaa atattgtaga tgacagactc ttcaataggg ctgccttagg   1680

gaaaaaaaaa cagaaaaaag aaaaagcagt atgtacttgc ccggagcatt tagaaccagt   1740

tttgttgttg ttgtgt                                                   1756
```

<210> SEQ ID NO 61
<211> LENGTH: 24
<212> TYPE: RNA
<213> ORGANISM: Artificial
<220> FEATURE:
<223> OTHER INFORMATION: Target specific sequence of the Cpf1-C9orf72-crRNA#1

<400> SEQUENCE: 61
ccguaagaca cuguuaagug cauu 24

<210> SEQ ID NO 62
<211> LENGTH: 24
<212> TYPE: RNA
<213> ORGANISM: Artificial
<220> FEATURE:
<223> OTHER INFORMATION: Target specific sequence of the Cpf1-C9orf72-crRNA#2

<400> SEQUENCE: 62
uauucagaaa caggagggag gucc 24

<210> SEQ ID NO 63
<211> LENGTH: 24
<212> TYPE: RNA
<213> ORGANISM: Artificial
<220> FEATURE:
<223> OTHER INFORMATION: Target specific sequence of the Cpf1-CNRIP1-crRNA#1

<400> SEQUENCE: 63
gcuuguauuc cuccauucuc gcuu 24

<210> SEQ ID NO 64
<211> LENGTH: 24
<212> TYPE: RNA
<213> ORGANISM: Artificial
<220> FEATURE:
<223> OTHER INFORMATION: Target specific sequence of the Cpf1-CNRIP1-crRNA#2

<400> SEQUENCE: 64
cacagauuuu gaagggugag cuau 24

<210> SEQ ID NO 65
<211> LENGTH: 24
<212> TYPE: RNA
<213> ORGANISM: Artificial
<220> FEATURE:
<223> OTHER INFORMATION: Target specific sequence of the Cpf1-DMPK-crRNA#1

<400> SEQUENCE: 65
uugugcauga cgcccugcuc uggg 24

<210> SEQ ID NO 66
<211> LENGTH: 24
<212> TYPE: RNA
<213> ORGANISM: Artificial
<220> FEATURE:
<223> OTHER INFORMATION: Target specific sequence of the Cpf1-DMPK-crRNA#2

<400> SEQUENCE: 66
cugcuggccu cuccagccuu cuca 24

<210> SEQ ID NO 67
<211> LENGTH: 24
<212> TYPE: RNA
<213> ORGANISM: Artificial
<220> FEATURE:
<223> OTHER INFORMATION: Target specific sequence of the Cpf1-EGFR-crRNA#1

<400> SEQUENCE: 67
gagaggcuaa gugucccacu gccc 24

<210> SEQ ID NO 68
<211> LENGTH: 24
<212> TYPE: RNA
<213> ORGANISM: Artificial
<220> FEATURE:
<223> OTHER INFORMATION: Target specific sequence of the Cpf1-EGFR-crRNA#2

<400> SEQUENCE: 68
agccaaccaa aauauuaaac cugu 24

<210> SEQ ID NO 69
<211> LENGTH: 24
<212> TYPE: RNA
<213> ORGANISM: Artificial
<220> FEATURE:
<223> OTHER INFORMATION: Target specific sequence of the Cpf1-FBN1-crRNA#1

<400> SEQUENCE: 69
ugccccaaag gagaggacgu gguu 24

<210> SEQ ID NO 70
<211> LENGTH: 24
<212> TYPE: RNA
<213> ORGANISM: Artificial
<220> FEATURE:
<223> OTHER INFORMATION: Target specific sequence of the Cpf1-FBN1-crRNA#2

<400> SEQUENCE: 70
guggcuuuga aagguauagu auuu 24

<210> SEQ ID NO 71
<211> LENGTH: 24
<212> TYPE: RNA
<213> ORGANISM: Artificial
<220> FEATURE:
<223> OTHER INFORMATION: Target specific sequence of the Cpf1-HTT-crRNA#1

<400> SEQUENCE: 71
ugggagugca ccccugcucu gacc 24

<210> SEQ ID NO 72
<211> LENGTH: 24
<212> TYPE: RNA
<213> ORGANISM: Artificial
<220> FEATURE:
<223> OTHER INFORMATION: Target specific sequence of the Cpf1-HTT-crRNA#2

<400> SEQUENCE: 72
ggcccgcugc agcucccugu cccg 24

<210> SEQ ID NO 73
<211> LENGTH: 24
<212> TYPE: RNA
<213> ORGANISM: Artificial
<220> FEATURE:
<223> OTHER INFORMATION: Target specific sequence of the Cpf1-INA-crRNA#1

<400> SEQUENCE: 73
caguuacagu gaggaccugc agag 24

<210> SEQ ID NO 74
<211> LENGTH: 24
<212> TYPE: RNA
<213> ORGANISM: Artificial
<220> FEATURE:
<223> OTHER INFORMATION: Target specific sequence of the Cpf1-INA-crRNA#2

<400> SEQUENCE: 74
ugucccugcc ccagcccuuc aaac 24

<210> SEQ ID NO 75
<211> LENGTH: 24
<212> TYPE: RNA
<213> ORGANISM: Artificial
<220> FEATURE:
<223> OTHER INFORMATION: Target specific sequence of the Cpf1-MAL-crRNA#1

<400> SEQUENCE: 75
ccugccuguu gacugccggu guuu 24

<210> SEQ ID NO 76
<211> LENGTH: 24
<212> TYPE: RNA
<213> ORGANISM: Artificial
<220> FEATURE:
<223> OTHER INFORMATION: Target specific sequence of the Cpf1-MAL-crRNA#2

<400> SEQUENCE: 76
cggcacccca cccucagaag uguc 24

<210> SEQ ID NO 77
<211> LENGTH: 24
<212> TYPE: RNA
<213> ORGANISM: Artificial
<220> FEATURE:
<223> OTHER INFORMATION: Target specific sequence of the Cpf1-NDRG4.1-crRNA#1

<400> SEQUENCE: 77
gucccagaug aagucccacu ccag 24

<210> SEQ ID NO 78
<211> LENGTH: 24
<212> TYPE: RNA
<213> ORGANISM: Artificial
<220> FEATURE:
<223> OTHER INFORMATION: Target specific sequence of the Cpf1-NDRG4.1-crRNA#2

<400> SEQUENCE: 78
uuaaugaaga aggagguggc auua 24

<210> SEQ ID NO 79
<211> LENGTH: 24
<212> TYPE: RNA
<213> ORGANISM: Artificial
<220> FEATURE:
<223> OTHER INFORMATION: Target specific sequence of the Cpf1-NDRG4.2-crRNA#1

<400> SEQUENCE: 79
cugcagauau gucacccacc cccc 24

<210> SEQ ID NO 80
<211> LENGTH: 24
<212> TYPE: RNA
<213> ORGANISM: Artificial
<220> FEATURE:
<223> OTHER INFORMATION: Target specific sequence of the Cpf1-NDRG4.2-crRNA#2

<400> SEQUENCE: 80
gaaggcaccg cccugggcuc ucga 24

<210> SEQ ID NO 81
<211> LENGTH: 24
<212> TYPE: RNA
<213> ORGANISM: Artificial
<220> FEATURE:
<223> OTHER INFORMATION: Target specific sequence of the Cpf1-SEPT9.1-crRNA#1

<400> SEQUENCE: 81
cgaaggaagg ugugaaggaa ggag 24

<210> SEQ ID NO 82
<211> LENGTH: 24
<212> TYPE: RNA
<213> ORGANISM: Artificial
<220> FEATURE:
<223> OTHER INFORMATION: Target specific sequence of the Cpf1-SEPT9.1-crRNA#2

<400> SEQUENCE: 82
gcuggacgcc aagcagagug ccag 24

<210> SEQ ID NO 83
<211> LENGTH: 24
<212> TYPE: RNA
<213> ORGANISM: Artificial
<220> FEATURE:
<223> OTHER INFORMATION: Target specific sequence of the Cpf1-FMR1-crRNA#1

<400> SEQUENCE: 83
cauuccacug ugaaacaaac cuca 24

<210> SEQ ID NO 84
<211> LENGTH: 24
<212> TYPE: RNA
<213> ORGANISM: Artificial
<220> FEATURE:
<223> OTHER INFORMATION: Target specific sequence of the Cpf1-FMR1-crRNA#2

<400> SEQUENCE: 84
cggucuagca uugggacuuc ggag 24

<210> SEQ ID NO 85
<211> LENGTH: 24
<212> TYPE: RNA
<213> ORGANISM: Artificial
<220> FEATURE:
<223> OTHER INFORMATION: Target specific sequence of the Cpf1-SNCA-crRNA#1

<400> SEQUENCE: 85
guccugcuuc ugauauuccc uucu 24

<210> SEQ ID NO 86
<211> LENGTH: 24
<212> TYPE: RNA
<213> ORGANISM: Artificial
<220> FEATURE:
<223> OTHER INFORMATION: Target specific sequence of the Cpf1-SNCA-crRNA#2

<400> SEQUENCE: 86
ccaucagugg aacaaggaau aaau 24

<210> SEQ ID NO 87
<211> LENGTH: 24
<212> TYPE: RNA
<213> ORGANISM: Artificial
<220> FEATURE:
<223> OTHER INFORMATION: Target specific sequence of the Cpf1-SPG20-crRNA#1

<400> SEQUENCE: 87
cguuccaggu uguuacagcc uuug 24

<210> SEQ ID NO 88
<211> LENGTH: 24
<212> TYPE: RNA
<213> ORGANISM: Artificial
<220> FEATURE:
<223> OTHER INFORMATION: Target specific sequence of the Cpf1-SPG20-crRNA#2

<400> SEQUENCE: 88
gaaccaguuu uguuguuguu gugu 24

<210> SEQ ID NO 89
<211> LENGTH: 20
<212> TYPE: RNA
<213> ORGANISM: Artificial
<220> FEATURE:
<223> OTHER INFORMATION: Target specific sequence of the Cas9 gRNA-FMR1#1 (FMR1)

<400> SEQUENCE: 89
cagacugcgc uacuuugaac 20

<210> SEQ ID NO 90
<211> LENGTH: 20
<212> TYPE: RNA
<213> ORGANISM: Artificial
<220> FEATURE:
<223> OTHER INFORMATION: Target specific sequence of the Cas9 gRNA-
FMR1#2 (FMR1)

<400> SEQUENCE: 90
gcgcuagggc cucucggagu 20

<210> SEQ ID NO 91
<211> LENGTH: 20
<212> TYPE: RNA
<213> ORGANISM: Artificial
<220> FEATURE:
<223> OTHER INFORMATION: Target specific sequence of the Cas9-CNRIP1-
crRNA#1

<400> SEQUENCE: 91
cuccaacccc cgggcccgcu 20

<210> SEQ ID NO 92
<211> LENGTH: 20
<212> TYPE: RNA
<213> ORGANISM: Artificial
<220> FEATURE:
<223> OTHER INFORMATION: Target specific sequence of the Cas9-CNRIP1-
crRNA#4

<400> SEQUENCE: 92
aaauuuaaau caccggcuag 20

<210> SEQ ID NO 93
<211> LENGTH: 20
<212> TYPE: RNA
<213> ORGANISM: Artificial
<220> FEATURE:
<223> OTHER INFORMATION: Target specific sequence of the Cas9-MAL-
crRNA#1

<400> SEQUENCE: 93
gggagcaacc uccuacucuc 20

<210> SEQ ID NO 94
<211> LENGTH: 20
<212> TYPE: RNA
<213> ORGANISM: Artificial
<220> FEATURE:
<223> OTHER INFORMATION: Target specific sequence of the Cas9-MAL-
crRNA#4

<400> SEQUENCE: 94
cgacaccgug agcgcuuauc 20

<210> SEQ ID NO 95
<211> LENGTH: 20
<212> TYPE: RNA
<213> ORGANISM: Artificial
<220> FEATURE:
<223> OTHER INFORMATION: Target specific sequence of the Cas9-HTT-
crRNA#2

<400> SEQUENCE: 95
acuaaucaca gugccucugu 20

<210> SEQ ID NO 96
<211> LENGTH: 20
<212> TYPE: RNA
<213> ORGANISM: Artificial
<220> FEATURE:
<223> OTHER INFORMATION: Target specific sequence of the Cas9-HTT-crRNA#3

<400> SEQUENCE: 96
agcagcggcu gugccugcgg 20

<210> SEQ ID NO 97
<211> LENGTH: 20
<212> TYPE: RNA
<213> ORGANISM: Artificial
<220> FEATURE:
<223> OTHER INFORMATION: Target specific sequence of the Cas9-SNCA-crRNA#1

<400> SEQUENCE: 97
agacgcccgu uuagauccac 20

<210> SEQ ID NO 98
<211> LENGTH: 20
<212> TYPE: RNA
<213> ORGANISM: Artificial
<220> FEATURE:
<223> OTHER INFORMATION: Target specific sequence of the Cas9-SNCA-crRNA#3

<400> SEQUENCE: 98
ggugauagug gcguggaaag 20

<210> SEQ ID NO 99
<211> LENGTH: 20
<212> TYPE: RNA
<213> ORGANISM: Artificial
<220> FEATURE:
<223> OTHER INFORMATION: Target specific sequence of the Cas9-EGFR-crRNA#1

<400> SEQUENCE: 99
cugucucugc acccggaguu 20

<210> SEQ ID NO 100
<211> LENGTH: 20
<212> TYPE: RNA
<213> ORGANISM: Artificial
<220> FEATURE:
<223> OTHER INFORMATION: Target specific sequence of the Cas9-EGFR-crRNA#3

<400> SEQUENCE: 100
agccccauuu ugaaacacca 20

<210> SEQ ID NO 101
<211> LENGTH: 20
<212> TYPE: RNA
<213> ORGANISM: Artificial
<220> FEATURE:
<223> OTHER INFORMATION: Target specific sequence of the Cas9-C9orf72-crRNA#1

<400> SEQUENCE: 101
gcgccaacgc uccuccagag 20

<210> SEQ ID NO 102
<211> LENGTH: 20
<212> TYPE: RNA
<213> ORGANISM: Artificial
<220> FEATURE:
<223> OTHER INFORMATION: Target specific sequence of the Cas9-C9orf72-crRNA#3

<400> SEQUENCE: 102
cucggagcug ugaagcaacc 20

<210> SEQ ID NO 103
<211> LENGTH: 20
<212> TYPE: RNA
<213> ORGANISM: Artificial
<220> FEATURE:
<223> OTHER INFORMATION: Target specific sequence of the Cas9-INA-crRNA#2

<400> SEQUENCE: 103
agaagagggg auagggucaa 20

<210> SEQ ID NO 104
<211> LENGTH: 20
<212> TYPE: RNA
<213> ORGANISM: Artificial
<220> FEATURE:
<223> OTHER INFORMATION: Target specific sequence of the Cas9-INA-crRNA#3

<400> SEQUENCE: 104
cuggggccca guuuuaccag 20

<210> SEQ ID NO 105
<211> LENGTH: 20
<212> TYPE: RNA
<213> ORGANISM: Artificial
<220> FEATURE:
<223> OTHER INFORMATION: Target specific sequence of the Cas9-SPG20-crRNA#1

<400> SEQUENCE: 105
caauuagaaa gugaaaaacu 20

<210> SEQ ID NO 106
<211> LENGTH: 20
<212> TYPE: RNA
<213> ORGANISM: Artificial
<220> FEATURE:
<223> OTHER INFORMATION: Target specific sequence of the Cas9-SPG20-crRNA#3

<400> SEQUENCE: 106
acaccaagac uuaaaacacg 20

<210> SEQ ID NO 107
<211> LENGTH: 20
<212> TYPE: RNA
<213> ORGANISM: Artificial
<220> FEATURE:
<223> OTHER INFORMATION: Target specific sequence of the Cas9-FBN1-crRNA#2

<400> SEQUENCE: 107
uaguuuaacc acgaacgggg 20

<210> SEQ ID NO 108

<211> LENGTH: 20
<212> TYPE: RNA
<213> ORGANISM: Artificial
<220> FEATURE:
<223> OTHER INFORMATION: Target specific sequence of the Cas9-FBN1-crRNA#4

<400> SEQUENCE: 108
augaacccca gucuuaaucu 20

<210> SEQ ID NO 109
<211> LENGTH: 20
<212> TYPE: RNA
<213> ORGANISM: Artificial
<220> FEATURE:
<223> OTHER INFORMATION: Target specific sequence of the Cas9-NDRG4.1-crRNA#2

<400> SEQUENCE: 109
cuuucccgcu cagauaaugg 20

<210> SEQ ID NO 110
<211> LENGTH: 20
<212> TYPE: RNA
<213> ORGANISM: Artificial
<220> FEATURE:
<223> OTHER INFORMATION: Target specific sequence of the Cas9-NDRG4.1-crRNA#4

<400> SEQUENCE: 110
cccccucccc caggugucgg 20

<210> SEQ ID NO 111
<211> LENGTH: 20
<212> TYPE: RNA
<213> ORGANISM: Artificial
<220> FEATURE:
<223> OTHER INFORMATION: Target specific sequence of the Cas9-NDRG4.2-crRNA#2

<400> SEQUENCE: 111
gccaucaggc cagggggcgg 20

<210> SEQ ID NO 112
<211> LENGTH: 20
<212> TYPE: RNA
<213> ORGANISM: Artificial
<220> FEATURE:
<223> OTHER INFORMATION: Target specific sequence of the Cas9-NDRG4.2-crRNA#4

<400> SEQUENCE: 112
gacgugauca ggcucuacua 20

<210> SEQ ID NO 113
<211> LENGTH: 20
<212> TYPE: RNA
<213> ORGANISM: Artificial
<220> FEATURE:
<223> OTHER INFORMATION: Target specific sequence of the Cas9-SEPT9.1-crRNA#1

<400> SEQUENCE: 113
ucaggaggcc cuuauugugg 20

<210> SEQ ID NO 114
<211> LENGTH: 20

<212> TYPE: RNA
<213> ORGANISM: Artificial
<220> FEATURE:
<223> OTHER INFORMATION: Target specific sequence of the Cas9-SEPT9.1-crRNA#4

<400> SEQUENCE: 114
guucuggcca uggagcgggg 20

<210> SEQ ID NO 115
<211> LENGTH: 20
<212> TYPE: RNA
<213> ORGANISM: Artificial
<220> FEATURE:
<223> OTHER INFORMATION: Target specific sequence of the Cas9-DMPK-crRNA#2

<400> SEQUENCE: 115
uccacgucag ggccucagcc 20

<210> SEQ ID NO 116
<211> LENGTH: 20
<212> TYPE: RNA
<213> ORGANISM: Artificial
<220> FEATURE:
<223> OTHER INFORMATION: Target specific sequence of the Cas9-DMPK-crRNA#3

<400> SEQUENCE: 116
ggaucauugc aggagcuaug 20

<210> SEQ ID NO 117
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (C9orf72-left)

<400> SEQUENCE: 117
gatgcgctga gggttcgtgt gtttttgaat gcacttaaca gtgtctt 47

<210> SEQ ID NO 118
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (C9orf72-right)

<400> SEQUENCE: 118
ccattgtctt atgaggccca gggtgcagga cctccctcct gtttctg 47

<210> SEQ ID NO 119
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (CNRIP1-left)

<400> SEQUENCE: 119
gatgcgctga gggttcgtgt gtgagggaag cgagaatgga ggaatac 47

<210> SEQ ID NO 120
<211> LENGTH: 47
<212> TYPE: DNA

<213> ORGANISM: Artificial
<220> FEATURE:
<223> OTHER INFORMATION: Target Specific sequence for oligo binding (20bp of the Cpf1-crRNA + 5bp) (CNRIP1-right)

<400> SEQUENCE: 120
ccattgtctt atgaggccca ggggttaata gctcaccctt caaaatc 47

<210> SEQ ID NO 121
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (DMPK-left)

<400> SEQUENCE: 121
gatgcgctga gggttcgtgt gtcgctcccc agagcagggc gtcatgc 47

<210> SEQ ID NO 122
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (DMPK-right)

<400> SEQUENCE: 122
ccattgtctt atgaggccca ggattcctga gaaggctgga gaggcca 47

<210> SEQ ID NO 123
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (EGFR-left)

<400> SEQUENCE: 123
gatgcgctga gggttcgtgt gttacagggg cagtgggaca cttagcc 47

<210> SEQ ID NO 124
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (EGFR-right)

<400> SEQUENCE: 124
ccattgtctt atgaggccca gggtaagaca ggtttaatat tttggtt 47

<210> SEQ ID NO 125
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (FBN1-left)

<400> SEQUENCE: 125
gatgcgctga gggttcgtgt gtcatttaac cacgtcctct cctttgg 47

<210> SEQ ID NO 126
<211> LENGTH: 47
<212> TYPE: DNA
<213> ORGANISM: Artificial

<220> FEATURE:
<223> OTHER INFORMATION: Target Specific sequence for oligo binding (20bp of the Cpf1-crRNA + 5bp) (FEN1-right)

<400> SEQUENCE: 126
ccattgtctt atgaggccca gggccacaaa tactatacct ttcaaag 47

<210> SEQ ID NO 127
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (FMR1-left)

<400> SEQUENCE: 127
gatgcgctga gggttcgtgt gtaaagttga ggtttgtttc acagtgg 47

<210> SEQ ID NO 128
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (FMR1-right)

<400> SEQUENCE: 128
ccattgtctt atgaggccca gggagctctc cgaagtccca atgctag 47

<210> SEQ ID NO 129
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (HTT-left)

<400> SEQUENCE: 129
gatgcgctga gggttcgtgt gtcggaaggt cagagcaggg gtgcact 47

<210> SEQ ID NO 130
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (HTT-right)

<400> SEQUENCE: 130
ccattgtctt atgaggccca ggcccgccgg gacagggagc tgcagcg 47

<210> SEQ ID NO 131
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (INA-left)

<400> SEQUENCE: 131
gatgcgctga gggttcgtgt gtgctcgctc tgcaggtcct cactgta 47

<210> SEQ ID NO 132
<211> LENGTH: 47
<212> TYPE: DNA
<213> ORGANISM: Artificial
<220> FEATURE:

<223> OTHER INFORMATION: Target Specific sequence for oligo binding (20bp of the Cpf1-crRNA + 5bp) (INA-right)

<400> SEQUENCE: 132
ccattgtctt atgaggccca ggtctttgtt tgaagggctg gggcagg 47

<210> SEQ ID NO 133
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (MAL-left)

<400> SEQUENCE: 133
gatgcgctga gggttcgtgt gtacatgaaa caccggcagt caacagg 47

<210> SEQ ID NO 134
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (MAL-right)

<400> SEQUENCE: 134
ccattgtctt atgaggccca ggacgctgac acttctgagg gtggggt 47

<210> SEQ ID NO 135
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (NDRG4.1-left)

<400> SEQUENCE: 135
gatgcgctga gggttcgtgt gtactccctg gagtgggact tcatctg 47

<210> SEQ ID NO 136
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (NDRG4.1-right)

<400> SEQUENCE: 136
ccattgtctt atgaggccca ggacccataa tgccacctcc ttcttca 47

<210> SEQ ID NO 137
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (NDRG4.2-left)

<400> SEQUENCE: 137
gatgcgctga gggttcgtgt gttggttggg gggtgggtga catatct 47

<210> SEQ ID NO 138
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (NDRG4.2-right)

<400> SEQUENCE: 138
ccattgtctt atgaggccca ggagacgtcg agagcccagg gcggtgc 47

<210> SEQ ID NO 139
<211> LENGTH: 47
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (SEPT9.1-left)

<400> SEQUENCE: 139
gatgcgctga gggttcgtgt gtcctagctc cttccttcac accttcc 47

<210> SEQ ID NO 140
<211> LENGTH: 47
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (SEPT9.1-right)

<400> SEQUENCE: 140
ccattgtctt atgaggccca ggagccactg gcactctgct tggcgtc 47

<210> SEQ ID NO 141
<211> LENGTH: 47
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (SEPT9.2-left)

<400> SEQUENCE: 141
gatgcgctga gggttcgtgt gtcagccagc aagcacctgg ggtagag 47

<210> SEQ ID NO 142
<211> LENGTH: 47
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (SEPT9.2-right)

<400> SEQUENCE: 142
ccattgtctt atgaggccca ggggtgataa cttgagcgga gtgattt 47

<210> SEQ ID NO 143
<211> LENGTH: 47
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (SNCA-left)

<400> SEQUENCE: 143
gatgcgctga gggttcgtgt gttgtggaga agggaatatc agaagca 47

<210> SEQ ID NO 144
<211> LENGTH: 47
<212> TYPE: DNA
<213> ORGANISM: Artificial
<220> FEATURE:
<223> OTHER INFORMATION: Target Specific sequence for oligo binding
(20bp of the Cpf1-crRNA + 5bp) (SNCA-right)

<400> SEQUENCE: 144
ccattgtctt atgaggccca ggggaatatt tattccttgt tccactg 47

<210> SEQ ID NO 145
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (SPG20-left)

<400> SEQUENCE: 145
gatgcgctga gggttcgtgt gttatttcaa aggctgtaac aacctgg 47

<210> SEQ ID NO 146
<211> LENGTH: 47
<212> TYPE: DNA
<213> ORGANISM: Artificial
<220> FEATURE:
<223> OTHER INFORMATION: Target Specific sequence for oligo binding (20bp of the Cpf1-crRNA + 5bp) (SPG20-right)

<400> SEQUENCE: 146
ccattgtctt atgaggccca ggcaaaaaca caacaacaac aaaactg 47

<210> SEQ ID NO 147
<211> LENGTH: 41
<212> TYPE: DNA
<213> ORGANISM: Artificial
<220> FEATURE:
<223> OTHER INFORMATION: Oligonucleotide PS1455 (Loop for SEPT9.1)

<400> SEQUENCE: 147
ggtacggtct cacgctagcc actggcactc tgcttggcgt c 41

<210> SEQ ID NO 148
<211> LENGTH: 41
<212> TYPE: DNA
<213> ORGANISM: Artificial
<220> FEATURE:
<223> OTHER INFORMATION: Oligonucleotide PS1456 (3'-Phosphate surface for SEPT9.1)

<400> SEQUENCE: 148
ggtacggtct caattcccta gctccttcct tcacaccttc c 41

<210> SEQ ID NO 149
<211> LENGTH: 35
<212> TYPE: DNA
<213> ORGANISM: Artificial
<220> FEATURE:
<223> OTHER INFORMATION: Oligonucleotide PS1457 (5'-Biotin for SEPT9.1)

<400> SEQUENCE: 149
catcgatctg atgcagtcta cttcctgctc tcagg 35

<210> SEQ ID NO 150
<211> LENGTH: 41
<212> TYPE: DNA
<213> ORGANISM: Artificial
<220> FEATURE:
<223> OTHER INFORMATION: Oligonucleotide PS1458 (Loop for SEPT9.2)

<400> SEQUENCE: 150
ggtacggtct cacgctggtg ataacttgag cggagtgatt t 41

<210> SEQ ID NO 151
<211> LENGTH: 41
<212> TYPE: DNA
<213> ORGANISM: Artificial
<220> FEATURE:
<223> OTHER INFORMATION: Oligonucleotide PS1459 (3'-Phosphate surface for SEPT9.2)

<400> SEQUENCE: 151
ggtacggtct caattccagc cagcaagcac ctggggtaga g 41

<210> SEQ ID NO 152
<211> LENGTH: 36
<212> TYPE: DNA
<213> ORGANISM: Artificial
<220> FEATURE:
<223> OTHER INFORMATION: Oligonucleotide PS1460 (5'-Biotin for SEPT9.2)

<400> SEQUENCE: 152
catcgatctg atgcactggc tgcaggtctg aatggc 36

<210> SEQ ID NO 153
<211> LENGTH: 41
<212> TYPE: DNA
<213> ORGANISM: Artificial
<220> FEATURE:
<223> OTHER INFORMATION: Oligonucleotide PS1711 (Loop for C9orf72)

<400> SEQUENCE: 153
ggtacggtct cacgctgtgc aggacctccc tcctgtttct g 41

<210> SEQ ID NO 154
<211> LENGTH: 41
<212> TYPE: DNA
<213> ORGANISM: Artificial
<220> FEATURE:
<223> OTHER INFORMATION: Oligonucleotide PS1712 (3'-Phosphate surface for C9orf72)

<400> SEQUENCE: 154
ggtacggtct caattctttt gaatgcactt aacagtgtct t 41

<210> SEQ ID NO 155
<211> LENGTH: 35
<212> TYPE: DNA
<213> ORGANISM: Artificial
<220> FEATURE:
<223> OTHER INFORMATION: Oligonucleotide PS1713 (5'-Biotin for C9orf72)

<400> SEQUENCE: 155
catcgatctg atgcagccca ctgcctacca agcac 35

<210> SEQ ID NO 156
<211> LENGTH: 35
<212> TYPE: DNA
<213> ORGANISM: Artificial
<220> FEATURE:
<223> OTHER INFORMATION: Oligonucleotide PS1430 (5'-Biotin for FMR1)

<400> SEQUENCE: 156
catcgatctg atgcagcaag gaggtgcatc ggccc 35

<210> SEQ ID NO 157
<211> LENGTH: 45
<212> TYPE: DNA

-continued

```
<213> ORGANISM: Artificial
<220> FEATURE:
<223> OTHER INFORMATION: Oligonucleotide PS145' (3'Phosphate surface for
      FMR1)

<400> SEQUENCE: 157

ggtacggtct caattcaaag ttgaggtttg tttcacagtg gaatg                45


<210> SEQ ID NO 158
<211> LENGTH: 41
<212> TYPE: DNA
<213> ORGANISM: Artificial
<220> FEATURE:
<223> OTHER INFORMATION: Oligonucleotide PS1393 (Loop for FMR1)

<400> SEQUENCE: 158

ggtaccgtct caaagcgagc tctccgaagt cccaatgcta g                    41


<210> SEQ ID NO 159
<211> LENGTH: 26
<212> TYPE: DNA
<213> ORGANISM: Artificial
<220> FEATURE:
<223> OTHER INFORMATION: Oligonucleotide PS1472 (Loop 5'Phosphate for
      SEPT9.1 and C9orf72)

<400> SEQUENCE: 159

agcggcactg agatttttct cagtgc                                     26


<210> SEQ ID NO 160
<211> LENGTH: 26
<212> TYPE: DNA
<213> ORGANISM: Artificial
<220> FEATURE:
<223> OTHER INFORMATION: Oligonucleotide PS189 with 5' phosphate group

<400> SEQUENCE: 160

aatggcactg agcttttgct cagtgc                                     26
```

OPTIMIZATION OF IN VITRO ISOLATION OF NUCLEIC ACIDS USING SITE-SPECIFIC NUCLEASES

INTRODUCTION

The present invention relates to methods for the preparation of nucleic acid target regions for isolation as well as optimized methods of nucleic acid isolation and enrichment. Indeed, sample isolation and enrichment are critical first steps in the study of nucleic acids, influencing both nucleic acid quantity and quality, which in turn directly impacts the quality of data obtained in downstream applications (e.g. sensitivity, coverage, robustness, and reproducibility). This is particularly important in applications in which only certain target nucleic acid regions are analysed from a more complex mixture, or in cases where a low amount of target nucleic acid is present. As an example, the human "exome" (regions coding for proteins) represents only about 1% of the total genome, yet harbours 85% of DNA variations known to be associated with genetic disease. Thus, isolation and enrichment are of particular interest in clinical applications associated with the exome, such as diagnostics and genetic risk assessment.

While whole-genome analyses may be used even when few target regions are of interest, it is often not feasible to sequence an entire genome, due to technical, economical, and/or time constraints. Furthermore, whole-genome sequencing requires vastly increased computing power and storage to analyse the large amount of data generated. Nucleic acid isolation is therefore desirable in order to limit analyses to a specific subset of nucleic acid molecules.

Recently, methods of nucleic acid isolation and enrichment have been described, wherein a target region of a nucleic acid molecule is isolated from a sample via the use of one or more site-specific nucleases, in particular CRISPR/Cas nucleases (see, in particular, PCT application no. EP2018/071557, incorporated herein by reference in its entirety). These nucleases enable highly specific isolation of target regions within a nucleic acid molecule as they remain bound to target sites, thereby shielding them from external treatments such as exonuclease digestion. These methods are particularly advantageous for isolating nucleic acid target regions as the characteristics of the original nucleic acid molecule (e.g. chemical modifications, such as base modifications, and nucleic acid sequence information, such as mismatches or SNPs) may be conserved. In particular, these methods avoid the need for amplification of a target. Furthermore, these methods are compatible with a wide variety of downstream technologies, such as methods of nucleic acid sequencing. These methods show greatly increased specificity in isolating nucleic acid target regions.

The inventors have surprisingly further identified a method of preparing nucleic acid molecules for downstream isolation of a target region and have shown that when coupled with downstream isolation, efficacy is improved. Indeed, the inventors have surprisingly shown that efficacy may be improved by at least 10,000-fold.

DETAILED DESCRIPTION OF THE INVENTION

Before describing the present invention in detail, it is to be understood that the invention is not limited to particularly exemplified aspects and may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety. However, publications mentioned herein are cited for the purpose of describing and disclosing the protocols, reagents and proteins that are reported in the publications and that might be used in connection with the invention. Nothing herein is to be construed as an admission that the invention is not entitled to antedate such disclosure by virtue of prior invention.

Furthermore, the practice of the invention employs, unless other otherwise indicated, conventional techniques of protein chemistry, molecular biology, microbiology, recombinant DNA technology, and pharmacology, which are within the skill of the art. Such techniques are explained fully in the literature. See, for example, Ausubel et al., Current Protocols in Molecular Biology, Eds., John Wiley & Sons, Inc. New York, 1995, Remington's Pharmaceutical Sciences, 17th ed., Mack Publishing Co., Easton, Pa., 1985, and Sambrook et al., Molecular cloning: A laboratory manual 2nd edition, Cold Spring Harbor Laboratory Press—Cold Spring Harbor, NY, USA, 1989.

In the claims which follow and in the preceding description, the words "comprise," "comprises," "comprising," and other variations are used in an inclusive sense, i.e. to specify the presence of the stated features but not to preclude the presence or addition of further features in various embodiments of the invention, except where the context requires otherwise due to express language or necessary implication. Furthermore, the terms "a," "an," and "the," as used herein include plural forms unless the content of the present application clearly dictates otherwise. As an example, "a target region" therefore also includes two or more target regions.

A first aspect of the present invention is a method of preparing a nucleic acid molecule comprising a target region for isolation from a sample. This method is advantageous as the nucleic acid molecules comprising a target region prepared with this method may then be used in a variety of downstream isolation methods. The inventors have surprisingly furthermore shown that when said method is coupled with a downstream isolation method, the efficacy of isolation of a nucleic acid target region is improved. Indeed, as mentioned above, the efficacy may be improved by at least 10,000-fold. In cases where a target region need not be highly enriched, the nucleic acid molecule comprising a target region obtained with this preparatory method may in and of itself be sufficiently isolated or enriched for downstream uses. The method described herein furthermore retains many additional advantages. Advantageously, all characteristics of the nucleic acid target region (e.g. chemical modifications, mismatches) are conserved, as the original nucleic acid molecule remains intact when using this method. In addition, multiplex assays using multiple Cas proteins for the preparation of multiple nucleic acid molecules comprising target regions can be easily designed with no risk of primer interactions or cross-recognition. The method may furthermore be advantageously used to prepare nucleic acids comprising target regions from small sample sizes or samples with low levels of target nucleic acid. The present invention furthermore remains quick and inexpensive, may be performed directly on samples, and has few processing steps.

Advantageously, all steps may be performed in the same container. Thus, the method is also simple and minimizes sample loss in the absence of material transfer between containers. Finally, in the absence of any amplification steps in this method, bias in downstream methods may also be reduced.

Said method of preparing a nucleic acid molecule comprising a target region for isolation from a sample comprises the steps of:

a) contacting a population of nucleic acid molecules with:
   - a first Class 2 Type V Cas protein-gRNA complex, wherein the gRNA comprises a guide segment that is complementary to a first sequence within a nucleic acid molecule, said first sequence being located adjacent to said target region, thereby forming a Class 2 Type V Cas protein-gRNA-nucleic acid complex, and
   - a protector molecule, b) contacting the population of nucleic acid molecules with at least one enzyme having exonuclease activity, c) recovering said nucleic acid molecule comprising the target region from the Class 2 Type V Cas protein-gRNA-nucleic acid complex formed in step a), and d) contacting the nucleic acid molecule of step c) with a processive polymerase.

In the method described above, the steps are performed sequentially in the order provided, with step a) performed first followed by step b) then step c) then step d). The nucleic acid molecule comprising the target region may be contacted simultaneously or sequentially with the Class 2 Type V Cas protein-gRNA complex and the protector molecule in any order (i.e. the nucleic acid molecule may be first contacted with the Class 2 Type V Cas protein-gRNA complex followed by the protector molecule or vice versa) in step a)). Step b) necessarily follows step a) as the Class 2 Cas Type V protein-gRNA complex and protector molecule of step a) protect the target region from downstream degradation by one or more enzymes having exonuclease activity according to step b).

Preferably, the method of preparing a nucleic acid molecule comprising a target region for isolation from a sample comprises the steps of:

a) contacting a population of nucleic acid molecules with:
   - a Class 2 Type V Cas protein-gRNA complex, wherein the gRNA comprises a guide segment that is complementary to a first sequence within a nucleic acid molecule, said first sequence being located adjacent to said target region, thereby forming a Class 2 Type V Cas protein-gRNA-nucleic acid complex, and
   - a first protector molecule, b) contacting the population of nucleic acid molecules with at least one enzyme having exonuclease activity, thus degrading unprotected nucleic acid molecules, c) recovering said nucleic acid molecule comprising the target region from the Class 2 Type V Cas protein-gRNA-nucleic acid complex formed in step a), and d) contacting the nucleic acid molecule of step c) with a processive polymerase, preferably a mesophilic or thermophilic polymerase, even more preferably a T4 DNA polymerase, thus performing end repair on said nucleic acid molecule.

In some cases, additional steps may be included in the method.

As a non-limiting example, an additional step of fragmenting one or more nucleic acid molecules to obtain a population of nucleic acid molecules may be included in the above method prior to step a), simultaneously to step a), or between steps a) and b). As a non-limiting example, an additional step of linearizing one or more nucleic acid molecules may be included in the above method prior to step a) or between steps a) and b). This step may notably be included when the sample or population of nucleic acid molecules comprises non-linear molecules. As a non-limiting example, an additional step of incubation may be further comprised before, during, or after any steps of the above method. As a non-limiting example, a step of storage may be further comprised after step c). These optional additional steps are further detailed below.

Preparation of a Nucleic Acid Molecule Comprising a Target Region for Isolation

The expression "preparing a nucleic acid molecule comprising a target region for isolation" "preparing a nucleic acid molecule comprising a target region" or "preparation of a nucleic acid molecule comprising a target region for isolation" as used herein refer to the obtention of a nucleic acid comprising both a target region and additional non-target regions flanking one or both sides of said target region. The nucleic acid molecule comprising a target region for isolation is advantageously suitable to a variety of downstream methods. Advantageously, the nucleic acid molecule obtained with this method of preparation may comprise blunt ends or a 3' single adenine base overhang in view of step d). The nucleic acid molecule obtained with this method may advantageously be further subject to modification of the ends of the nucleic acid (e.g. ligation of blunt ended adaptors or linkers) for use in downstream methods.

The term "sample" as used herein refers to any material or substance comprising a population of nucleic acid molecules, including, for example, biological, environmental, or synthetic samples. A "biological sample" may be any sample which may contain a biological organism, such as, for example, bacteria, viruses, archaea, animals, plants, and/or fungi. A "biological sample" according to the invention also refers to a sample which may be obtained from a biological organism, such as a cellular extract obtained, for example, from bacteria, viruses, archaea, plants, fungi, animals, and/or other eukaryotes. Molecules of the nucleic acid of interest can be obtained directly from an organism or from a biological sample obtained from an organism, e.g., from blood, urine, cerebrospinal fluid, seminal fluid, saliva, sputum, stool and tissue (such as cell tissue or plant tissue). Any cell, tissue or body fluid may be used as a source of nucleic acid in the context of the invention. Nucleic acid molecules may also be recovered or purified from cultured cells, such as a primary cell culture or a cell line. The cells or tissues from which nucleic acids of interest are obtained can be infected with a virus or other intracellular pathogen. A sample can also be total nucleic acids extracted from a biological specimen. An "environmental sample" may be any sample comprising nucleic acid that is not taken directly from a biological organism (e.g. soil, seawater, air, etc.), and may comprise nucleic acids that are no longer present within a biological organism. A "synthetic sample" comprises artificial or engineered nucleic acids. Alternatively, the sample may be from any source suspected of comprising a target nucleic acid region.

In certain embodiments, the method of the invention may comprise one or more steps of treating the sample to facilitate the preparation of the nucleic acid comprising the target region according to the method of the present invention. As a non-limiting example, the sample may be concentrated, diluted, or disrupted (e.g. by mechanical or enzymatic lysis). Nucleic acids may be completely or partially purified prior to step a) of the present method, or may be in non-purified form.

The term "nucleic acid molecule" as defined herein refers to a polymer of nucleotide monomers including deoxyribonucleotides (DNA), ribonucleotides (RNA), or analogs thereof, as well as combinations thereof (e.g. DNA/RNA chimeras). The deoxyribonucleotide and ribonucleotide monomers described herein refer to monomeric units which comprise a triphosphate group, the adenine ("A"), cytosine ("C"), guanine ("G"), thymine ("T"), or uracil (U) nitrogenous base, and a deoxyribose or ribose sugar, respectively. Modified nucleotide bases are also encompassed herein, wherein the nucleotide bases are, for example, hypoxanthine, xanthine, 7-methylguanine, inosine, xanthinosine, 7-methylguanosine, 5,6-dihydrouracil, 5-methylcytosine, pseudouridine, dihydrouridine, or 5-methylcytidine. In the context of the present invention, when describing nucleotides, "N" represents any nucleotide, "Y" represents any pyrimidine, and "R" represents any purine. Nucleotide monomers are linked by inter-nucleotide linkages, such as phosphodiester bonds, or phosphate analogs thereof and associated counter ions (e.g., $H^+$, $NH_4^+$, $Na^+$). Nucleic acid molecules of the invention may be double-stranded or single-stranded and will most often be double-stranded DNA. However, it is understood that the invention also applies to single-stranded DNA-single-stranded DNA duplexes, perfectly paired or not perfectly paired, or alternatively to single-stranded DNA-single-stranded RNA duplexes, perfectly paired or not perfectly paired, or alternatively to single-stranded RNA-single-stranded RNA duplexes, perfectly paired or not perfectly paired, as well as single-stranded DNA and single-stranded RNA. In particular, the invention applies to the secondary structures of a sole single-stranded DNA or of a sole single-stranded RNA. When the nucleic acid molecule is single-stranded RNA (e.g. mRNA) or a single-stranded RNA-single-stranded RNA duplex (e.g. viral dsRNA), said RNA may be reverse transcribed prior to being contacted with the Class 2 Type V Cas protein-gRNA complex. Duplexes may consist of at least partial re-pairing of two single nucleic acid strands obtained from samples of different origins. Nucleic acid molecules may be naturally occurring (e.g. of eukaryotic or prokaryotic origin), or synthetic. Nucleic acid molecules may comprise circular nucleic acid molecules, such as covalently closed circular DNA and/or circular RNA, including plasmids and/or circular chromosomes, or linear nucleic acid molecules. Nucleic acid molecules may notably comprise genomic DNA (gDNA), cDNA, hnRNA, mRNA, rRNA, tRNA, microRNA, mtDNA, cpDNA, cfDNA (such as ctDNA or cffDNA), cfRNA and the like.

Nucleic acid molecule length may range from only a few monomeric units (e.g. oligonucleotides, which may range, for example, from less than 100 to up to 200 monomers in length) to several thousand, tens of thousands, hundreds of thousands, or millions of monomeric units. Preferably, the nucleic acid molecules comprise one or more cfDNA molecules, such as those described above. In a first aspect, the length of the nucleic acid molecule is less than 300 bp, for example comprised between about 125 and 225 bp, preferably between 130 and 200 bp. In a second aspect, the length of the nucleic acid molecule is equal or superior to 300 bp. In the present application, it should be understood that nucleic acid molecules are expressed in the 5' to 3' direction from left to right, unless specified otherwise.

The term "population of nucleic acid molecules" as used herein refers to more than one nucleic acid molecule. Said population may comprise one or more different nucleic acid molecules, of any length, of any sequence, as defined above. A population of nucleic acid molecules may notably comprise more than $10^3$, $10^4$, $10^5$, $10^6$, $10^7$, $10^8$, $10^9$, or $10^{10}$ different nucleic acid molecules.

The "nucleic acid target region" or "target region" as defined herein refers to a specific nucleic acid molecule that is present within a more complex sample or population of nucleic acid molecules or a specific nucleic acid region that is present within a larger nucleic acid molecule, and that is to be specifically targeted for isolation or enrichment. When the target region is present within a larger nucleic acid molecule, it is preferably flanked on one side or on both sides by non-target region(s). The target region is preferably flanked on its first side by a first sequence that is at least partially complementary to the guide segment of the crRNA molecule or gRNA comprised in the Class 2 Type V Cas protein-gRNA complex. The nucleic acid target region is furthermore preferably flanked on its second side by a protector molecule. When said protector molecule is a Class 2 Cas protein-gRNA complex, the nucleic acid target region is flanked on its second side by a second sequence that is at least partially complementary to the guide segment of the crRNA molecule or gRNA comprised in the Class 2 Cas protein-gRNA complex. Thus, said first and second sequences flank the target region.

In some embodiments, two or more different nucleic acid molecules comprising target regions may be prepared. The "nucleic acid molecule comprising a target region" of the invention may therefore comprise two or more different nucleic acid molecules comprising target regions, preferably at least 2, 5, 10, 25, 50, 100, or more regions. The nucleic acid target region may be coding or non-coding, or a combination of the two. The target region may be genomic or episomic. The target region may comprise one or more repeat regions, rearrangements, duplications, translocations, deletions, mismatches, SNPs, and/or modified bases, such as epigenetic modifications. In some cases, the nucleic acid target regions may be identical (e.g. corresponding to repeat sequences). In other cases, the nucleic acid target regions may be different. Preferably, the target nucleic acid region will have a length of at least about 44, 50, 100, 250, 500, 1,000, 5,000, 10,000, 20,000, 30,000, 40,000, 50,000, 60,000, 70,000, 80,000, 90,000, or 100,000 nucleotides.

The term "region" as used herein refers to an uninterrupted nucleotide polymer. Although a given gRNA may permit the preparation of multiple nucleic acids comprising target regions (for example, due to non-specific binding, or recognition of a sequence that is present more than once in a nucleic acid molecule), in the context of the present invention, each gRNA preferably recognizes a single sequence within a population of nucleic acid molecules. A nucleic acid molecule comprising a target region is preferably prepared via the use of at least two different gRNAs targeting a first sequence and a second sequence flanking said target region. Additional embodiments are described below.

Cas Protein

The term "Cas protein" as used herein refers to RNA-guided endonucleases which specifically recognize and bind to a nucleic acid target region. In order to specifically recognize and bind to a specific target region, a Cas protein complexes with a "guide RNA," or "gRNA," to form a "Cas protein-gRNA complex." Binding specificity of the Cas protein is determined by the gRNA, which comprises a "guide segment," whose sequence must be at least partially complementary to that of a given nucleic acid sequence. The guide segment within the Cas protein-gRNA complex hybridizes with said nucleic acid sequence, thereby forming a Cas protein-gRNA-nucleic acid complex. Successful binding of the Cas protein-gRNA complex to the nucleic acid sequence further requires the presence of a short, conserved sequence in the nucleic acid molecule that is located immediately adjacent to the hybridized region. This sequence is known as the protospacer-associated motif or "PAM." Thus, Cas protein-gRNA complex binding to a nucleic acid sequence comprises both nucleic acid hybridization via the guide segment and interaction of the Cas protein itself with the PAM. Following binding of the Cas protein-gRNA complex to a nucleic acid sequence, the Cas protein typically cleaves the nucleic acid by breaking the phosphodiester bonds between two adjacent nucleotides in each of the strands of a double-stranded nucleic acid molecule. Specifically, one domain of the Cas protein cleaves the nucleic acid strand that is hybridized with the gRNA, while a second domain of the Cas protein cleaves the non-hybridized nucleic acid strand. Cleavage of the two strands of a double-stranded molecule may be staggered, generating a single-stranded overhang, or blunt. As can be easily understood by the skilled person, when the nucleic acid population is contacted with more than one Cas protein-gRNA complex in step a), more than one Cas protein-gRNA-nucleic acid complex may be formed. These aspects are further detailed below.

Three main classes of Cas protein have been described to date (Class 1, Class 2, and Class 3). It should further be noted that among the Class 2 Cas proteins, at least five difference types have been identified to date (i.e. Type I, II, III, IV, V). As a non-limiting example, a Cas protein may be selected from the Class 2 Cas proteins, specifically the Class 2 Type V and Class 2 Type II Cas proteins, more specifically from among the Cas9, Cpf1, C2c1, C2c3, and C2c2 (Cas13a) proteins.

As a non-limiting example, a Class 2 Cas protein may be from one of the following species: *Streptococcus pneumoniae, Streptococcus pyogenes, Streptococcus thermophilus, Streptococcus canis, Staphylococcus aureus, Neisseria meningitidis, Treponema denticola, Francisella tularensis, Francisella novicida, Pasteurella multocida, Streptococcus mutans, Campylobacter jejuni, Campylobacter lad, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globosa, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pasteuri, Filifactor alocis, Veillonella* sp. *Suterella wadsworthensis, Leptotrichia* sp., *Corynebacterium diphtheriae, Acidaminococcus* sp., or Lachnospiraceae sp., *Prevotella albensis, Eubacterium eligens, Butyrivibrio fibrisolvens, Smithella* sp., *Flavobacterium* sp., *Porphyromonas crevioricanis*, or Lachnospiraceae *bacterium* ND2006.

As a non-limiting example, the Class 2 Cas protein may be J3F2B0, Q0P897, Q6NK13, A0Q5Y3, Q927P4, A1IQ68, C9X1G5, Q9CLT2, J7RUA5, Q8DTE3, Q99ZW2, G3ECR1, Q73QW6, G1UFN3, Q7NA12, E6WZS9, A7HP89, D4KTZ0, DOW2Z9, B5ZLK9, F0RSV0, A0A1L6XN42, F2IKJ5, S0FEG1, Q6KIQ7, A0A0H4LAU6, F5X275, F4AF10, U5ULJ7, D6GRK4, D6KPM9, U2SSY7, G4Q6A5, R9MHT9, A0A111NJ61, D3NT09, G4Q6A5, A0Q7Q2, or U2UMQ6. Accession numbers are from UniProt (www.uniprot.org), version last modified on Jan. 10, 2017. As a non-limiting example, the gene encoding the Class 2 Cas protein may be any gene comprising a nucleotide sequence wherein said sequence generates the amino acid sequence of the corresponding Cas protein, such as one of those listed above. The skilled person will easily understand that the nucleotide sequence of the gene may vary due to degeneracy of the genetic code, without altering the amino acid sequence. The Class 2 Cas protein may furthermore be codon-optimized for expression in a bacterial (e.g. *E. coli*), insect, fungal, or mammalian cell.

Class 2 Cas proteins and protein orthologs have also been identified in other bacterial species and are notably described in Example 1 of PCT application no. WO 2015/071474, incorporated herein by reference. In some cases, the Cas protein may be a homolog or an ortholog, for example, to a Class 2 Cas protein of one of the species listed above.

While a wild-type Cas protein has endonuclease activity, Cas protein-gRNA complex binding to a nucleic acid sequence is independent of its catalytic activity. Variants and mutants of the wild-type Cas protein have been described. As a non-limiting example, mutated Cas proteins lacking the ability to cleave one or both strands of the target nucleic acid molecule containing a target region have been described, as have Cas variants that retain endonuclease activity but have improved binding specificity (e.g. the Class 2 Cas protein eSpCas9, as described in Slaymaker et al., *Science,* 2015, 351(6268): 84-86).

The term "Cas nickase" as used herein, refers to a modified Cas protein comprising one inactive catalytic nuclease domain and one active catalytic nuclease domain. A Cas nickase complexed with a gRNA will bind to a specific nucleic acid sequence as described above, but will only break the phosphodiester bond between two nucleotides in one strand of a double stranded nucleic acid. A Cas nickase may cleave either the nucleic acid strand that is hybridized with the gRNA, or the non-hybridized nucleic acid strand which is at least partially identical to the gRNA. The "nick site" refers to the site at which the double-stranded nucleic acid molecule has undergone a break on one strand. A 3' hydroxyl group and a 5' phosphate group are produced at the nick site.

The terms "catalytically dead," "catalytically inactive," or "dead," as used herein, refer to a modified Cas protein comprising two catalytically inactive nuclease domains. A catalytically inactive Cas protein complexed with a gRNA will bind a specific sequence as described above, but will not cleave or nick either strand of the double stranded nucleic acid.

A modified Class 2 Cas protein may comprise one or more modifications causing specific inactivation of one or both of its nuclease domains as described above. Preferably, such modifications do not affect Class 2 Cas protein-gRNA complex formation, Class 2 Cas protein recognition of the PAM motif, and/or the strength and/or stability of binding to a nucleic acid sequence and/or binding of the Class 2 Cas protein-gRNA complex to a nucleic acid sequence target region. As a non-limiting example, possible modifications to a Class 2 Cas protein include substitutions at one or more of the following amino acids: E762, HH983 or D986, D10, H840, G12, G17, N854, N863, N982, or A984, wherein amino acids are numbered according to the amino acid sequence of the Cas9 protein of *S. pyogenes* (having, for example, accession number Q99ZW2 in the Uniprot database), or at the equivalent amino acid position(s) in another Class 2 Cas protein. As an example, the one or more amino acids may be substituted by an alanine (e.g. E762A, HH983AA or D986A, D10A, H840A, G12A, G17A, N854A, N863A, N982A or A984A), or by another amino acid which causes inactivation of the corresponding catalytic domain.

As a non-limiting example, a Class 2 Cas nickase may comprise a substitution at the amino acid position equivalent to the H840 (e.g. H840A) or D10 (e.g. D10A) position of the Cas9 protein of *S. pyogenes* as described above. Preferably, the "Cas9n" protein comprises a substitution at the amino acid position equivalent to H840 (e.g. H840A) or at position D10 (e.g. D10A). Depending on the nickase variant (e.g. comprising a substitution at D10 or H840), the nickase will nick either the gRNA-hybridized strand or the non-hybridized strand. In particular, a nickase comprising a substitution at D10 will nick the gRNA-hybridized strand, while a nickase comprising a substitution at H840 will nick the strand that is not hybridized to the gRNA. Alternatively, the Class 2 Cas nickase may comprise a substitution at the amino acid position equivalent to the R1226 (e.g. R1226A) of the Cpf1 protein. A Class 2 Cas nickase comprising a substitution at R1226 will nick the strand that is not hybridized to the gRNA.

As a non-limiting example, a catalytically inactive Class 2 Cas protein, such as the catalytically inactive Cas9 protein (also referred to herein as "Cas9d" or "dCas9") will comprise substitutions at least at both of the amino acid positions equivalent the D10 and H840 in the Cas9 protein. Preferably, Cas9d comprises substitutions at least at both amino acid positions D10 and H840.

Class 2 Type V Cas Proteins

The Cas proteins used in the context of the method of preparing a nucleic acid target region for isolation are Class 2 Cas proteins, specifically Class 2 Type V Cas proteins. Indeed, as indicated above, the first step (step a)) of the method of preparing a nucleic acid molecule comprising a target region for isolation comprises contacting a population of nucleic acid molecules with a Class 2 Type V Cas protein. When catalytically active, a Class 2 Type V protein complexed with an appropriate gRNA generates a staggered cut (e.g. a short 5' overhang of 3 to 5 bases) that is distal to the PAM sequence (e.g. that is located at least 10 nucleotides distant to the PAM) of a double-stranded nucleic acid molecule (see for example Zetsche et al., Cell, 2015, 163(3): 759-771). It has been further observed that a Class 2 Type V protein-gRNA complex may remain bound to a nucleic acid molecule, and may therefore advantageously protect said nucleic acid from degradation, for example when said nucleic acid molecule is exposed to an exonuclease. Without being bound by theory, after cleavage of a double-stranded nucleic acid molecule, the Class 2 Type V protein-gRNA complex may remain bound to the nucleic acid strand comprising the PAM sequence with the opposite strand (i.e. the strand that does not comprise the PAM sequence) dissociating from the molecular complex.

Preferably, the Class 2 Type V Cas protein is catalytically active (i.e. cleaves both strands of a double stranded molecule). Preferably, the Class 2 Type V Cas protein of the invention is selected from Cpf1 (also referred to as Cas12a) and C2c1, more preferably Cpf1. The Cpf1 protein is preferably the Cpf1 protein of one of appropriate species listed above, more preferably one of the following species or strains: *F. novicida* U112 (accession no: AJI61006.1), *P. albensis* (accession no: WP_024988992.1), *Acidaminococcus* sp. BV3L6 (accession no: WP_021736722.1), *E. eligens* (accession no: WP_012739647.1), *B. fibrisolvens* (accession no: WP_027216152.1), *Smithella* sp. SCADC (accession no: KFO67988), *Flavobacterium* sp. 316 (accession no: WP_045971446.1), *P. crevioricanis* (accession no: WP_036890108.1) Bacteroidetes oral taxon 274 (accession no: WP_009217842.1), or Lachnospiraceae *bacterium* ND2006 (accession no: WP_051666128.1). In a preferred embodiment, said *Acidaminococcus* sp. BV3L6 Cpf1 is a variant comprising the following amino acid substitutions: S542R/K607R or S542R/K548V/N552R (Gao et al., *Nat Biotechnol.* 2017, 35(8): 789-792).

Guide RNA

The term "guide RNA" or "gRNA" as used herein, refers to two guide RNA molecules, consisting of a crRNA molecule and a tracrRNA molecule. Alternatively, the term gRNA as used herein, refers to a single guide RNA molecule, or sgRNA, that includes both crRNA and tracrRNA sequence segments. Alternatively, the gRNA may consist of a crRNA molecule only. The gRNA molecule may be chemically modified, for example comprising base, sugar, or phosphate modifications of one or more ribonucleotides. Optionally, the 5' and/or 3' ends of the gRNA molecule may be modified, for example by covalent conjugation to another molecule or a chemical group.

The crRNA molecule or segment is preferably 20 to 75 nucleotides in length, more preferably 30 to 60 nucleotides, even more preferably 40 to 45 nucleotides in length. The crRNA molecule or segment preferably comprises a first region, referred to herein as the "guide segment," whose sequence is at least partially complementary to a sequence present in a nucleic acid molecule. An exemplary generic crRNA nucleotide sequence is shown in SEQ ID NO: 2 with the guide segment represented by the stretch of 'N' nucleotides. Preferably, the guide segment of the gRNA of the present invention comprises at least 70%, at least 80%, at least 85%, at least 90%, at least 95%, at least 96%, at least 97%, at least 98%, at least 99%, or more preferably 100% sequence complementarity with a sequence present in a nucleic acid molecule. Preferably, when complementarity is less than 100%, mismatches are located near the crRNA end that hybridizes farthest from the PAM. As an example, when the Class 2 Type II Cas protein is Cas9, mismatches are preferably comprised at the 5' end of the crRNA molecule or segment (e.g. within the first 7 nucleotides), as Cas9 recognizes a PAM at the 3' end of the crRNA. Alternatively, when the Class 2 Type V Cas protein is Cpf1, mismatches are preferably comprised at the 3' end of the crRNA molecule or segment (e.g. within the last 7 nucleotides), as Cpf1 recognizes a PAM at the 5' end of the crRNA. The guide segment is preferably at least 10, 11, 12, 13, 14, 15, 16, 17, 18, 19, 20, 21, 22, 23, 24, or 25 nucleotides in length, more preferably 15, 16, 17, 18, 19, 20, 21, 22, 23, 24, or 25, even more preferably 17, 18, 19, 20, 21, 22, 23, or 24 nucleotides in length. Alternatively, the guide segment is preferably from 10 to 30, more preferably 15 to 25, even more preferably from 17 to 24, nucleotides in length. The crRNA molecule or segment preferably comprises a second region, referred to herein as the "tracr-mate segment." The tracr-mate segment comprises a sequence that is preferably at least partially complementary to the tracrRNA molecule or segment, more preferably at least partially complementary to the 5' end of the tracrRNA. The tracr-mate segment is preferably at least 10, 11, 12, 13, 14, 15, 16, 17, 18, 19, 20, 25, 30, 40, 50 nucleotides in length, more preferably at least 15 nucleotides in length, even more preferably at least 20 nucleotides in length. Preferably, the guide segment is located at the 5' end of the crRNA molecule or segment. Preferably, the tracr-mate segment is located at or near the 3' end of the crRNA molecule or segment.

The tracrRNA molecule or segment is preferably 10 to 175 nucleotides in length, more preferably 40 to 110, more preferably 60 to 90, even more preferably 65 to 80 nucleotides in length. The tracrRNA molecule or segment preferably comprises at least one secondary structure, preferably at least two secondary structures, more preferably at least three secondary structures, even more preferably three or four secondary structures. Preferably, the at least one secondary structure is located at or near the 3'-end of the tracrRNA molecule or segment. An exemplary generic tracrRNA nucleotide sequence is shown in SEQ ID NO: 3. The tracrRNA molecule preferably comprises a tracrRNA binding segment that is complementary to the tracr-mate segment of the crRNA. Preferably, the tracrRNA binding segment comprises a sequence that is at least 50%, 60%, 70%, 80%, 85%, 90%, 95%, 99%, or 100% complementary to the tracr-mate segment of the crRNA. Preferably, the tracrRNA binding segment is at least 10 nucleotides in length. The term "at or near the 5'-end" of a nucleic acid molecule as used herein refers to placement of a segment or structure within the first half of the molecule, from 5' to 3'. Similarly, the term "at or near the 3'-end" of a nucleic acid molecule as used herein refers to placement of a segment or structure within the last half of the molecule.

As a non-limiting example, a "secondary structure" present in the gRNA may be a stem-loop or hairpin, bulge, tetraloop, and/or pseudoknot. The terms "hairpin" and "stem-loop" are used interchangeably herein in the context of the gRNA and are defined below (see "protector molecule" section). According to a preferred embodiment, said gRNA comprises at least one hairpin secondary structure.

According to a first preferred embodiment, the gRNA is a sgRNA molecule comprising both crRNA and tracrRNA segments. An exemplary generic sgRNA nucleotide sequence is shown in SEQ ID NO: 4 with the guide segment represented by the stretch of 'N' nucleotides. Even more preferably, the sgRNA consists of crRNA and tracrRNA segments. Preferably, the crRNA and tracrRNA segments are fused together. Said segments are preferably fused together by a phosphodiester bond or a nucleic acid linker comprising one or more nucleotides. Said sgRNA is preferably from 30 to 180 nucleotides in length, more preferably from 40 to 90 nucleotides in length. Preferably, the 3'-end of the crRNA is fused to the 5'-end of the tracrRNA. Preferably, the crRNA and tracrRNA are fused by the addition of a linker. Alternatively, the crRNA and tracrRNA molecules may be fused by chemical linkage, such as a covalent bond (e.g. a triazole linkage).

According to a second preferred embodiment, the gRNA is composed of two separate RNA molecules consisting of a crRNA molecule and a tracrRNA molecule.

According to a third preferred embodiment, when the Class 2 Type V Cas protein is Cpf1, the gRNA consists only of a crRNA molecule. A "Cpf1-gRNA complex" may thus also be referred to interchangeably herein as a "Cpf1-crRNA complex." When the gRNA is only a crRNA molecule, at least the guide segment must be present. An exemplary generic crRNA nucleotide sequence is shown in SEQ ID NO: 1 with the guide segment represented by the stretch of 'N' nucleotides. Preferably, the crRNA molecule further comprises a secondary structure, such as a hairpin. Preferably, the crRNA molecule does not comprise a tracr-mate segment. Preferably, the guide segment is located at the 3'-end of the crRNA molecule. Preferably the secondary structure is located at or near the 5'-end of the crRNA molecule. Preferably, said crRNA is 40 to 50 nucleotides in length.

The term "complementary" as used herein refers to ability of one nucleic acid sequence or molecule (e.g. the gRNA) to undergo sequence-specific antiparallel nucleotide base pairing interactions with another nucleic acid sequence or molecule (e.g. the sequence in a nucleic acid molecule), resulting in the formation of a duplex or other higher-ordered structure. The main type of interaction is nucleotide base specific, e.g., A:T, A:U, and G:C, by Watson-Crick and Hoogsteen-type hydrogen bonding. This is also known as "nucleic acid binding," "hybridization," or "annealing." Conditions under which a nucleic acid hybridizes to a complementary region of a target nucleic acid are well-known in the art (see, for example, Nucleic Acid Hybridization, A Practical Approach, Hames and Higgins, eds., IRL Press, Washington, D.C. (1985)). Hybridization conditions depend upon the particular application, and can be routinely determined by a person skilled in the art.

In the context of the present invention, complementary binding does not mean that the two nucleic acid sequences or molecules (e.g. the gRNA and the target region, or the tracr-mate segment and the tracrRNA) must be entirely complementary to each other. Furthermore, it is not necessary for the crRNA sequence segment or molecule to be entirely complementary to the sequence in the nucleic acid molecule. Indeed, it is known that a Class 2 Cas protein-gRNA complex can specifically bind to a nucleic acid sequence having as few as 8 or 9 bases of complementarity with the gRNA. Preferably, no mismatches are present between the 10 bases of the gRNA that are closest to the PAM and the corresponding 10 bases of the complementary nucleic acid sequence which are located closest to the PAM, more preferably between the 6 bases of the gRNA that are closest to the PAM and the corresponding 6 bases of the complementary nucleic acid sequence which are located closest to the PAM, even more preferably between the base(s) of the gRNA which are located 4, 5, and/or 6 bases from the PAM and the corresponding base(s) of the complementary nucleic acid sequence which are located 4, 5, and/or 6 bases from the PAM. Indeed, if a mismatch is present at one or more of said base locations, binding will be unstable and protection of a target region from exonuclease digestion by the Class 2 Cas protein-gRNA complex will be reduced or even abolished. Off-target hybridization can be reduced by increasing the length of the crRNA segment, or by placing mismatches at or near the end of the crRNA segment that is furthest from the PAM, as indicated previously herein. Alternatively, the gRNA may be modified to have increased binding specificity via the presence of one or more modified bases or chemical modifications, such as those described in Cromwell et al., *Nat Commun.* 2018, 9(1):1448 or Orden Rueda et al., *Nat Commun.* 2017, 8:1610, incorporated herein by reference. Moreover, a nucleic acid may hybridize over one or more regions such that intervening or adjacent regions are not involved in the hybridization event (e.g., a loop or hairpin structure). The person skilled in the art can easily design one or more gRNA molecules based on their general knowledge and in view of the parameters detailed above, according to the nucleic acid sequence(s) that are to be hybridized.

The ratio of the number of molecules of nucleic acid to Cas protein to gRNA (nucleic acid:Cas protein:gRNA) has previously been shown to influence the efficacy of isolation of a target region. The ratio the number of molecules of nucleic acid comprising a target region:Cas protein:gRNA may notably be optimized here according to the nucleic acid comprising a target region that is to be prepared and/or the origin and/or the complexity of the population of nucleic acid molecules. Without being limited by theory, optimization may particularly depend on DNA complexity, with more complex nucleic acid populations requiring higher quantities of Cas protein and gRNA. As a non-limiting example, less complex nucleic acid populations may essentially comprise repeating sequences or PCR amplified fragments, whereas more complex nucleic acid populations may comprise genomic DNA. As a non-limiting example, a ratio of 1:10:20 may be used to prepare a nucleic acid comprising a target region when said nucleic acid molecule is present within a population of nucleic acid molecules generated by PCR. In contrast, a ratio of 1:1600:3200 is preferable when said population comprises or consists of *E. coli* genomic DNA, while a ratio of 1:100000:200000 is preferable when said population comprises or consists of human genomic DNA. When multiple gRNAs are used (e.g. wherein two gRNAs recognize two a first sequence and a second sequence flanking a target region, or in multiplexing to prepare multiple nucleic acid molecules comprising different target regions), a single optimized ratio of nucleic acid:Cas protein: gRNA may be selected for all gRNAs. Alternatively, an optimized ratio may be selected for each gRNA individually.

According to a preferred embodiment, the ratio is at least 1:10:10, more preferably at least 1:10:20, even more preferably at least 1:10:50. A ratio of at least 1:10:20 is particularly preferred when template DNA is generated by PCR. Preferably, guide RNAs are selected for efficiency using a PCR template, followed by optimization of the ratio of nucleic acid comprising a target region:Cas protein:gRNA on an appropriate template, if necessary (e.g. if said template differs). Preferably, cleavage efficiency of a wild type Cas protein-gRNA complex is at least 70%, more preferably at least 80%, even more preferably at least 90%. Preferably, the efficiency of protection of a target region by a Cas protein-gRNA complex is at least 70%, more preferably at least 80%, even more preferably at least 90%. Preferably, the ratio of the number of molecules of nucleic acid comprising target region:Cas protein:gRNA is at least 1:200:400, more preferably at least 1:400:800, even more preferably at least 1:800:1600, at least 1:1600:3200, or at least 1:3200:6400 when the nucleic acid is prepared from nucleic acids of bacterial origin, such as gram-negative bacteria, such as *E. coli*. According to an alternative preferred embodiment, the ratio of the nucleic acid comprising target region:Cas protein:gRNA is at least 1:10,000:20,000, more preferably at least 1:100,000:200,000. The skilled person can easily adapt the ratio of the nucleic acid comprising the target region:Cas protein:gRNA according to the nucleic acid comprising the target region to be prepared and/or the origin and/or complexity of nucleic acid molecules in view of the ratios provided above. While the proportion of Cas protein to gRNA may vary, the gRNA is advantageously provided in at least two-fold excess to the Cas protein to ensure that the Cas protein is successfully loaded with gRNA. Higher ratios of Cas protein (e.g. 1:20:40, 1:50:100, etc. for a PCR target) and, optionally, of gRNA (e.g. 1:10:30, 1:10:40, etc. for a PCR target) may of course be used. The above ratios are preferably used in step a) of the method of the invention, in particular with regard to the ratio of nucleic acid comprising a target region: Class 2 Type V Cas protein:gRNA. In cases where the protector molecule is a Class 2 Cas protein, the above ratios may also be used.

Protospacer Adjacent Motif (PAM)

The term “protospacer adjacent motif” or “PAM” as used herein, refers to a short nucleotide sequence (e.g. 2 to 6 nucleotides) which is recognized directly by the Cas protein itself, more particularly by the Class 2 Cas protein. The PAM sequence and its placement will vary according to the Cas protein used, and can easily be determined by the person skilled in the art according to his general knowledge, or using techniques such as that described in Karvelis et al., *Genome Biology,* 2015, 16:253. As an example, the Cpf1 protein of *F. novicida* recognizes the PAM 5'-TTTN-3' or 5'-YTN-3', the Cpf1 protein of *Acidaminococcus* sp. recognizes the PAM 5'-TTTN-3. As a further example, the Cas9 protein of *S. pyogenes* recognizes the PAM 5'-NGG-3'. In contrast, the Cas9 protein of *S. aureus* recognizes the PAM 5'-NNGRRT-3', the Cas9 of *N. meningitidis* recognizes the PAM 5'-NNNNGATT-3', the Cas9 of *S. thermophilus* recognizes the PAM 5'-NNAGAA-3', the Cas9 of *T. denticola* recognizes the PAM 5'-NAAAAC-3', the Cas9 of *S. canis* recognizes the PAM 5'-NNG-3', an engineered Cas9 protein derived from *F. novicida* recognizes the PAM 5'-YG-3'. The PAM motif is generally located on the non-hybridized strand of a double-stranded target nucleic acid molecule at a site that is immediately adjacent to the 5' or 3' end of the nucleic acid sequence that is hybridized to the gRNA. The required placement of the PAM depends on the Cas protein used (e.g. the PAM is preferably located immediately adjacent to the 3'-end of the gRNA when using the Cas9 protein, while the PAM is preferably located immediately adjacent to the 5'-end of the gRNA when using the Cpf1 protein). Alternatively, the PAM motif may be comprised in the gRNA molecule itself or in a separate DNA oligonucleotide that is added to the sample. As an example, addition of a PAM to the sample via one of these means may be necessary when using the present method to isolate single-stranded RNA molecules. Binding of the Class 2 Cas protein to the PAM is thought to slightly destabilize a double stranded nucleic acid, thereby allowing hybridization of the gRNA to the nucleic acid sequence.

When the Cas protein is of Class 2 Type V, the PAM is preferably located on the non-hybridized strand of the target region immediately adjacent to 5' end of the gRNA. When the Cas protein is of Class 2 Type II, the PAM is preferably located on the non-hybridized strand of the target region immediately adjacent to the 3' end of the gRNA. However, in some cases, the PAM is preferably comprised within the gRNA molecule itself or on a DNA oligonucleotide.

Protector Molecule

The term “protector molecule” as used herein refers to molecule that binds to a nucleic acid molecule and protects an adjacent nucleic acid region (i.e. a target region) from degradation. The protector molecule may bind to either a free end of a nucleic acid molecule or within a nucleic acid molecule. When binding within a nucleic acid molecule, said protector molecule will preferably bind to a specific sequence. Said protector molecule must bind to the same uninterrupted nucleotide polymer as the Class 2 Type V Cas protein-gRNA complex. In the context of the present invention, the protector molecule preferably binds to a second sequence that is adjacent to the target region, such that said target region is flanked on one side by the second sequence to which the Class 2 Type V Cas protein-gRNA complex binds (thereby forming a Class 2 Type V Cas protein-gRNA-nucleic acid complex) and on the other side by the protector molecule.

In the context of the present invention, the protector molecule is preferably a hairpin adaptor or a site-specific endonuclease, more preferably a Cas protein-gRNA complex, even more preferably a Class 2 Cas protein-gRNA complex. However, other site-specific nucleases that stably bind a nucleic acid at a specific sequence, such as transcription activator-like effector nucleases (TALENs) or zinc-finger proteins, are also included in the scope of the invention.

According to a preferred embodiment, the protector molecule binds to a sequence located at least 50 nucleotides, preferably at least 100, 250, 500, 1,000, 5,000, 10,000, 20,000, 30,000, 40,000, 50,000, 60,000, 70,000, 80,000, 90,000, 100,000, 200,000, 500,000, 750,000, or 1,000,000 nucleotides distant to the Class 2 Type V Cas protein-gRNA-nucleic acid complex. Thus, according to a preferred embodiment, the target region has a length of at least 50, 100, 250, 500, 1,000, 5,000, 10,000, 20,000, 30,000, 40,000, 50,000, 60,000, 70,000, 80,000, 90,000, 100,000, 200,000, 500,000, 750,000, or 1,000,000 nucleotides.

In one embodiment of the method of the invention, the protector molecule binds to a free end of the nucleic acid molecule comprising the target region. Thus, according to a preferred embodiment, the protector molecule is a hairpin adaptor.

The term "hairpin" or "hairpin adaptor" as used herein refers to a molecule that base pairs with itself to form a structure having a double-stranded stem and a loop, wherein the 5'-end of one strand is physically linked to the 3'-end of the other strand through an unpaired loop. Said physical link may be either covalent or non-covalent. Preferentially, said physical link is a covalent bond. The term "loop" as used herein refers to a succession of nucleotides of a nucleic acid strand that are not paired through hydrogen bonds with nucleotides of the same or another strand of said nucleic acid, and is therefore single-stranded. The "stem" as used herein refers to a region of intra-strand pairing. Preferably, the stem comprises at least 3, 5, 10, or 20 base pairs, more preferably at least 5, 10, or 20 base pairs, even more preferably at least 10 or 20 base pairs. When the hairpin binds to the free end of a double-stranded nucleic acid molecule, the 3' and 5' ends of the hairpin ligate to the 5' and 3' ends of the double-stranded nucleic acid molecule, respectively. Preferably, said hairpin adaptor binds to any one of the free ends, preferably only one of the free ends, of a nucleic acid molecule. Said hairpin adaptor may specifically bind to one of the free ends of a nucleic acid molecule. As a non-limiting example, specific binding may be performed by fragmenting the nucleic acid molecule(s) with a non-palindromic restriction enzyme, thereby generating different overhangs at each new free end of the nucleic acid molecule. When the protector molecule is a hairpin adaptor, said protector molecule binds to any one of the free ends, preferably binds to only one of the free ends, of the nucleic acid molecule, such that said target region is flanked on one side by the first sequence to which the Class 2 Type V Cas protein-gRNA complex binds (thereby forming a Class 2 Type V Cas protein-gRNA-nucleic acid complex) and on the other side by the hairpin adaptor.

The term "free end" as used herein refers to the end of a nucleic acid molecule, which may comprise a phosphate group on the 5' end and/or a hydroxyl group on the 3' end. The free end may be blunt or comprise a single-stranded overhang. Said single-stranded overhang may be a 3' or 5' overhang. Said single-stranded overhang preferably has a length of less than 100, 50, 25, 10, 5, 4, or less than 3 nucleotides.

Preferably, said hairpin adaptor is linked to the nucleic acid molecule, preferably ligated to the nucleic acid molecule. More preferably, step a) comprises contacting the population of nucleic acids with a hairpin adaptor and linking said hairpin adaptor to a nucleic acid molecule free end. In a preferred embodiment, the method further comprises a step of linearizing the population of nucleic acid molecules prior to contacting said population with a hairpin adaptor, as described herein, if necessary (e.g. when the sample comprises circular nucleic acid molecules). Said protector molecule is preferably a hairpin adaptor when said nucleic acid molecule comprising the target region is less than 300 bp in length.

Alternatively, when the protector molecule is a second site-specific endonuclease, such as a second Class 2 Cas protein-gRNA complex, a TALEN, or a zinc-finger protein, preferably said protector molecule binds within a nucleic acid molecule.

According to a particular embodiment, the protector molecule is a Class 2 Type V or Class 2 Type II Cas protein-gRNA complex. When the protector molecule is a Cas protein-gRNA complex, it is particularly preferred that the population of nucleic acid molecules be contacted simultaneously with the Class 2 Type V-gRNA complex and said protector molecule. This is advantageous as the duration of the method is reduced. Preferably, said protector molecule is a Cpf1-gRNA complex, wherein the PAM site is adjacent to a nucleic acid target region. Thus, according to a particular embodiment of the method of preparing a nucleic acid molecule comprising a target region for isolation, step a) comprises contacting a population of nucleic acid molecules with first and second Cpf1-gRNA complexes, said first and second complexes binding respectively to a first and second sequence flanking said target region.

According to a preferred embodiment, when the protector molecule is a Cas protein-gRNA complex, the Cas protein may be a catalytically active Cas protein, a nickase, or a dead Cas protein. Thus, according to a particular embodiment, when two Cpf1-gRNA complexes are used, said two Cpf1-gRNA complexes are catalytically active. According to an alternative embodiment, a first Cpf1-gRNA complex is catalytically active while the protector molecule, corresponding to a second Cpf1-gRNA complex, is a nickase or catalytically dead.

Multiple Cas protein-gRNA complexes and protector molecules may be used in any of the above embodiments. Indeed, according to a particularly preferred embodiment, two or more Cas protein-gRNA complexes may be used alone or in combination with two or more protector molecules to prepare two or more nucleic acid molecules comprising target regions for isolation. According to a further embodiment, when the method is used for the preparation of multiple nucleic acids each comprising a target region for isolation, step a) comprises contacting the population of nucleic acid molecules with multiple Class 2 Type V Cas protein-gRNA complexes and protector molecules such that each target region is flanked on a first side by a first sequence to which said complex will bind (thereby forming a Class 2 Type V Cas protein-gRNA-nucleic acid complex) and on a second side by said protector molecule. Preferably, when said target regions are present on the same nucleic acid molecule, said nucleic acid target regions are separated from one another by at least 100, 200, 300, 500, 750, 1000, 2000, 5000, or 10000 nucleotides. Said protector molecule is preferably a Cas protein-gRNA complex when said nucleic acid molecule comprising the target region is greater than 300 bp in length.

According to a particular embodiment, when multiple target regions are isolated, the population of nucleic acid molecules may be contacted with more than one type of protector molecule. In one preferred embodiment, the more than type of one protector molecule comprises a combination of protector molecules, preferably both hairpin adaptors and site-specific endonucleases, such as Cas protein-gRNA complexes, more preferably Class 2 Cas protein-gRNA complexes.

The term "contacting" as used herein refers to placing of two or more molecules and/or products in a same solution such that said molecules and/or products may interact with one another. Contacting a population of nucleic acid molecules with a Class 2 Type V Cas protein-gRNA complex, for example, allows for the interaction of these molecules and the formation of complexes in which the Class 2 Type V Cas protein-gRNA complex has bound to the nucleic acid molecule at a specific site. Similarly, contacting a population of nucleic acid molecules with a protector molecule allows for the interaction of these molecules, and the binding of the protector molecule to the nucleic acid. "Binding" may more particularly refer to the hybridization of complementary nucleotides with the formation of hydrogen bonds (i.e. annealing), or any other covalent or non-covalent interactions. As a further example, "contacting" a molecule or product with an enzyme, such as an exonuclease, will result in an enzymatic reaction when said molecule or product is the substrate of said enzyme. For example, contacting a population of nucleic acid molecules with an enzyme having exonuclease activity will result in the digestion of nucleic acid molecules which correspond to the substrate of said enzyme and which are accessible to said enzyme.

Enzyme Having Exonuclease Activity

According to the methods described herein, after contacting a population of nucleic acid molecules with at least one Class 2 Type V Cas protein-gRNA complex and at least one protector molecule, said method further comprises the step of contacting the population of nucleic acid molecules with at least one enzyme having exonuclease activity. This step degrades nucleic acid molecules that are not protected by said Class 2 Type V Cas protein-gRNA-nucleic acid complex and said protector molecule, thereby increasing the ratio of target nucleic acid molecules as compared to non-target nucleic acid molecules. The skilled person will understand that this step must be performed posterior to step a) to prevent non-desired degradation of the nucleic acid target region.

The term "enzyme having exonuclease activity" as used herein refers to an enzyme having 5' to 3' and/or 3' to 5' exonuclease activity. Said enzyme having exonuclease activity may be an exoribonuclease or an exodeoxyribonuclease or both. Said enzyme may recognize double-stranded or single-stranded nucleic acid molecules, or both. Said enzyme having exonuclease activity may or may not have one or more additional enzymatic activities (e.g. specific or non-specific endonuclease activity). As a non-limiting example, enzymes having exonuclease activity that may be used in the invention include lambda (A) exonuclease (also referred to herein as λ exo), exonuclease I (Exo I), exonuclease Ill (Exo III), exonuclease VII, 51 nuclease, exonuclease T, T5 exonuclease, T7 exonuclease, RecBCD nuclease, RecJf, Mung bean exonuclease, RNase D, RNase R exoribonuclease I, exoribonuclease II, and the like. Enzymatic degradation may be partial (i.e. non-protected nucleic acid regions or molecules may be present in the population even after the population has been contacted with an enzyme having exonuclease activity) or complete. This may depend on incubation conditions, sample composition, the nucleic acid population itself (e.g. nucleic acid structures), or other variables as known to the skilled person. Thus, the term "degrading" comprises at least partially degrading the nucleic acid molecules that are not protected.

According to a preferred embodiment, said enzyme having exonuclease activity does not have endonuclease activity. This may be advantageous when the target region comprises a site that may be recognized by a site-specific endonuclease, or when the target region is susceptible to degradation by a non-specific endonuclease. According to a preferred embodiment, said at least one enzyme having exonuclease activity is A exonuclease, exonuclease I (Exo I), exonuclease III (Exo III), exonuclease VII, exonuclease T, T5 exonuclease, T7 exonuclease, 51 nuclease, RecBCD nuclease, RecJf, RNase D, RNase R exoribonuclease I, exoribonuclease II, preferably λ exonuclease or Exo I, more preferably a combination of one or more thereof, even more preferably both A exonuclease and Exo I.

Recovering the Nucleic Acid Comprising a Target Region for Isolation

The Class 2 Type V Cas protein-gRNA complex stably and tightly binds to a nucleic acid sequence to form a Class 2 Type V Cas protein-gRNA-nucleic acid molecule complex. As this binding may prevent the nucleic acid comprising the target region from interacting with other compounds (e.g. proteins, polypeptides, nucleic acid molecules), it is advantageous to separate the nucleic acid molecule from the Class 2 Type V Cas protein-gRNA-nucleic acid molecule complex for ease of use in downstream methods. It is preferable to remove the Class 2 Type V Cas protein and the gRNA complex from solution, for example by degradation of these elements or further purification of the nucleic acid molecule comprising the target region. As a non-limiting example, the nucleic acid molecule comprising the target region may be recovered from the Class 2 Type V Cas protein-gRNA-nucleic acid complex by contacting the nucleic acid molecules with at least one protease. This degrades the Class 2 Type V Cas protein and any other proteins that may be present (i.e. protector molecules, such as Class 2 Cas protein-gRNA complexes, or contaminating proteins that are remain from the initial sample). As a non-limiting example, the protease may be selected from serine proteases, cysteine proteases, threonine proteases, aspartic proteases, glutamic proteases, metalloproteases, and/or asparagine peptide lyases.

Additionally, or alternatively, the nucleic acid molecule comprising the target region may be recovered from the Class 2 Type V Cas protein-gRNA-nucleic acid complex by contacting the nucleic acid molecules with a compound capable of chelating divalent cations (in particular $Mg^{2+}$), such as EDTA or EGTA.

According to a preferred embodiment, recovery of said nucleic acid molecule comprising the target region is performed by contacting the Class 2 Cas protein-gRNA-nucleic acid molecule complex with a chelator of divalent cations, preferably a chelator chelating Mg2+ cations. Preferably, said chelator is EDTA or EGTA. Preferably, the quantity of EDTA or EGTA added is at least 2-fold greater than the quantity of divalent cations to be chelated, more preferably at least 3-fold, 4-fold, 5-fold greater, even more preferably at least 10-fold greater than the quantity of divalent cations. The skilled person can easily determine the appropriate quantity of chelator in view of the composition of the solution comprising the population of nucleic acid molecules (e.g. according to the presence and quantity of cations), and in further view of the embodiments provided herein. According to a particular example, EDTA is added at a concentration of at least 20 mM, more preferably at least 25 mM. In cases where at least one protease and a chelator of divalent cations are used in step c), said at least one protease and chelator of divalent cations may be added simultaneously wherein said chelator does not inhibit the activity of said at least one protease.

Additionally, or alternatively, the nucleic acid molecule comprising the target region may be recovered from the Class 2 Type V Cas protein-gRNA-nucleic acid complex (and protector molecule, if applicable) by contacting the nucleic acid molecules with at least one RNase, such as RNaseA, RNase H, or RNase I. This degrades the gRNA. In another embodiment, as RNA is unstable at elevated temperatures, the sample may be heated (e.g. to at least 65° C.), optionally in the presence of divalent metal ions and/or under alkaline pH.

In some embodiments, the recovered nucleic acid molecule comprising the target region is further purified, for example using paramagnetic beads.

Polymerization

According to the method provided herein, after recovering the nucleic acid molecule comprising the target region, said nucleic acid molecule is contacted with a processive polymerase. The term "processive polymerase" as used herein refers to a polymerase that is able to catalyze the incorporation of successive nucleotides without releasing the template strand. Without being limited by theory, said processive polymerase may repair any overhangs present at the ends of the nucleic acid molecule comprising the target region (this step may therefore also be referred to interchangeably herein as the "end repair" step). Preferably said processive polymerase has at least 3' to 5' processive activity and is therefore able to repair (or "fill-in") 5' overhangs, generating double-stranded regions. In the absence of proofreading activity (e.g. use of a 3' to 5' exonuclease deficient processive polymerase), a nucleic acid molecule comprising a 3' overhang consisting of a single base (generally adenine) may be obtained. According to a preferred embodiment, said processive polymerase is preferably a mesophilic or thermophilic polymerase, even more preferably a T4 DNA polymerase.

"End repair" as used herein thus refers to the process resulting in both strands of a double stranded nucleic acid molecule terminating at a base pair, also referred to as a blunt end. End repair may be performed on a 5' and/or 3' overhang, preferably a 5' overhang. End repair is preferably performed using a processive polymerase, as described above. Preferably, end repair is performed by contacting a nucleic acid molecule comprising 5' overhangs with a processive polymerase and dNTPs in an appropriate buffer. The skilled person is well aware of what end repair corresponds to in view of their general knowledge.

A "mesophilic polymerase" as used herein refers to a polymerase which has notably been isolated from a mesophilic microorganism (i.e. growing optimally at a temperature comprised between 20° C. and 45° C.) or derived from said isolated polymerase. Said polymerase may be a DNA or RNA polymerase, as appropriate in view of the nucleic acid substrate. When the nucleic acid molecule is DNA, the polymerase is preferably a mesophilic DNA polymerase. Generally, the mesophilic polymerase will have polymerase activity at or below a temperature of about 37° C., for example between about 12° C. and 37° C. Examples of mesophilic polymerases include, for example, Pol I, Klenow, Klenow exo-, M-MuLV, phi 29, T4, T5, and T7 (both RNA and DNA polymerases).

In contrast to a mesophilic polymerase, "thermophilic polymerases" have a higher optimum temperature for polymerase activity (e.g. comprised between 45 and 80° C.) and a greater resistance to heat inactivation than mesophilic polymerases. However, the term thermostable polymerase as used herein does not necessarily refer to an enzyme that is totally resistant to heat inactivation. Thus, heat treatment may reduce thermophilic polymerase activity to some extent. As an example, the mesophilic T5 DNA polymerase 3'-to-5' activity is totally inactivated by exposing the enzyme to a temperature of 90° C. for 30 seconds, whereas a thermophilic DNA polymerase, such as the Taq polymerase, has a half-life of over 6 hours at 95° C. In the present context, the nucleic acid molecule comprising the target region is not denatured. Preferably, when contacting the nucleic acid molecule comprising the target region with a polymerase, said step of contacting occurs at a temperature of less than or equal to 80° C., preferably less than or equal to 75° C., 70° C., 60° C., even more preferably less than or equal to 50° C. According to a particular embodiment, said nucleic acid molecule comprising the target region is contacted with a polymerase at 50° C. for 20 minutes.

As is understood by the person skilled in the art, polymerase activity requires the presence of nucleotides (e.g. the four nucleotides dATP, dTTP, dGTP, and dCTP for DNA polymerases and ATP, UTP, CTP and GTP for RNA polymerases). Polymerization reactions may further be performed in the presence of a variety of reagents, including buffers, salts, and the like, as are known to the skilled person.

In some embodiments, the nucleic acid molecule comprising the target region which has undergone end repair is further purified, for example using paramagnetic beads.

Optional Supplementary Steps

Fragmentation

According to a particular embodiment of the invention, nucleic acid molecules may be fragmented before or after being contacted with the Class 2 Type V Cas protein-gRNA complex and protector molecule in the above method, advantageously after being contacted with the Class 2 Type V Cas protein-gRNA complex. The term "fragmentation" as used herein refers to an increase in the number of nucleic acid molecule 5'- and 3'-free ends by breaking a nucleic acid molecule into at least two smaller molecules. Nucleic acid fragmentation is advantageous as the efficiency of exonuclease digestion in the present method may be improved. Indeed, exonuclease activity can only be initiated from a 5'- and/or a 3'-free end, as defined above.

Fragmentation may be performed by shearing, for example by sonication, hydro-shearing, ultrasound, nebulization or by enzymatic fragmentation, for example by using one or more site-specific endonucleases, such as restriction enzymes. At least 2, 3, 4, 5, or more, site-specific endonucleases may be used. It will be understood that the ever-increasing number of sequences available in the databases enables the skilled person to easily identify one or more restriction enzymes whose cleavage sites are located outside of the nucleic acid comprising the target region. Advantageously, when 2 or more enzymes are used concomitantly, said enzymes are compatible to one another (e.g. same buffer requirements, inactivation conditions). Fragmentation may be partial (e.g. not all cleavage sites present in the nucleic acid molecules of the population are cut by the restriction enzyme) or complete. Thus, the term "fragmentation" comprises at least partially fragmenting the nucleic acid molecules and regions that are not flanked by the Class 2 Type V Cas protein-gRNA-nucleic acid molecule complex and protector molecule.

These nucleic acid molecules or sequences may also be referred to herein as "unprotected" molecules or regions.

Thus, in some embodiments, the method of preparing a nucleic acid comprising a target region further comprises the step of:

fragmenting unprotected regions, preferably by contacting the population of nucleic acid molecules with at least one site-specific endonuclease, more preferably with at least one restriction enzyme.

The skilled person will understand that the above step of fragmenting occurs after contacting the nucleic acid molecule comprising the target region with the Class 2 Type V Cas protein-gRNA complex and protector molecule. However, in some cases the step of fragmenting may occur prior to or simultaneously to contacting a population of nucleic acid molecules with the Class 2 Type V Cas protein-gRNA complex and/or protector molecule. This is notably the case when said site-specific endonuclease cleaves in the same conditions (e.g. buffer, temperature) as the Class 2 Type V Cas protein-gRNA complex or protector molecule.

If one or more circular nucleic acid molecules are present in the sample, fragmentation will advantageously linearize said nucleic acid molecules, thereby generating free ends which may then be targeted for degradation. When circular nucleic acid molecules are present, fragmentation is preferably performed before, or simultaneously to either step a) or b) of the method of preparing a nucleic acid molecule comprising a target region as described herein.

According to a preferred embodiment, nucleic acid molecules are fragmented by contacting the population of nucleic acid molecules with at least one site-specific endonuclease, preferably at least 2, 3, 4, 5, or more, site-specific endonucleases. Preferably, said site-specific endonuclease is a restriction enzyme, more preferably a Type II, Type III, or artificial restriction enzyme, even more preferably a Type II restriction enzyme, and/or a Class 2 Type V Cas protein-gRNA complex, such as a Cpf1-gRNA complex. Type II restriction enzymes include Type IIP, IIS, IIC, IIT, IIG, IIE, IIF, IIG, IIM, and IIB categories, as described for example in Pingoud and Jeltsch, *Nucleic Acids Res,* 2001, 29(18): 3705-3727. Preferably, one or more enzymes from these categories are used to fragment nucleic acid molecules in the present invention. Appropriate enzymes can be selected by the skilled person. In cases where multiple restriction enzymes that are not compatible with one another are used, fragmentation may comprise multiple sequential steps, using different restriction enzymes and conditions (e.g. temperature, time, buffer). Preferably, the at least one site-specific endonuclease generates non-palindromic overhangs. Preferably, at least 50%, 60%, 70%, 80%, 90%, 95%, or 100% of cleavage sites are cleaved by the site-specific endonuclease(s). In cases where the site-specific endonuclease is a Class 2 Type V Cas protein-gRNA complex, said protein-gRNA complex binds and cleaves at a site exterior to the nucleic acid molecule comprising the target region that is being prepared. Preferably, site-specific endonuclease(s) bind a sequence that is located 100 to 5000 bases from the nucleic acid comprising a target region, more preferably 150 to 1000 bases from the nucleic acid region comprising the target region, even more preferably 250-750 bases from a nucleic acid region comprising a target region. Preferably, the site-specific endonuclease targets a specific sequence that is present multiple times within the nucleic acid molecule(s), such as the Alu element in the human genome, but that is absence from the nucleic acid molecule comprising the target region.

According to a particular embodiment, after contacting the population of nucleic acid molecules with a Class 2 Type V Cas protein-gRNA complex and protector molecule, said population is simultaneously contacted with at least one enzyme having exonuclease activity and at least one site-specific endonuclease fragmenting said nucleic acid molecule according to any of the embodiments described above. This is particularly advantageous, as it reduces the duration of the method. According to another preferred embodiment, said enzyme having exonuclease activity may also have site-specific endonuclease activity. According to this embodiment, the cleavage site(s) of the enzyme having site-specific endonuclease activity is/are located outside of nucleic acid molecule comprising the target region. The use of a single enzyme having both exonuclease and site-specific endonuclease activity is particularly advantageous as it reduces the number of reagents required and cost.

Incubation and/or Storage

According to a particular embodiment of the invention, nucleic acid molecules may be stored after step c) of the above method. According to a particular embodiment, nucleic acid molecules may be incubated during or after being contacted with the Class 2 Type V Cas protein-gRNA complex and protector molecule, during or after being contacted with at least one enzyme having exonuclease activity, during recovery of the nucleic acid molecule comprising the target region, and/or during or after being contacted with the processive polymerase in the above method. Preferably, the nucleic acid molecule is incubated for 30 minutes to two hours.

Isolation of the Target Region

A nucleic acid molecule comprising a target region that has been prepared according to the above-described method may be considered to have undergone a first round of isolation or enrichment. The nucleic acid molecule comprising a target region that has been prepared with the above-described method may then be used in downstream methods, such as, but not limited to, further isolation or enrichment methods. Indeed, in cases where high levels of isolation or enrichment of a nucleic acid target region are required, the nucleic acid molecule obtained with the above-described method is advantageously isolated of said target region.

Thus, in another aspect, the invention relates to a method of isolating a nucleic acid target region from a nucleic acid molecule wherein said nucleic acid molecule has been prepared using any of the methods of preparing as described above. Surprisingly, the inventors found that when this method of isolating a nucleic acid target region is performed downstream of the above-described method of preparing, efficacy is improved. More specifically, the inventors have surprisingly shown that efficacy is improved by at least 10,000-fold when isolation is performed on a nucleic acid molecule comprising a target region prepared according to the method described above (in particular comprising a step of contacting the nucleic acid molecule with a processive polymerase).

The method described herein furthermore retains many additional advantages. Firstly, all characteristics of the nucleic acid target region (e.g. chemical modifications, mismatches) are conserved. This method may furthermore be advantageously used to isolate target regions from small sample sizes or to isolate target regions from samples having low levels of said target regions. This method of isolation remains quick and inexpensive, may be performed directly on nucleic acid molecules prepared using the above-described method, has few processing steps, and is relatively simple. Advantageously, all steps may be performed in the same container. Thus, sample loss is minimal in the absence of material transfer between containers. In the absence of any amplification steps in this method of isolation, bias in downstream methods may also be reduced. In addition, multiplex assays using multiple Class 2 Cas proteins for the isolation of multiple target regions can be easily designed with no risk of primer interactions or cross-recognition. Finally, this method advantageous as it is compatible with existing downstream nucleic acid analysis platforms, including "second" and "third-generation" sequencing technologies, wherein single nucleic acid molecules are analysed within micro-structures, such as nanopores, zero-mode wave guides, or microwells. Advantageously, the present method provides isolated nucleic acid target regions that comprise single-stranded nucleic acid overhangs on either or both ends, onto which various adaptors or linkers can be specifically ligated, enabling the target region(s) to be used in a wide variety of downstream analyses and applications.

Said method of isolating a nucleic acid target region more particularly comprises the following steps:

a) providing a nucleic acid molecule comprising a nucleic acid target region wherein said nucleic acid molecule has been prepared using the above-described method of preparing,
b) contacting said nucleic acid molecule with a Class 2 Cas protein-gRNA complex, wherein said gRNA comprises a guide segment that is complementary to a third sequence, said third sequence being between the first sequence and the first protector molecule, thereby forming a Class 2 Cas protein-gRNA-nucleic acid complex,
c) optionally, contacting said nucleic acid molecule with a second protector molecule, said second protector molecule preferably being a second Class 2 Cas protein-gRNA complex, wherein said gRNA comprises a guide segment that is complementary to a fourth sequence, thereby forming a second Class 2 Cas protein-gRNA-nucleic acid complex, said fourth sequence being between the first sequence and the first protector molecule, wherein said third and fourth sequences are preferably comprised in said target region,
d) contacting said nucleic acid molecule with at least one enzyme having exonuclease activity, and
e) recovering the isolated nucleic acid target region from the Class 2 Cas protein-gRNA-nucleic acid complex(es).

In the context of the specific method of isolation described above, the steps are performed sequentially in the order provided, with step a) performed first and step e) performed last. Steps b) and c) of the method above may be performed in any particular order, as long as they are performed prior to step d). Indeed, step b) may be performed before step c), step c) may be performed before step b), or both steps may be performed simultaneously. Steps d) and e) are performed sequentially. In some cases, additional optional steps may be included in the method, as indicated below. The skilled person will further understand that more than one nucleic acid molecule comprising a target region may have been prepared, and that the present method of isolating may therefore also comprise the isolation of more than one nucleic acid target region (e.g. 2, 5, 10, 20, 50, 100, etc. different target regions).

As indicated above, the inventors have surprisingly shown that efficacy may be improved by at least 10,000-fold when the present method is used in combination with the above-described method of preparing a nucleic acid comprising a target region for isolation, wherein said method comprises a step of contacting the nucleic acid molecule with a processive polymerase (i.e. end repair). Without being limited by theory, the improved efficacy observed when using the above-described method of preparing a nucleic acid coupled with the presently described method of isolation, may be due to blunting the 5' single-stranded overhang that may be generated when the nucleic acid strand comprising the PAM dissociates from the Class 2 Type V Cas protein-gRNA-nucleic acid complex during step a) and/or b) of the above method of preparing a nucleic acid comprising a target region. In this case, the strand comprising the PAM may not be protected from exonuclease digestion when the Cas protein-gRNA-nucleic acid complex is contacted with at least one enzyme having exonuclease activity in step b), thereby leading to the generation of 5' overhangs which are resistant to exonuclease treatment. The removal of these overhangs in step d) of the above method of preparing may advantageously prepare the nucleic acid molecule comprising a target region for use in downstream methods, in particular for use in the present method of isolating a target region.

The term “isolation” or “isolating” as used herein refer to an increase in the proportion of one or more target nucleic acid regions with respect to one or more other regions or molecules in a sample. As a non-limiting example, these other molecules may comprise proteins, lipids, carbohydrates, metabolites, nucleic acids, or combinations thereof. As a non-limiting example, these other regions may correspond to nucleic acid regions present on the same molecule as, or even adjacent to, said target region but that are not comprised in the target region. As a particular example, the repaired ends of the nucleic acid molecule prepared in the above method of preparing may not be comprised in the target region. In some cases, a 5' or 3' overhang may be comprised in the isolated nucleic acid comprising the target region (i.e. if only a single exonuclease digesting a single strand of a double stranded nucleic acid is used). Preferably, said overhang is 100 to 700 nucleotides in length. In another example, when the target region corresponds to a gene, adjacent non-coding regions are not comprised in the target region. As an alternative non-limiting example, the target region may further comprise up to 50 bases adjacent to the PAM sequence. The “isolation” of the target nucleic acid region, as used herein, may refer more specifically to an increase in the proportion of the one or more target nucleic acid regions in a sample by at least 2-fold (e.g. 2, 3, 4, 5, 10, 20, 30, 40, 50, 60, 70, 80, 90, 100, 250, 500, 750, 1000, or 10,000-fold or more), as compared to the one or more other molecules in a sample, or as compared to the total number of molecules in the initial sample (i.e. prior to performing both the methods of preparing and isolating a target region of the invention). Isolation of the target nucleic acid region may also refer to an increase in the proportion of the target nucleic acid region in the sample by at least 5% (e.g. 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%) when compared to the level of the one or more other molecules in a sample. When the proportion of the target nucleic acid region is 100%, no other molecules are comprised in the sample. The term “enrichment” as used herein refers more specifically to the isolation of one or more target nucleic acid regions with respect to the other nucleic acid molecules in the sample. As an example, enrichment of the target region refers to an increase in the proportion of the isolated target region as compared to the amount of total initial nucleic acid, wherein the proportion of the isolated target region is increased by at least 10%, 20%, 30%, 40%, 50%, 60%, 65%, 70%, 75%, 80%, 85%, 90%, 95%, 96%, 97%, 98%, 99% or 100%. According to a preferred embodiment, the proportion of the isolated target region, as compared to the amount of total initial nucleic acid is increased by at least 10%, more preferably at least 20%, at least 30%, at least 40%, at least 50%, at least 60%, at least 65%, at least 70%, at least 75%, at least 80%, at least 85%, at least 90%, at least 95%, at least 96%, at least 97%, at least 98%, even more preferably at least 99% or 100%.

According to one embodiment, the isolated nucleic acid target region is enriched by at least 10-fold, at least 20-fold, at least 50-fold, at least 100-fold, at least 250-fold, at least 500-fold, at least 750-fold, preferably by at least 1000-fold, at least 10,000-fold, at least 100,000-fold, even more preferably by at least 1,000,000-fold, at least 2,000,000-fold, or at least 3,000,000-fold. As a particular example, the 100% enrichment of a single 1 kb fragment from a population of nucleic acid molecules equivalent to the human genome of approximately 3.2 billion bp represents a 3,000,000-fold increase. According to an alternative embodiment, the isolated target region is substantially pure. By "substantially pure" is meant that the isolated target region comprises at least 99%, preferably at least 99.5%, of the total nucleic acid in the sample following isolation of the target region according to the method of the present invention.

According to a preferred embodiment, the target region of interest comprises less than 10% of the total nucleic acid in the initial sample (e.g. prior to both preparing the nucleic acid comprising the target region and isolating the target region), preferably less than 5%, more preferably less than 2%, less than 0.05%, less than 0.02%, even more preferably less than 0.01%, less than 0.005%, less than 0.001%, less than 0.0005%, less than 0.0001%, less than 0.00005%, less than 0.00001%, or less than 0.0000005%. The skilled person will realize that the amount or percent of the target region of interest within the total nucleic acid of a sample will vary depending on the number of target regions to be isolated and the length of the target regions(s) to be isolated. As a non-limiting example, a 1 kb target region of interest within the human genome of approximately 3.2 billion bp represents less than 0.0000005% of the total genome.

Any of the ratios of the number of molecules of nucleic acid comprising a target region:Cas protein:gRNA described above in relation to the method of preparing may also be used in the present method of isolating a target region as concerns the ratio of the number of nucleic acid target regions:Cas protein (preferably Class 2 Cas protein):gRNA. Preferred ratios may correspond to any of the ratios provided previously.

The first step (step a)) of the present method of isolating a nucleic acid molecule comprises providing at least one nucleic acid molecule comprising a nucleic acid target region, said nucleic acid molecule having been prepared according to the above-described method of preparing. Said nucleic acid molecule comprises a target region and flanking region(s), said flanking region(s) comprising at least a first sequence to which the Class 2 Type V Cas protein-gRNA complex was bound during the method of preparing. Said first sequence is at least partially complementary to the guide segment of the gRNA comprised in the Class 2 Type V Cas protein-gRNA complex. Depending on whether the protector molecule provided in the method of preparing (i.e. the first protector molecule) is a second site-specific endonuclease or a hairpin, the nucleic acid molecule comprising the target region may comprise a second sequence that is at least partially complementary to the guide segment of the gRNA comprised in the Class 2 Type V Cas protein-gRNA complex or not. Indeed, when the protector molecule is a hairpin, said hairpin may bind to a blunt end or an overhang. Thus, a hairpin need not necessarily bind to a specific sequence. Preferably, the hairpin will bind to a free end, as described previously in the context of the method of preparing. In contrast, when the protector molecule is a site-specific endonuclease, said site-specific endonuclease preferably binds to a second sequence, wherein said first and second sequences flank the target region to be isolated.

In the context of the present method of isolating a target region, said nucleic acid molecule comprising a target region obtained from the method of preparing is contacted with a Class 2 Cas protein-gRNA complex, wherein said gRNA comprises a guide segment that is complementary to a third sequence. In the present context, said third sequence is located between the first sequence and the protector molecule of the method of preparing. In cases where the protector molecule is no longer present (i.e. the protector molecule is no longer associated with the nucleic acid molecule prepared by the above-method of preparing), the location of the third sequence is described in reference to where said protector molecule was previously bound during the method of preparing. In other words, said third sequence is located between the first sequence and the protector molecule, more particularly between the first sequence and the second sequence to which the protector molecule previously bound when said protector molecule itself (i.e. a Class 2 Cas protein-gRNA complex) is no longer present. Thus, said third sequence is located within the nucleic acid molecule prepared in the above-described method of preparing. Preferably, said third sequence binds to the target region.

General descriptions of Cas proteins, gRNA, and PAMs as provided above in the context of the method of preparing also apply to the present method of isolating. Indeed, the Class 2 Cas protein used in the present method of isolating may notably be any Class 2 Cas protein described above, preferably a Class 2 Type V or a Class 2 Type II Cas protein. Preferably, said Class 2 Cas protein is selected from one of the following species: *Streptococcus pneumoniae, Streptococcus pyogenes, Streptococcus thermophilus, Streptococcus canis, Staphylococcus aureus, Neisseria meningitidis, Treponema denticola, Francisella tularensis, Francisella novicida, Pasteurella multocida, Streptococcus mutans, Campylobacter jejuni, Campylobacter lad, Mycoplasma gallisepticum, Nitratifractor salsuginis, Parvibaculum lavamentivorans, Roseburia intestinalis, Neisseria cinerea, Gluconacetobacter diazotrophicus, Azospirillum, Sphaerochaeta globosa, Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pasteuri, Filifactor alocis, Veillonella* sp. *Suterella wadsworthensis, Leptotrichia* sp., *Corynebacterium diphtheriae, Acidaminococcus* sp., or Lachnospiraceae sp., *Prevotella albensis, Eubacterium eligens, Butyrivibrio fibrisolvens, Smithella* sp., *Flavobacterium* sp., *Porphyromonas crevioricanis*, or Lachnospiraceae *bacterium* ND2006, more preferably from *Streptococcus pyogenes, Neisseria meningitidis, Streptococcus thermophiles*, or *Treponema denticola*, even more preferably *Streptococcus pyogenes*. Preferably, said Class 2 Cas protein is selected from one of the following proteins J3F2B0, Q0P897, Q6NK13, A0Q5Y3, Q927P4, A11Q68, C9X1G5, Q9CLT2, J7RUA5, Q8DTE3, Q99ZW2, G3ECR1, Q73QW6, G1UFN3, Q7NAI2, E6WZS9, A7HP89, D4KTZ0, DOW2Z9, B5ZLK9, F0RSV0, A0A1L6XN42, F2IKJ5, S0FEG1, Q6KIQ7, A0A0H4LAU6, F5X275, F4AF10, U5ULJ7, D6GRK4, D6KPM9, U2SSY7, G4Q6A5, R9MHT9, A0A111NJ61, D3NT09, G4Q6A5, A0Q7Q2, or U2UMQ6 (accession numbers are from UniProt (www.uniprot.org), version last modified on Jan. 10, 2017). The term "Class 2 Cas protein" as used in the context of the specific method of isolating a nucleic acid target region may refer to any Class 2 Cas protein described herein, said Class 2 Cas protein forming a complex with a gRNA as described herein. Preferably, the gene encoding the Class 2 Cas protein is any gene comprising a nucleotide sequence wherein said sequence generates the amino acid sequence of the corresponding Cas protein, such as one of those listed above.

Preferably, said Class 2 Cas protein is Cas9, Cpf1, C2c1, C2c3, or C2c2, preferably Cas9 or Cpf1, even more preferably Cas9. While said Class 2 Cas protein may be catalytically active, a nickase, or catalytically dead, said Class 2 Cas protein is preferably catalytically dead. Indeed, without being limited by theory, the use of a catalytically dead enzyme is particularly advantageous as such a Cas protein will have no impact on the structure of the ends of said nucleic acid molecule, as no cleavage is performed. Thus, the structure of the ends of the nucleic acid molecule (i.e. blunt end, 5' overhang, or 3' overhang) may be selected by incubation of said nucleic acid molecule with an appropriate enzyme comprising exonuclease activity, as is described below.

In the context of the present method of isolating a target region, said nucleic acid molecule comprising a target region may be contacted with a protector molecule, specifically a second protector molecule (in contrast to the first protector molecule used in the above-referenced method of preparing). The second "protector molecule" of the present method of isolating a target region may correspond to any of the protector molecules described in relation to the previously described method of preparing a nucleic acid molecule comprising a target region. Thus, the Class 2 Cas protein-gRNA complex, and optional second protector molecule protect the target region from downstream degradation by one or more enzymes having exonuclease activity.

The use of a second protector molecule is optional in the present method of isolation. As a non-limiting example, the nucleic acid molecule comprising a target region need not be contacted with a second protector molecule when a hairpin was previously used as a protector molecule in the method of preparing, as said hairpin will still be comprised in the nucleic acid molecule comprising the target region prepared according to the above method of preparing. Indeed, a hairpin is not susceptible to exonuclease activity or polymerization performed in nondenaturing conditions, and will therefore remain as part of the nucleic acid molecule comprising the target region. As a further non-limiting example, a second protector molecule may not be necessary in cases where a target region may be protected by a single Class 2 Cas-protein-gRNA complex (e.g. said target region forms a complex with the Class 2 Cas protein-gRNA forming a Class 2 Cas protein-gRNA-nucleic acid complex). In a particular embodiment, said target region preferably has a length of less than 44 nucleotides or bp. Alternatively, in cases where the method of preparing comprised contacting the population of nucleic acid molecules with a protector molecule, wherein said protector molecule is a site-specific endonuclease, the nucleic acid molecule comprising a target region is preferably contacted with a second protector molecule in the present method of isolating a target region. In cases where the protector molecule used in the present method of isolating a target region is a second Class 2 Cas protein-gRNA complex, said gRNA preferably comprises a guide segment that is complementary to a fourth sequence within the nucleic acid molecule that is prepared using the above-described method of preparing. In the present context and like the third sequence, said fourth sequence is also located between the first sequence and the protector molecule as described above in relation to the method of preparing. In cases where the protector molecule is no longer present (i.e. the protector molecule is no longer associated with the nucleic acid molecule prepared by the above-method of preparing), the location of the fourth sequence is also described in reference to where said protector molecule was previously bound during the method of preparing, and as is described above for the third sequence. Preferably, said third sequence and said fourth sequence are comprised within said target region. Preferably, said third and fourth sequences are nested between said first sequence and protector molecule, more particularly between said first sequence and second sequence when said protector molecule is a site-specific endonuclease. Preferably, said third sequence is located less than 1000, 750, 600, 500, 400, 300, 200, more preferably less than 100 nucleotides from said first sequence, and optionally said protector molecule or second sequence. Preferably, said fourth sequence is located less than 1000, 750, 600, 500, 400, 300, 200, more preferably less than 100 nucleotides from said protector molecule or said second sequence. Of course, said third and fourth sequences may be located adjacent to said first sequence and said protector molecule as described herein. Indeed, the terms first, second, third, and fourth are simply meant to specify different nucleic acid sequences with no specific orientation or directionality as regards the other sequences (unless specifically indicated). Said third and fourth sequences are preferably located at each extremity of a target region. The term "extremity" as used herein refers to an outer boundary of the target region, which need not necessarily correspond to a free end. Indeed, in most cases, said target region will be comprised within a longer nucleic acid molecule (see also FIG. 1E or FIG. 2A (v), for example, where the sequences bound by the Cas9-gRNA complexes correspond to the extremities of the target region). In some cases, said third sequence (and optionally, said fourth sequence) may correspond to a target region. Said third and fourth sequences are preferably protected from degradation by binding of a Class 2 Cas protein-gRNA complex to each sequence. In this case, the target region is advantageously directly protected in its entirety. In other cases, said target region is preferably isolated using two different Class 2-gRNA complexes, said gRNAs respectively being at least partially complementary a third sequence and a fourth sequence, as described above.

In the context of the present method of isolating a target region, said nucleic acid molecule comprising a target region is contacted with at least one enzyme having exonuclease activity. Said at least one enzyme having exonuclease activity corresponds to any of the embodiments defined above in relation to the method of preparing. Any of the enzymes described previously in relation to the method of preparing may also be used in the present method of isolating a target region. Preferably, said at least one enzyme having exonuclease activity is λ exonuclease, exonuclease I (Exo I), exonuclease III (Exo III), exonuclease T, T5 exonuclease, T7 exonuclease, 51 nuclease, RecBCD nuclease, RecJf, RNase D, RNase R exoribonuclease I, exoribonuclease II, preferably a combination of two or more thereof. The use of a single exonuclease (e.g. λ exonuclease or Exo III) is advantageous as, in addition to the degradation of unprotected molecules, the ends of the nucleic acid target region may be simultaneously prepared for downstream applications, which may for example require the presence of 5' single-stranded overhangs (e.g. generated by Exo III) or 3' single-stranded overhangs (e.g. generated by λ exonuclease). Thus, according to a particular embodiment, said at least one enzyme having exonuclease activity is λ exonuclease or Exo III. In an alternative embodiment, an exonuclease specifically degrading double-stranded DNA, for example selected from those listed above, may be used. In an alternative embodiment, a combination of exonucleases specifically degrading double-stranded DNA and single-stranded DNA, for example a combination of exonucleases selected from those listed above, may be used.

In the context of the present method of isolating a target region, said nucleic acid target region is then recovered. Recovery may be performed according to any of the embodiments described previously in relation to the method of preparing. In particular, the target region may be recovered by contacting the nucleic acid molecule with at least one protease. Preferably, the protease may be selected from serine proteases, cysteine proteases, threonine proteases, aspartic proteases, glutamic proteases, metalloproteases, and/or asparagine peptide lyases.

Additionally, or alternatively, the target region may be recovered from the Class 2 Cas protein-gRNA-nucleic acid complex by contacting the nucleic acid target region with a compound capable of chelating divalent cations (in particular $Mg^{2+}$), such as EDTA or EGTA. Thus, according to a preferred embodiment, recovery of said target region is performed by contacting the nucleic acid target region with a chelator of divalent cations, preferably a chelator chelating $Mg^{2+}$ cations. Preferably, said chelator is EDTA or EGTA. Preferably, the quantity of EDTA or EGTA added corresponds to that described above in relation to the method of preparing. In cases where at least one protease and a chelator of divalent cations are used in step e), said at least one protease and said chelator of divalent cations are preferably added simultaneously wherein said chelator does not inhibit the activity of said at least one protease.

Additionally, or alternatively, the target region may be recovered by contacting the nucleic acid molecule with at least one RNase, such as RNaseA, RNase H, or RNase I. In another example, as RNA is unstable at elevated temperatures, the sample may be heated (e.g. to at least 65° C.), optionally in the presence of divalent metal ions and/or under alkaline pH.

In some embodiments, the target region of step b), c), or e) is further purified, for example using paramagnetic beads.

According to a particular embodiment, the method of isolating a nucleic acid target region according to the invention comprises the following steps:

- a) contacting a population of nucleic acid molecules with:
  - a first Class 2 Type V Cas protein-gRNA complex, wherein the gRNA comprises a guide segment that is complementary to a first sequence within a nucleic acid molecule, said first sequence being located adjacent to said target region, thereby forming a Class 2 Type V Cas protein-gRNA-nucleic acid complex, and
  - a first protector molecule, wherein said protector molecule is preferably a hairpin adaptor or a site-specific endonuclease, said site-specific endonuclease being more preferably a TALEN, a zinc-finger protein, or a Class 2 Cas protein-gRNA complex, even more preferably a Class 2 Type V or Class 2 Type II Cas protein-gRNA complex, wherein the gRNA comprises a guide segment that is complementary to a second sequence within the nucleic acid molecule, said second sequence being located adjacent to said target region and wherein said first sequence and said protector molecule (or said second sequence) flank said target region,
- b) contacting the population of nucleic acid molecules with at least one enzyme having exonuclease activity,
- c) recovering said nucleic acid molecule comprising the target region from at least the Class 2 Type V Cas protein-gRNA-nucleic acid complex formed in step a),
- d) contacting the nucleic acid molecule of step c) with a processive polymerase,
- e) contacting the nucleic acid molecule of step d) with a Class 2 Cas protein-gRNA complex, wherein said gRNA comprises a guide segment that is complementary to a third sequence, said third sequence being between said first sequence and said protector molecule, thereby forming a Class 2 Cas protein-gRNA-nucleic acid complex,
- f) optionally, contacting said nucleic acid molecule of step d) with a protector molecule, said protector molecule preferably being a second Class 2 Cas protein-gRNA complex, wherein said gRNA comprises a guide segment that is complementary to a fourth sequence, said fourth sequence being between the first sequence and the second sequence, thereby forming a Class 2 Cas protein-gRNA-nucleic acid complex,
- g) contacting the nucleic acid molecule with at least one enzyme having exonuclease activity, and
- h) recovering the isolated nucleic acid target region from at least the Class 2 Cas protein-gRNA-nucleic acid complex.

In the above method, said third and fourth sequences are comprised in the target region, more preferably said third and fourth sequences are located at the extremities of said target region such that said third and fourth Class 2 Cas protein-gRNA complexes form Cas protein-gRNA-nucleic acid complex at the extremities of said target region, thereby protecting said target region in its entirety. In the above method, steps e) and f) may be performed sequentially in any order or simultaneously.

According to a particular embodiment, the method of isolating a nucleic acid target region according to the invention comprises the following steps:

- a) contacting a population of nucleic acid molecules with:
  - a Cpf1-gRNA complex, wherein the gRNA comprises a guide segment that is complementary to a first sequence within a nucleic acid molecule thereby forming a Cpf1 protein-gRNA-nucleic acid complex, said first sequence being located adjacent to said target region, and
  - a second Cpf1-gRNA complex, wherein the gRNA comprises a guide segment that is complementary to a second sequence within the nucleic acid molecule thereby forming a second Cpf1 protein-gRNA-nucleic acid complex, said second sequence being located adjacent to said target region, wherein said first sequence and said second sequence flank said target region,
- b) contacting the population of nucleic acid molecules with at least one enzyme having exonuclease activity,
- c) recovering said nucleic acid molecule comprising the target region from the Cpf1 protein-gRNA-nucleic acid complexes formed in step a),
- d) contacting the nucleic acid molecule of step c) with a processive polymerase,
- e) contacting the nucleic acid molecule of step d) with a Cas9-gRNA complex, wherein said gRNA comprises a guide segment that is complementary to a third sequence thereby forming a Cas9-gRNA-nucleic acid complex, said third sequence being between said first sequence and said second sequence, and optionally, contacting said nucleic acid molecule with a second Cas9-gRNA complex, wherein said gRNA comprises a guide segment that is complementary to a fourth sequence thereby forming a Cas9-gRNA-nucleic acid complex, said fourth sequence being between the first sequence and the second sequence, wherein said third and fourth sequences are located at the extremities of said target region, f) contacting the nucleic acid molecule formed in step e) with at least one enzyme having exonuclease activity, and g) recovering the isolated nucleic acid target region from the Cas9 protein-gRNA-nucleic acid complexes formed in step e).

In this method, Cpf1 is preferably catalytically active. In this method, Cas9 is preferably catalytically dead. Preferably, steps a) to g) are performed sequentially in the order provided above.

A nucleic acid target region that has been isolated according to one of the methods described above is advantageously highly enriched. Isolated nucleic acids are particularly useful in a wide range of applications. Indeed, the nucleic acids isolated according to the present invention may be subject to further processing, reactions, or analyses, which may occur in the same container, or not. As an example, the nucleic acids isolated according to the present invention may be used for detection, cloning, sequencing, amplification, hybridization, cDNA synthesis, diagnostics and any other methods known to the skilled person which require nucleic acids. In some cases, the isolated nucleic acid target region may undergo a further method of isolation or enrichment, or purification, of said target region.

The present method is particularly suited for generating a library of hairpins following isolation of the one or more target regions, wherein each hairpin comprises at least one nucleic acid target region. This method is thus particularly convenient for detecting or determining the sequence of a target region of interest, e.g. a particular allele, isolated from an entire population of nucleic acid molecules, for example in a biological sample.

According to a preferred aspect of the invention, the method of the invention may further comprise additional steps. As a non-limiting example, the isolated nucleic acids may be further purified using well-known purification methods (e.g. bead or column purification, such as purification with paramagnetic beads) to remove proteins, such as the Class 2 Cas protein, salts, proteases, EDTA, excess oligonucleotides, etc. As a non-limiting example, nucleic acid molecules may be hybridized and/or ligated to the target region, single-stranded gaps in the nucleic acid molecule may be filled in by synthesis of the complementary strand, and/or strand displacement may be performed. These additional steps are particularly useful for generating a hairpin library, but may also be necessary when preparing the isolated nucleic acid for other downstream applications. In a particular example, when one or more double-stranded nucleic acid molecules are isolated according to the methods of the present invention, a hairpin molecule, as has been previously defined herein, may then then be ligated to one or both free ends of said molecule. Preferably, a hairpin is ligated to one free end of the isolated target nucleic acid molecule (see also FIG. 4). Preferably, at least one free end of said isolated target nucleic acid molecule comprises a 3' or 5' overhang. Preferably, said hairpin comprises a 3' or 5' overhang that is at least partially complementary to at least one of the 5' or 3' overhangs, respectively, of said isolated target nucleic acid molecule. Preferably, said hairpin is ligated to a 3' overhang on one end of the isolated target nucleic acid molecule. As an alternative example, the hairpin is advantageously ligated to a 3' overhang in presence of the FEN1 enzyme, which cleaves 5'DNA flaps. Indeed, the inventors have found that ligating the hairpin to a 3' overhang in presence of FEN1 promotes cleavage of protruding nucleotides present at the 5' end of the oligonucleotides in cases where catalytically active Cpf1 is used for the preparation of the fragment to be isolated. Indeed, in contrast to Cas9, Cpf1 does not always cleave at the same position. Following ligation of said hairpin, gap filling and ligation reactions are performed using methods well-known in the art.

Thus, according to a first embodiment, the method of the invention further comprises the step of:

hybridizing and/or ligating one or more single or double-stranded nucleic acid molecules to the isolated nucleic acid target region.

Preferably, said single or double-stranded nucleic acid molecule is hybridized to a 5'- or 3'-overhang of the target region. Following hybridization, ligation is preferably performed. In a particular embodiment, the method may comprise the steps of:

hybridizing at least one single-stranded nucleic acid molecule to the isolated target region, and ligating said extended single-stranded nucleic acid molecule to the double-stranded region.

However, ligation may also be performed directly without hybridization when a single-stranded nucleic acid molecule (e.g. an oligonucleotide) binds to a single-stranded region of the target that directly abuts a double-stranded region.

As the number of nucleotides protected by the Class 2 Cas protein may vary, said single-stranded nucleic acid molecule is preferably hybridized to a single-stranded region of the isolated nucleic acid target region that is located at least 50 nucleotides away from the double-stranded region.

According to another embodiment, the method comprises the steps of:

hybridizing at least one single-stranded nucleic acid molecule to the isolated target region, extending the single-stranded nucleic acid molecule to the double-stranded region, preferably by contacting said isolated target region with a nucleic acid polymerase, and ligating said extended single-stranded nucleic acid molecule to the double-stranded region.

According to a preferred embodiment, the at least one single-stranded nucleic acid molecule is hybridized and polymerized on a 3'-overhang. Preferably, ligation to the 5' end occurs when a Class 2 Cas protein nickase or a catalytically dead Class 2 Cas protein is used, more preferably a catalytically dead Class 2 Cas protein, even more preferably Cas9d. Preferably, said single-stranded nucleic acid molecule hybridizes to a region that is at least 50 nucleotides away from the PAM. Methods of hybridization, extension and ligation are well-known to the skilled person.

In some cases, any of the above embodiments may be repeated, for example to add a second single-stranded nucleic acid molecule to the isolated target region. Said second single-stranded nucleic acid molecule may be hybridized to the same strand or to the opposite strand, and may comprise a label or not. Said single-stranded nucleic acid molecule may by only partially complementary to the sequence of the isolated target region. Said single-stranded nucleic acid molecule may preferably comprise a spacer region, for example, a 12-carbon spacer, that does not bind to the isolated target region (e.g. is not complementary to the sequence of the isolated target region). Preferably, the single-stranded nucleic acid molecule(s) comprises a 5' phosphate group for ligation. Optionally, excess reagents, such as non-hybridized single-stranded nucleic acid molecules may then be eliminated. As an example, non-hybridized single-stranded nucleic acid molecules may be eliminated by contacting the sample comprising the isolated target region with an enzyme having 3' to 5-exonuclease activity, more preferably exonuclease I.

According to a preferred embodiment, after hybridization of the single-stranded nucleic acid molecule to the target region, the method of the invention further comprises the step of:

performing strand displacement on the isolated target region.

Methods of strand displacement are known in the art. This advantageously allows recovery of the target region, wherein said target region comprises a short 5'-overhang. Preferably, the length of said 5' overhang corresponds to the length of the sequence protected by the Cas9, more preferably said overhang is 23 to 25 nucleotides in length. An isolated target region having a 5'-overhang may then be used as a template to hybridize and ligate oligonucleotides, for example for the construction of hairpin structures. Strand displacement is preferably performed by incubating the isolated target region with the oligonucleotide and, optionally, a polymerase, preferably at room temperature. According to a particular embodiment, strand displacement may be performed in the presence of RecA.

Preferably, strand displacement is performed when one strand of the target region has been nicked by a Class 2 Cas protein nickase.

After strand displacement, excess single-stranded nucleic acid molecules and the strand displacement product may be eliminated. Thus, according to a preferred embodiment, the method further comprises the step of:

eliminating excess single-stranded nucleic acid molecules and the strand displacement product.

According to a preferred embodiment, said excess single-stranded nucleic acid molecules and strand displacement product are eliminated by contacting the target region with an enzyme having 3' to 5-exonuclease activity, more preferably exonuclease I. Advantageously, excess single-stranded nucleic acid molecules and strand displacement product are specifically eliminated, with no effect on double-stranded target region, or on the 5'-overhangs.

According to a preferred embodiment, one or more single-stranded nucleic acid molecules may then be hybridized and ligated to the 5'-overhang of the target region. Preferably, ligation to the 5' overhang occurs after strand displacement, and optionally, after elimination of the excess single-stranded nucleic acid molecules and the strand displacement product. This advantageously generates a hairpin structure which is particularly adapted for use in downstream applications, such as those described in WO 2011/147931, WO 2011/147929, WO 2013/093005, and WO 2014/114687, incorporated herein by reference in their entirety. Alternatively, the hairpin structure generated here may be particularly adapted for use as a hairpin precursor molecule (e.g. the HP2 molecule described in WO 2016/177808, incorporated herein by reference in its entirety).

Preferably, the one or more single-stranded nucleic acid molecules of any of the above embodiments has optimized hybridization specificity as described in Zhang et al., *Nat Chem,* 2012, 4(3):208-214, incorporated herein by reference in its entirety. Alternatively, said one or more single-stranded nucleic acid molecules of any of the above embodiments may be degenerate.

Preferably, the one or more single-stranded nucleic acid molecules of any of the above embodiments comprises a label. As a non-limiting example, the label may be FITC, digoxigenin, biotin, or any other label known to the skilled person. Said label may be conjugated to the proteins using techniques such as chemical coupling and chemical cross-linkers. Advantageously, said target region may be detected and, optionally, quantified within a sample, for example via a fluorescent label or other detectable label known to the skilled person. In some cases, the target region may be further isolated or purified using said label. In a first aspect, the target region may be isolated via a pull-down reaction, for example on beads coated with streptavidin when the oligonucleotide is labelled with biotin, according to methods known by the skilled person. In a second aspect, the target region may be attached to a support, such as a bead or a chip, via said label. Preferably, said support is functionalized to facilitate attachment of the labelled target region, said label reacting with the functional groups present on the support (for example, a support may be coated with streptavidin or a COOH group, that reacts with an appropriate label).

According to a particular embodiment, at least one of the single-stranded nucleic acid molecules of any of the above embodiments comprises a sequence complementary to an oligonucleotide bound to a surface. Preferably, said oligonucleotide comprises a modification at its 3' end to prevent extension. Single-stranded nucleic acid molecule hybridization and ligation to the 3' overhang, with or without a tag, advantageously generates a hairpin structure which is particularly adapted for use in downstream applications, such as those described in WO 2011/147931, WO 2011/147929, WO 2013/093005, and WO 2014/114687. Preferably, any of the embodiments described above generate a hairpin having a "Y" shape.

The present invention further allows the skilled person to enumerate the number of nucleic acid molecules carrying the said sequence. According to a preferred embodiment, the method of the present invention further comprises detecting and quantifying nucleic acid molecules as described in WO 2013/093005.

Isolated target regions of the present invention are particularly suited to downstream analyses by single-molecule analysis methods, such as the methods described in WO 2011/147931 and WO 2011/147929, nucleic acid detection and quantification methods, such as that as described in WO 2013/093005, and methods for detecting protein binding to nucleic acids as described in WO 2014/114687. Thus, further embodiments and applications of the present method can be found in these applications, which are herein incorporated by reference in their entirety.

According to a preferred embodiment of the invention, the method comprises the enrichment of an SNP or genetic mosaicism comprised within an isolated target region. The SNP or genetic mosaicism is preferably comprised in the sequence recognized by a gRNA within a Class 2 Cas protein-gRNA complex. Preferably, the gRNA comprises the nucleotide base corresponding to the minor allele of the SNP, allowing protection of the target region comprising said minor allele. When multiple alleles of the SNP are present at a given locus, multiple gRNA molecules may be provided, corresponding to each allele, preferably to each minor allele. In cases where gRNA molecules corresponding to both the major and minor alleles are provided, the number of isolated target regions comprising each allele may be quantified, for example to determine if a subject is homozygotic or heterozygotic at the SNP locus. Preferably, the base corresponding to the SNP locus is located within the gRNA sequence at any one of bases −1 to −10, preferably −1 to −6, preferably −4, −5, or −6 relative to the PAM site. Indeed, when a mismatch occurs at one or more of these bases, protection of the nucleic acid region from exonuclease digestion is reduced or abolished. This positioning is particularly advantageous as the presence or absence of an SNP may be determined with reduced possibility for error. In some cases, the target nucleic acid region is further sequenced to determine the allele at the SNP locus. This may notably be performed when a gRNA comprising a degenerate base at SNP locus is used, or to identify the alleles that may be present at adjacent SNP loci within the target region. Indeed, as is well-known to the person skilled in the art, SNPs that are located close to one another in the genome tend to be inherited together.

The degree by which protection of the target region is reduced or abolished will vary according to experimental conditions, the Class 2 Cas protein used, and/or the gRNA used. For example, it is known that Cpf1 has greater binding specificity than Cas9 (Strohkendl et al., *Molecular Cell,* 2018, 71:1-9). Thus, protection of a region comprising a mismatch will be greater when Cas9 is used than when Cpf1 is used. A Cpf1 protein or variant thereof having optimized binding specificity, or a mutated Cas9 protein having increased binding specificity such as those described herein, may be used according to whether or not isolation of regions comprising a mismatch is desired.

According to a preferred embodiment of the invention, the method may further comprise sequencing the isolated target region. Many sequencing methods are available in the art. The method of the invention is particularly well suited for generating hairpins for use in single-molecule sequencing methods, such as those described in described in WO 2011/147931 or WO 2011/147929. The isolated nucleic acid may further be used as a template for specific or non-specific polymerase chain reaction, isothermal amplification, such as loop-mediated isothermal amplification, strand displacement amplification, helicase-dependent amplification, nicking enzyme amplification reaction, reverse transcription, enzymatic digestion, nucleotide incorporation, oligonucleotide ligation, and/or strand invasion. Isolated nucleic acid may also be used as a substrate for sequencing, such as Sanger dideoxy sequencing or chain termination, whole genome sequencing, hybridization-based sequencing, pyrosequencing, capillary electrophoresis, cycle sequencing, single-base extension, solid-phase sequencing, high-throughput sequencing, massively parallel signature sequencing, nanopore-based sequencing, transmission electron microscopy sequencing, optical sequencing, mass spectrometry, 454 sequencing, sequencing by reversible terminators, “paired end” or “mate pair” sequencing, exonuclease sequencing, ligation sequencing (e.g. SOLiD technology), short-read sequencing, single molecule sequencing, chemical degradation sequencing, sequencing by synthesis, massive parallel sequencing, real-time sequencing, semiconductor ion sequencing (e.g. Ion Torrent), multiplex sequencing of paired-end ditags (MS-PET), sequencing by droplet microfluidics, partial sequencing, fragment mapping, as well as combinations of any of these methods.

According to a preferred embodiment, the method of the invention further comprises sequencing target regions by means of single-molecule sequencing, next generation sequencing, partial sequencing, or fragment mapping, more preferably by means of single-molecule sequencing as described in WO 2011/147931 or WO 2011/147929. According to a preferred embodiment of the invention, the method may further comprise detecting the binding of a protein to a specific nucleic acid sequence. A variety of methods for detecting protein binding are available to the skilled person. The method of the invention is particularly well-suited for generating hairpins for use in protein binding methods using single-molecules, such as that described in WO 2014/114687. The isolated target region may further be used as a substrate for detecting protein binding to nucleic acid, for example, as a substrate for detecting epigenetic modifications. Isolated target regions may be used, for example, in bisulfite conversion, high resolution melt analysis, immunoprecipitation (e.g. ChIP, enChIP), microarray hybridization, and other analyses of nucleic acid/protein interactions well-known to the skilled person. The term “epigenetic modifications,” as used herein refers to modifications of the bases constituting a nucleic acid molecule which take place after the synthesis of said nucleic acid molecule. As a non-limiting example, a base modification may result from damage to said base. Epigenetic modifications include, for example, inter alia, 3-methylcytosine (3mC), 4-methylcytosine (4mC), 5-methylcytosine (5mC), 5-hydroxymethylcytosine (5hmC), 5-formylcytosine (5fC) and 5-carboxylcytosine (5caC), as well as 6-methyladenosine (m6A) in DNA, 5-hydroxymethyluracil (5hmU) and pseudo-uridine in RNA, and 3-methyl cytosine (3mC) and N6-methyladenosine (m6A) in DNA and RNA.

Likewise, the method may further comprise the detection of modified bases resulting from nucleic acid damage, such as DNA damage. DNA damage occurs constantly because of chemicals (i.e. intercalating agents), radiation and other mutagens may be performed on the isolated nucleic acid. DNA base modifications resulting from these types of DNA damage are wide-spread and play important roles in affecting physiological states and disease phenotypes. Examples include 8-oxoguanine, 8-oxoadenine (oxidative damage; aging, Alzheimer’s, Parkinson’s), 1-methyladenine, 6-O-methylguanine (alkylation; gliomas and colorectal carcinomas), benzo[a]pyrene diol epoxide (BPDE), pyrimidine dimers (adduct formation; smoking, industrial chemical exposure, UV light exposure; lung and skin cancer), and 5-hydroxycytosine, 5-hydroxyuracil, 5-hydroxymethyluracil, and thymine glycol (ionizing radiation damage; chronic inflammatory diseases, prostate, breast and colorectal cancer).

Preferably, the method of the invention further comprises detecting the binding of a protein to a specific nucleic acid sequence as described in WO 2014/114687.

A further object of the present invention is a kit that can be used for nucleic acid isolation and enrichment according to any of the methods or embodiments of the invention described herein. The kit will provide the materials for preparing a nucleic acid comprising a target region and, optionally, the materials for isolation of said target region according to the methods described herein. Contents may vary according to the Class 2 Type V Cas protein to be used (e.g. Cpf1, C2c1), the protector molecule that is used (e.g. a hairpin or a site-specific endonuclease), the nucleic acid region(s) targeted, etc, according to any of the modalities described herein.

According to a particular embodiment, the kit of the present invention comprises:

a) a Class 2 Type V Cas protein, preferably catalytically active Cpf1,
b) a Class 2 Cas protein, preferably Cas9d,
c) at least two gRNAs, more preferably at least three, four, five, six, 10 gRNAs, each of said gRNAs being complementary to a specific nucleic acid sequence,
d) at least one enzyme having exonuclease activity,
e) optionally, a processive polymerase,
f) optionally, at least one protease, and
g) optionally, a notice of use.

According to a further embodiment, said kit comprises EDTA, preferably a solution of EDTA, in place of or in addition to the at least one protease.

According to a particular embodiment, said kit comprises four gRNAs per target region, wherein two of said gRNAs are complementary to sequences flanking said target region and two of said gRNAs are complementary to sequences located at the extremities of the target region. Thus, sequences located at the extremities of the target region are nested between sequences flanking said target region. In cases where downstream multiplex analyses are desired, the kit may comprise two or more Class 2 Cas proteins and two or more gRNAs, thereby targeting at least two different target regions. In some cases, at least one of said Class 2 Cas proteins comprised in the kit is pre-loaded with gRNA, forming a Class 2 Cas protein-gRNA complex. According to a particular embodiment, when the kit comprises multiple Class 2 Cas protein-gRNA complexes for use in preparing a nucleic acid molecule comprising a target region (e.g. multiple Class 2 Type V Cas protein-gRNA complexes), said complexes are preferably mixed together in a single container. Similarly, when the kit comprises multiple Class 2 Cas protein-gRNA complexes for use in isolating a target region, said complexes are preferably mixed together in a single container. However, Class 2 Cas protein-gRNA complexes for use in preparing a nucleic acid molecule comprising a target region are not mixed with Class 2 Cas protein-gRNA complexes for downstream use in isolating a target region. Preferably, the ratio of each Class 2 Cas protein-gRNA complex comprised in said kit has been predetermined for ease of use.

Preferably, the guide segment of the gRNA is complementary to the target region itself or to a sequence within the target region that is of interest in clinical diagnostics or genetic risk assessment. As an example, said gRNA is complementary to a non-coding target region located downstream of the coding region of septin 9 (SEPT9) or epidermal growth factor receptor (EGFR). Indeed, the epigenetic status of these regions is known to be important for cancer outcome. As another example, said gRNA is complementary to a target region located downstream of the sequence coding for fragile X mental retardation 1 (FMR1), which is involved in Fragile X syndrome. A mutation in the number of copies of a 5'-CGG-3' repeat in this gene is responsible for disease. The epigenetic status of the region upstream of this CpG island (e.g. methylation) is also known to be related to the clinical severity of the disease. As another example, said gRNA is complementary to a target region in the coding region of DM1 protein kinase (DMPK). Indeed, an expansion in the number of 5' CTG-3' repeats is characteristic of myotonic dystrophy type 1. As a further example, said gRNA is complementary to a target region comprising one or more cfDNA molecules. Indeed, isolation of specific cfDNA, such as cffDNA or ctDNA, is of particular interest in a wide variety of downstream applications including prenatal testing (see, for example, Gahan, *Int J Womens Health.* 2013, 5: 177-186) and cancer diagnosis and/or monitoring (see, for example, Ghorbian and Ardekani, *Avicenna J Med Biotech.* 2012, 4(1): 3-13). One or more cfDNAs or target regions comprised within a cfDNA may advantageously be isolated directly from a biological sample (e.g. a plasma, serum, or urine sample).

The kit described herein preferably enables isolation of at least two different target regions. Indeed, the value of certain epigenetic cancer diagnostic tests has been shown to be improved by multiplexing, wherein the characteristics of the sequence or structure of two or more different target regions (e.g. methylation status) are analysed in a single test. As a non-limiting example, the kit provided herein enables isolation of target regions comprising or consisting of the human GSTP1, APC and/or RASSF1 genes or appropriate regions thereof that are subject to DNA methylation according to any of the methods described herein. Said isolated target regions may then be subjected to downstream analysis of methylation status, for example according to the methods provided herein (e.g. as provided in WO 2014/114687). Such a kit is particularly advantageous in the determination of risk of a subject developing prostate cancer (Wojno et al., *American health & drug benefits,* 2014, 7(3): 129), and is advantageous over existing kits which notably use bisulfite treatment of sample DNA followed by PCR. In contrast to the methods of the invention, nucleic acids isolated with existing kits may notably be prone to false positive and false negative signals, as well as sample loss due to the harsh and inefficient chemical treatment. According to a particular embodiment, the kit preferably comprises at least two gRNAs per target region, said gRNAs being complementary to sites flanking human gene(s) GSTP1, APC and RASSF1 as defined herein.

As another non-limiting example, the kit of the present invention enables preparation and isolation of at least one of the following target regions located within the human genome at the following positions: 65676359-65676418 on chromosome 17, 21958446-21958585 on chromosome 9, 336844-336903 on chromosome 6, 33319507-33319636 on chromosome 21, 166502151-166502220 on chromosome 6, 896902-897031 on chromosome 18, 32747873-32748022 on chromosome 5, 27949195-27949264 on chromosome 6, 27191603-27191672 on chromosome 7, 170170302-170170361 on chromosome 16 30797737-30797876 on chromosome 15, 7936767-7936866 on chromosome 1, 170077565-170077634 on chromosome 1, 1727592-1727661 on chromosome 2, 72919092-72919231 on chromosome 8, preferably of all 15 target regions. Isolation of said target regions is advantageous as downstream analyses of DNA methylation status of said target regions may be used to detect bladder cancer. Existing kits use methylation sensitive restriction enzymes followed by PCR to identify methylated sequences, and may therefore be limited by the presence of the appropriate restriction sites in the target regions, complicating test design, and limiting sensitivity. Thus, an improved kit for the isolation and detection of bladder cancer may preferably comprise two gRNAs that are at least partially complementary to sequences flanking the target region and two additional gRNAs that are at least partially complementary to sequences located at the extremities of said target region for isolation of each of these 15 target regions according to the methods described herein, preferably for isolation of all 15 target regions.

As a non-limiting example, the target region may comprise a specific sequence, a specific number of sequence repeats, one or more nucleotide base modifications, or not. As a further non-limiting example, the region targeted for isolation may be a specific length or a length that differs from said specific length. Preferably, the kit of the invention further comprises at least one restriction enzyme, and/or an RNase. Preferably, the kit further comprises a suitable Class 2 Type V Cas protein reaction buffer and a suitable Class 2 Type II Cas protein reaction buffer, such as those detailed in the examples below.

The kit may further comprise additional elements, as is appropriate for a given application. For example, the kit may further comprise one or more protector molecules, preferably a hairpin adaptor or site-specific endonuclease, ligase and/or polymerase enzymes, oligonucleotides, dNTPs, appropriate buffers, and the like.

Additional features and advantageous aspects of the present invention are illustrated in the figures and examples below.

FIGURE LEGENDS

FIG. 1. Schema illustrating a method of the invention using two Type 2 Class V Cas protein-gRNA complexes, followed sequentially by the use of two nested Type 2 Class II Cas protein-gRNA complexes. (A) DNA comprising a target region (fragmented or not) is first contacted by two Cpf1-gRNA complexes that bind to first and second sequences flanking the target region to be isolated. The Cpf1 guide was designed such that the Cpf1 PAM sequence is located within the nucleic acid molecule comprising the target region, as illustrated by the arrow pointing inwards). (B) Without being limited by theory, the strand that does not comprise the PAM sequence may dissociate from the complex after cleavage has occurred. (C) The reaction tube is supplemented with a cocktail of exonucleases (in this particular case, λ exonuclease (λ exo) as well as exonuclease I (exoI)), which will degrade the non-protected nucleic acid molecules. Degradation can be partial or complete. Endonucleases (for example, restriction enzymes) can advantageously be added at this step to generate more ends for exonuclease degradation. (D) The resulting fragments contain 5' overhangs generated by both Cpf1 and exoI treatment that should be repaired (the ends are preferably blunted) in order to promote downstream λ exo degradation of the 5' strand. This is accomplished using either a mesophilic DNA polymerase (more preferably T4 DNA polymerase) or a thermophilic polymerase. (E) The fragment (or population of fragments) is contacted by 2 Cas9d-gRNA complexes per target region, which bind to third and fourth sequences located at each end of the target region, preferably located at least 100 bases from the initial sequences targeted by the Cpf1-gRNA complexes. (F) After the complexes are loaded onto the fragments, the reaction may be supplemented with either λ exo to obtain fragments containing 3' overhangs (left molecule in F) or exonuclease Ill to generate 5' overhangs at both ends of the target region (right molecule in F).

FIG. 2. Specific example of the method of the invention using two Type 2 Class V Cas protein-gRNA complexes followed by the use of two nested Type 2 Class II Cas protein-gRNA complexes with or without the end repair step. (A) To demonstrate the effectiveness of the end repair step in generating the appropriate fragments with a 3' overhang, we generated a PCR fragment comprising the target region Sept9.2 (step (i), (ii); expected fragment size: 1972 bp). We incubated the PCR fragment with Cpf1-crRNA complexes binding to sequences flanking the target region and treated the reaction with λ exo as well as exoI (step (iii); expected fragment size: 1050 bp). The reaction was then split into two tubes and they were either treated with End Repair (step (iv); expected fragment size: 1100 bp) or not (step (vii)). The corresponding Cas9d-gRNA for this target was then added to both tubes (step (v) or (viii)) and added λ exo as well as exoI (step (vi) or (ix)). If the fragments are an appropriate substrate for λ exo, the size of the resulting fragment will correspond to the fragment protected by the two Cas9d-gRNA complexes, including the third and fourth sequences to which dCas9 was bound (step (vi)). If this is not the case, the λ exo will ineffectively initiate digestion from the long 5' overhang and will lead to the production of a plurality of fragments of different sizes (step (ix)). (B) Results of the experiment described in (A). Lane 1 corresponds to the PCR product Sept9.2. Lane 2 corresponds to the fragment after Cpf1 and exonuclease treatment (fragment of step (iii)). Lane 3 represents the fragment after end repair (step (iv)). Because the ends are repaired, the fragment migrates slightly slower than the fragment of step (iii) and the size of the fragment of interest is increased by 42 bp. Lane 4 corresponds to partial fragments of step (ix) generated after exonuclease treatment when there is no end repair. Lane 5 corresponds to the desired fragment of step (vi) where end repair has been performed followed by isolation using two Cas9d-gRNA complexes and exonuclease treatment (steps of isolation are all together referred to as "dCas9"; expected fragment size: 750 bp). Sizes are determined by comparison with the molecular weight marker to the left of lanes 1-5. End repair allows for the full conversion of the prepared nucleic acids comprising the target region into the isolated target region, as no other fragment is present.

FIG. 3. Comparison of the efficacy of end repair in generating the expected fragments using *E. coli* genomic DNA as the starting material. (A) Results obtained without the end repair step. 3 targets were selected from *E. coli* genomic DNA of different sizes (target #1, #2 and oriC). The corresponding Cpf1-gRNA for these targets were first incubated with the genomic DNA, followed by treatment with λ exo as well as exoI. After this treatment, the reaction was loaded on the Fragment Analyzer® (AATI©) with the High Sensitivity NGS Fragment Analysis Kit (1 bp-6,000 bp) (left panel). The expected peaks, corresponding to the sizes of the 3 nucleic acid molecules comprising a target region protected by the two Cpf1-crRNA complexes, were all observed (fragment sizes of 5357, 1502, and 774 bp respectively). The reaction was then incubated with two Cas9d-gRNA complexes corresponding to these three targets and the reaction was supplemented with λ exo as well as exoI. λ exo could not initiate the exonuclease reaction efficiently and therefore, the fragments are either not digested or are only partially digested. Multiple peaks corresponding to fragments of different sizes are therefore visible (right panel). (B) The same fragments, after Cpf1 treatment, were subject to End Repair (NEB) prior to incubation with Cas9d-gRNA complexes (left panel; fragment sizes of 5436, 1569, and 812 bp, respectively). Following binding with Cas9d, λ exo and exoI were added to the reaction and the resulting fragments analysed on a Fragment Analyzer® (AATI©) with the High Sensitivity NGS Fragment Analysis Kit (1 bp-6,000 bp) (right panel). A single peak per target, corresponding to the fragment protected by the two Cas9d-gRNA complexes, was observed when end repair was performed (fragment sizes of 5103, 1359, and 474 bp, respectively). RFU: relative fluorescent units; UM: 6000 bp upper marker.

Figure 4:
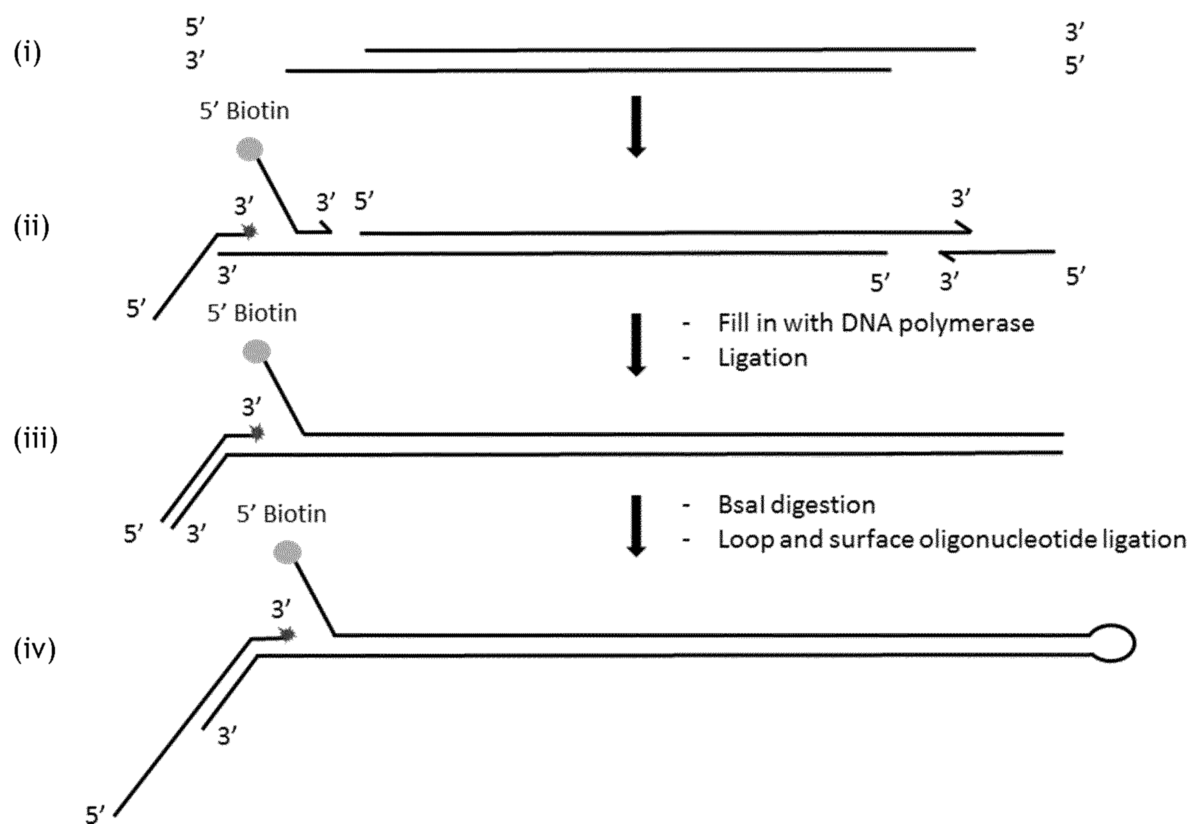

FIG. 4. Schema representing the method of generating a hairpin from the isolated target region obtained in the method presented in FIG. 1. The fragment containing a 3' overhang of (i) is hybridized with 3 different oligonucleotides per target as illustrated in (ii). 1. An oligonucleotide containing a binding moiety (e.g. biotin), which hybridizes at least 50 bases from the Cas9 PAM sequence, 2. A surface oligonucleotide containing a phosphate at its 3' end to prevent polymerization and that corresponds to the Cpf1 target sequence. Both of these oligonucleotides hybridize to the same 3' overhang. 3. A third oligonucleotide that hybridizes to the opposite 3' overhang to create the restriction site for ligating the loop ((ii)). After fill in using a DNA polymerase (preferably the Bst full length DNA polymerase), the fragment corresponds to that shown in (iii).

This fragment is digested with the non-palindromic restriction enzyme BsaI (this site is generated by both the surface and loop oligonucleotides) to allow directional ligation of the surface oligonucleotide as well as the loop (final product illustrated in (iv)).

Figure 5A:
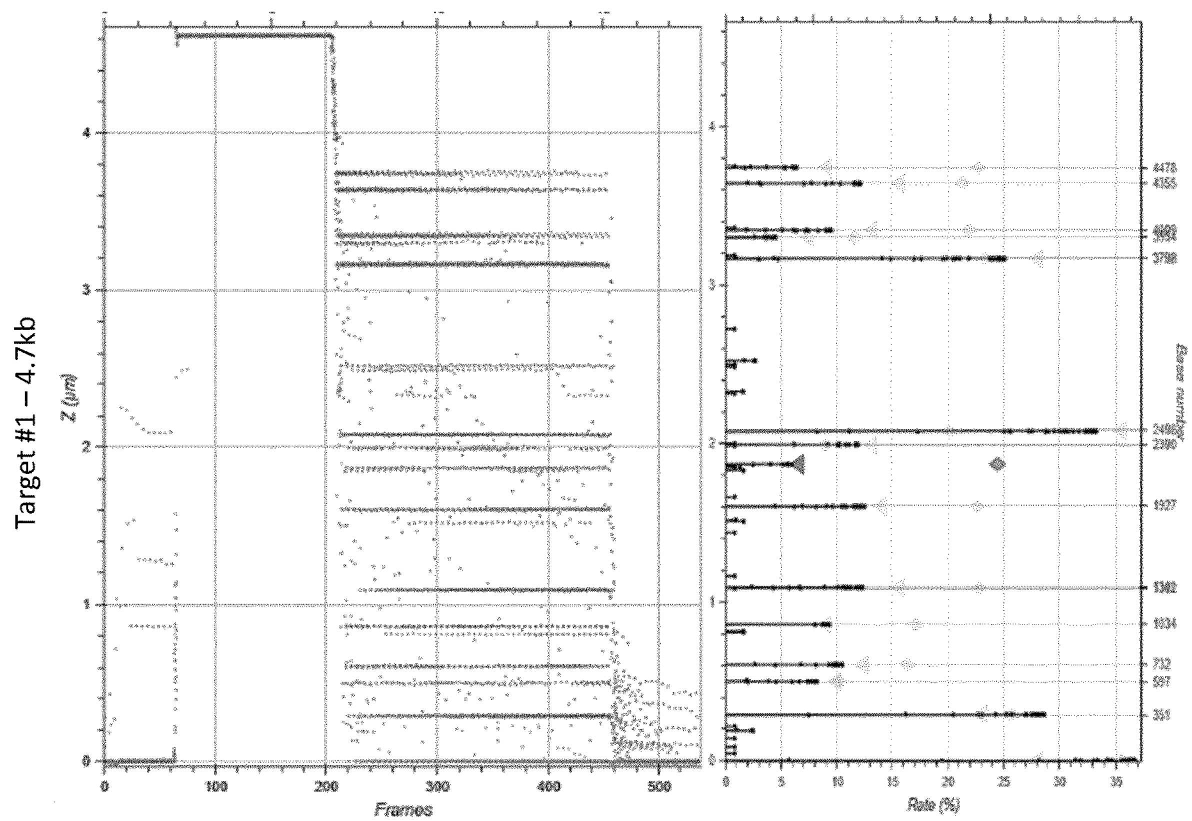
Figure 5B:
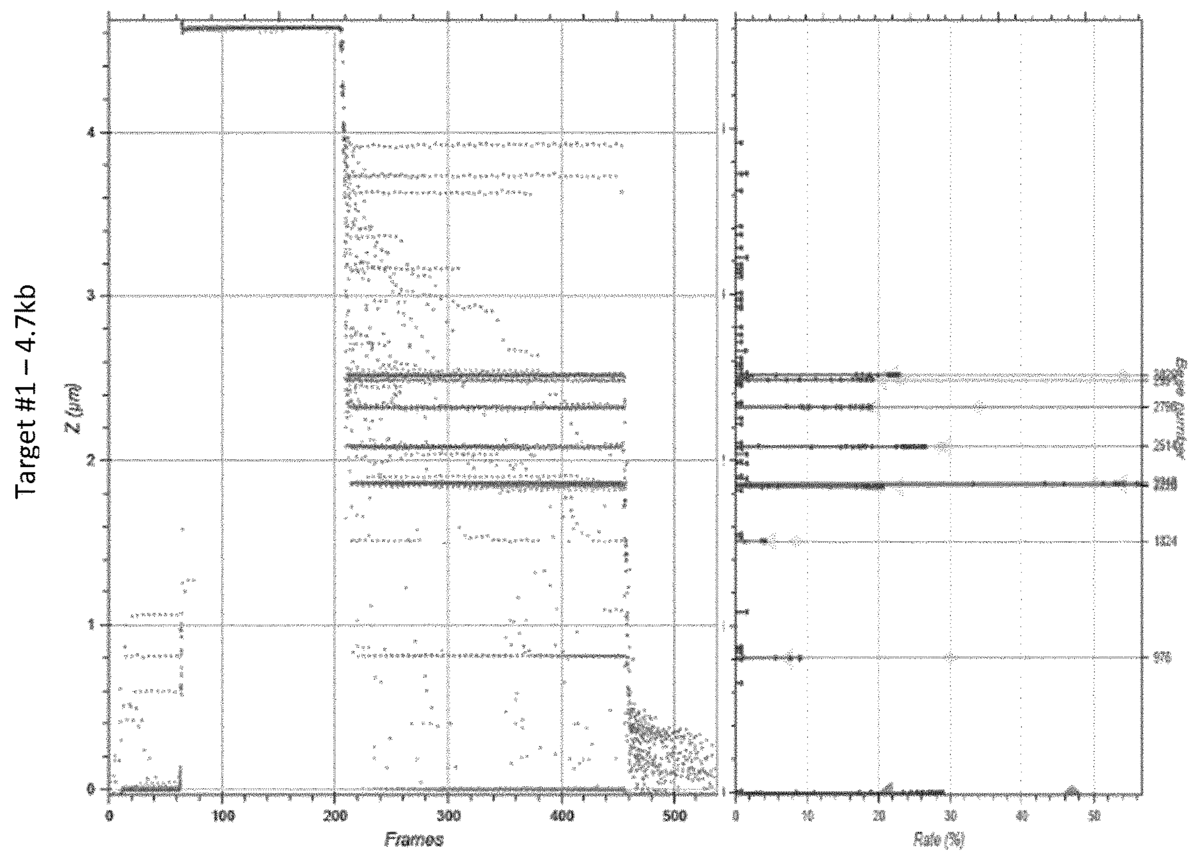

FIG. 5. Analysis of the "Target #1" fragment generated from *E. coli* genomic DNA. (A) Typical identification traces using the oligonucleotide CAAG that corresponds to target #1 (left panel). The histogram corresponding to the experimental blockages was generated. (right panel). Based on this histogram, blockages corresponding to this oligonucleotide were successfully identified as summarized in the table below the graphs. Expected base numbers are indicated on the right axis of the histography as well as in the table ("expected"). (B) The antibody ICC/IF clone (Diagenode) specific for the epigenetic modification $m^5C$ was also tested on the same molecules as described in (A), with identification traces shown in the left panel and the histogram shown in the right panel. This modification is present on the motif CCWGG in *E. coli*. All corresponding modifications on this fragment were successfully identified, as shown in the table below the graphs. [1]Peaks too close to be separated. [2]Extra peak.

Figure 6A:
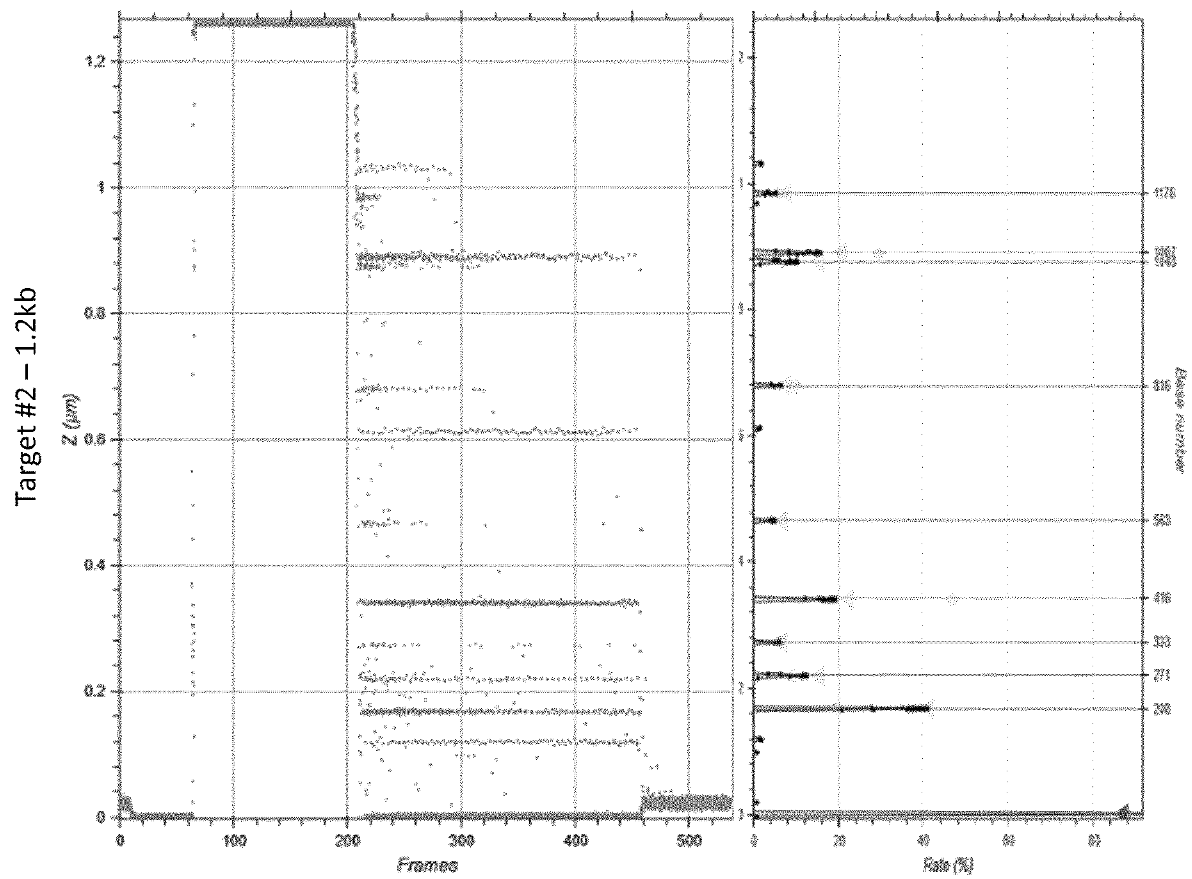
Figure 6B:
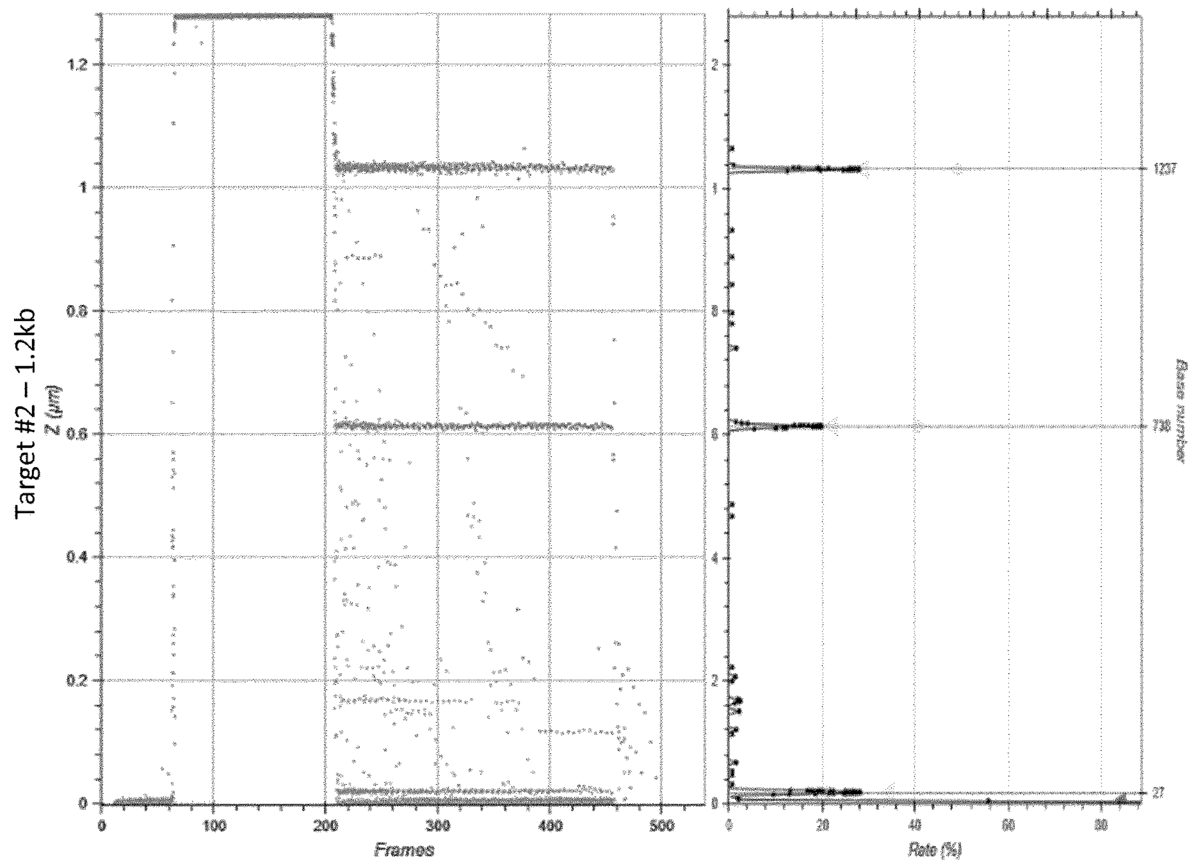

FIG. 6. Analysis of the "Target #2" fragment generated from *E. coli* genomic DNA. Histograms/tables are as described previously for FIG. 5.

Figure 7A:
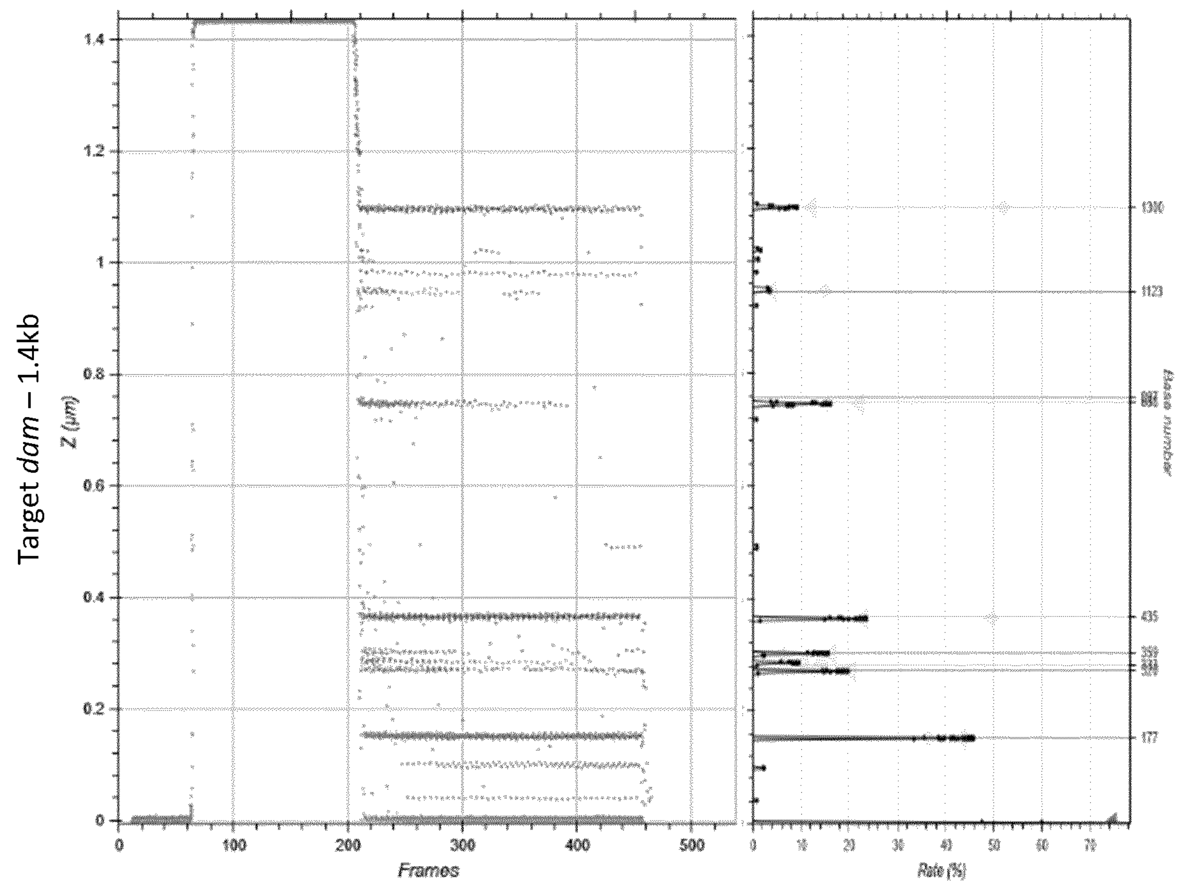
Figure 7B:
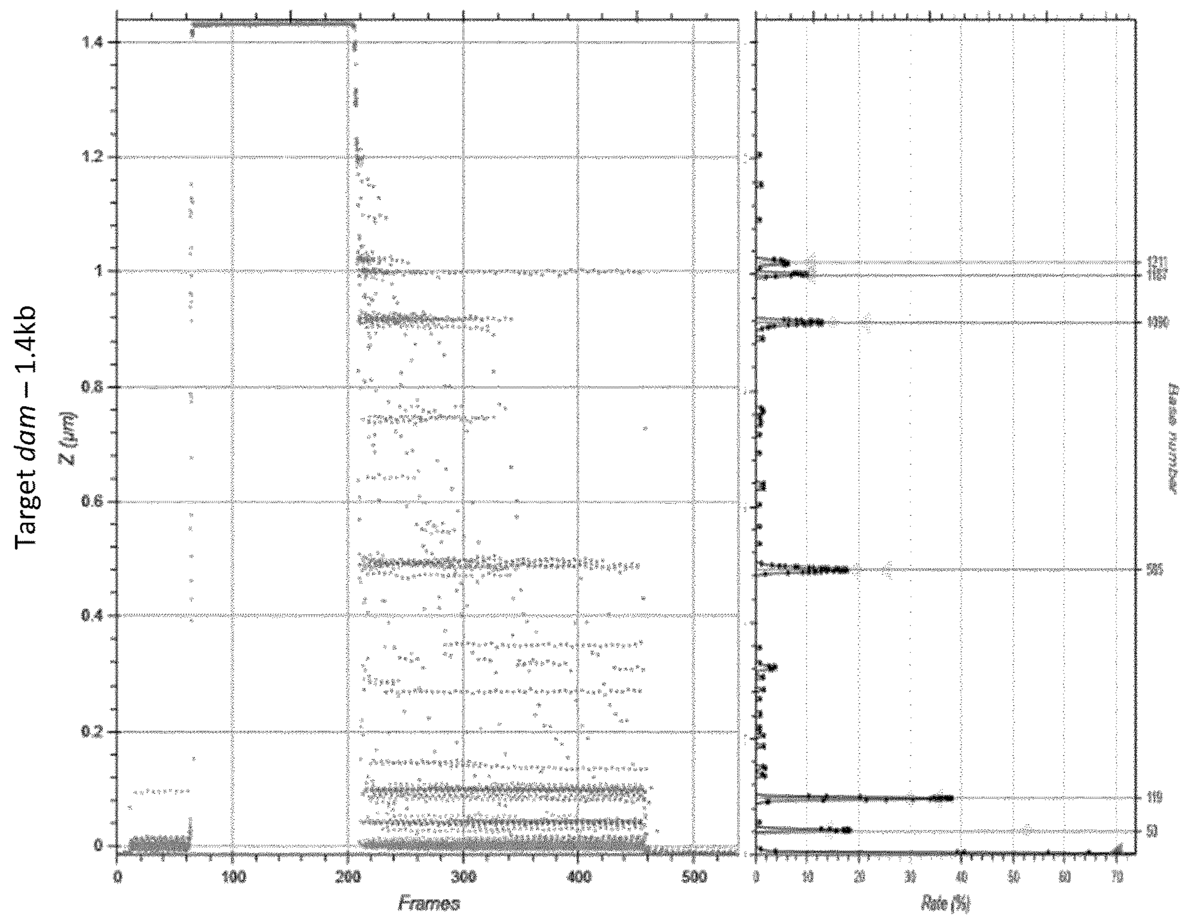

FIG. 7. Analysis of the "DAM" fragment generated from *E. coli* genomic DNA. Histograms/tables are as described previously for FIG. 5.

Figure 8A:
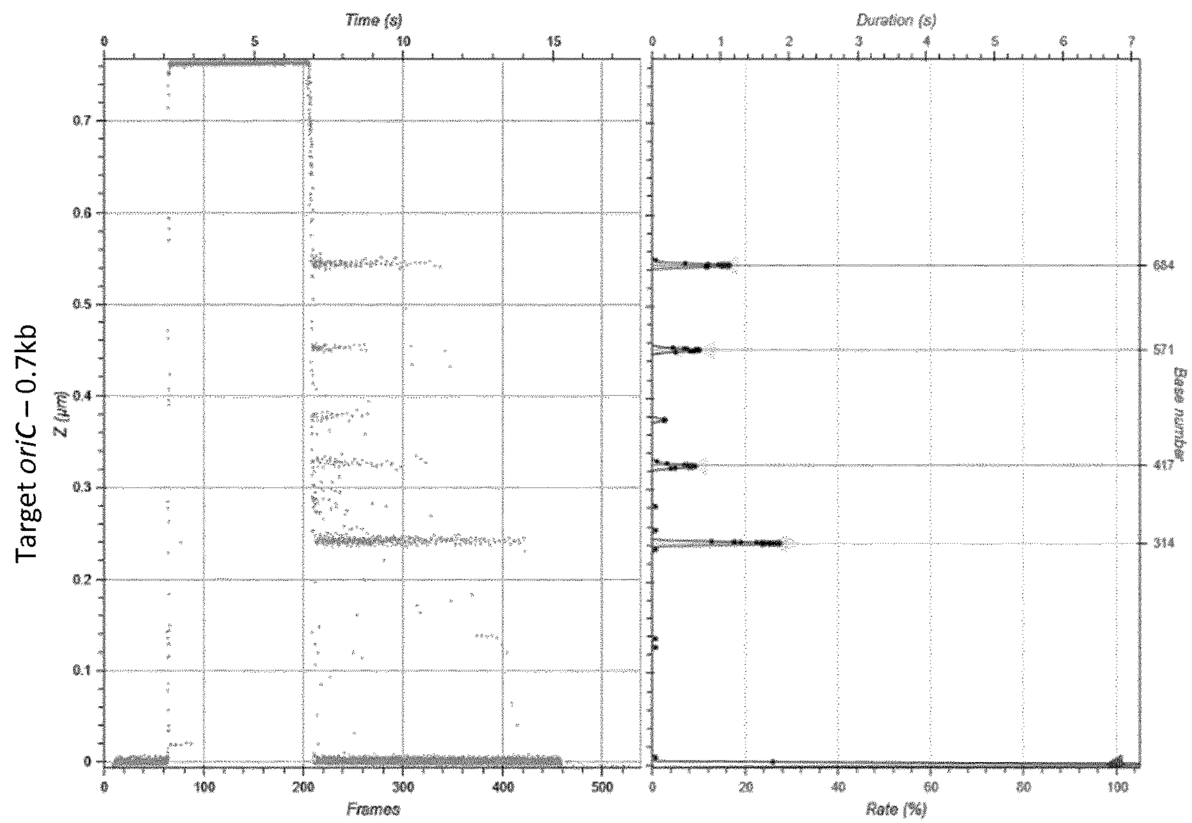
Figure 8B:
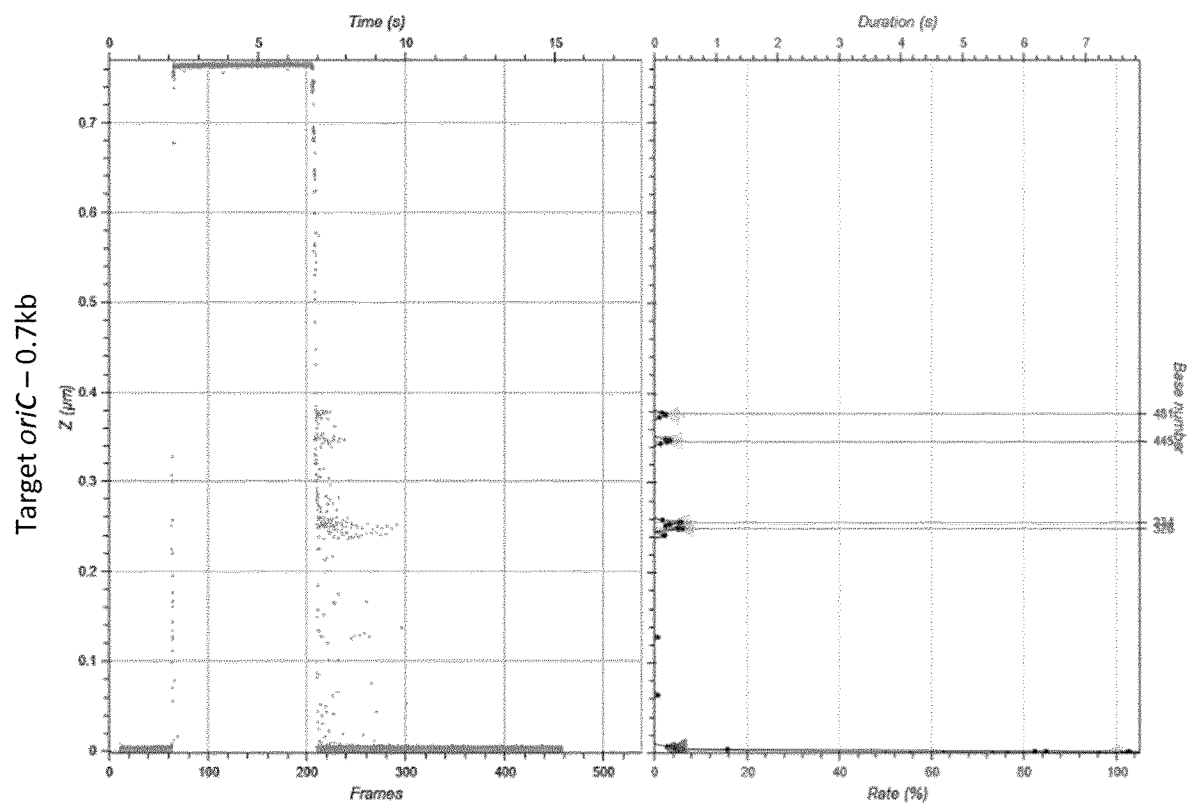

FIG. 8. Analysis of the "oriC" fragment generated from *E. coli* genomic DNA. Histograms/tables are as described previously for FIG. 5.

FIG. 9. Estimation of improvement in the efficiency of targeting four *E. coli* regions and their analysis on the SIMDEQ™ platform. The table represents an estimation the number of analysable molecules after multiple replicates of hairpin production for the four *E. coli* targets (Target #1, #2, dam and oriC) with or without end repair. Each experiment has been independently performed starting from *E. coli* genomic DNA with the protocol illustrated in FIG. 1 and hairpins have been produced as illustrated in FIG. 4. Two replicates have been performed without the end repair step and three with this additional step. Multiple fields-of-view (FOV) were examined in each replicate to estimate the number of functional hairpin molecules (HP) present in a given number of FOV. The mean number of functional HP per FOV was then determined and an estimation of the total number of hairpins present per flow cell was obtained by multiplying this number by the total number of possible FOV per flow cell (roughly 8000 FOV per flow cell). As only $1/5^{th}$ of the total number of beads are loaded in the flow cell, this allowed us to estimate that the total number of hairpins attached on beads (i.e. if all beads were loaded in the flow cell, we would have 5 times more HP). Since HPs were resuspended in 20 μl and a dilution of this preparation was made to attach the HPs on the beads, the total number of HPs can be multiplied by the dilution factor to estimate the quantity of analysable molecules present in the reaction (column 'Total HP'). The efficacy of the protocol to produce hairpins from a given quantity of starting material (in this case, *E. coli* gDNA) was calculated by dividing the estimated total number of experimental hairpins by the theoretical expected number of hairpin molecules, considering a starting material of 1 μg of *E. coli* genomic DNA (which represents potentially $2\times10^8$ copies of the genome).

FIG. 10. Preparation of a sequencing library from human genomic DNA containing 15 different targets. Target regions selected for enrichment with corresponding genomic coordinates. These regions were selected either due to the presence of epigenetic biomarkers or known loci with expanded repeats involved in human diseases.

Figure 11:
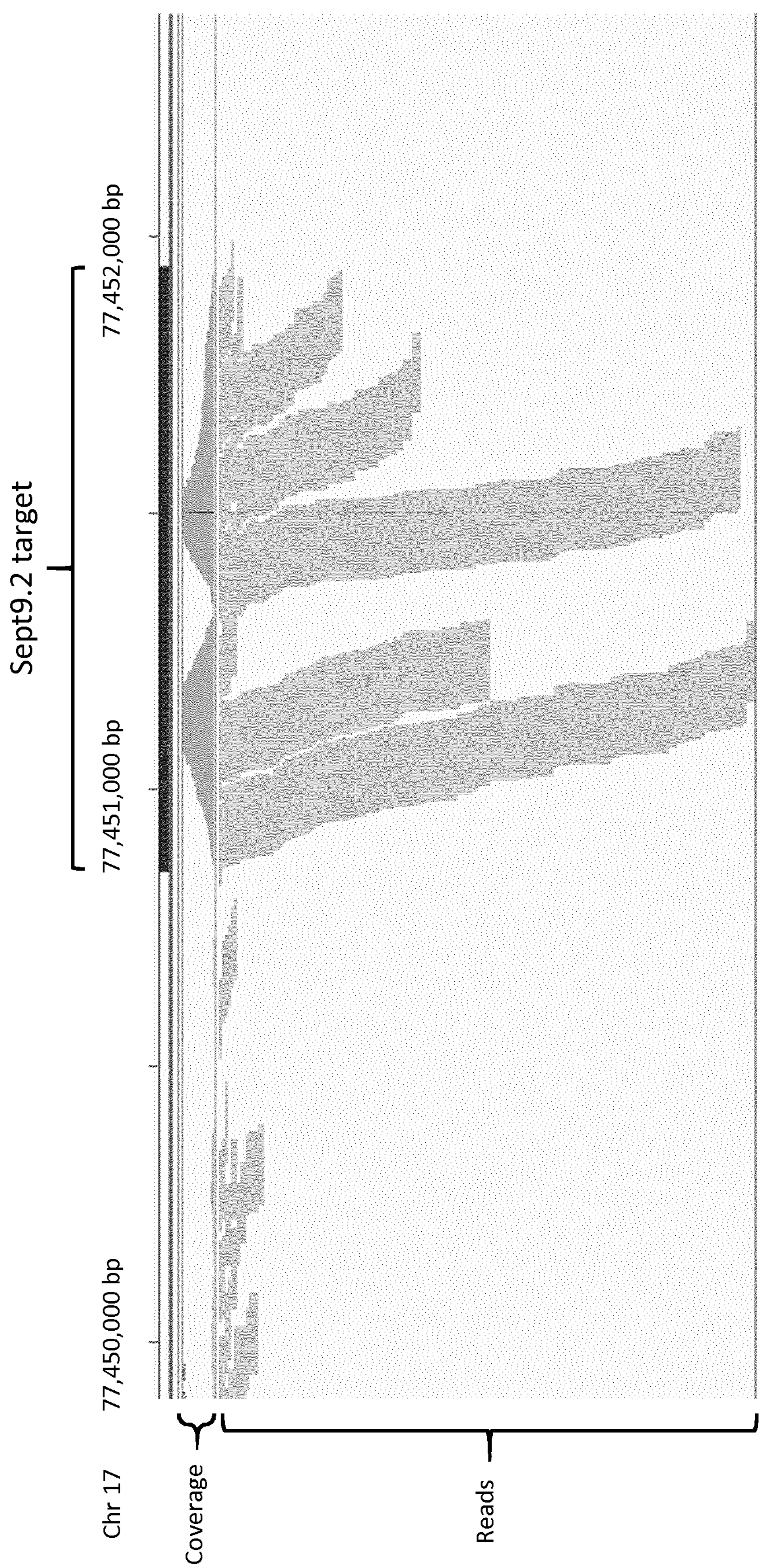

FIG. 11. Exemplary results from Illumina sequencing performed on the library prepared from human genomic DNA containing the 15 different targets as listed in FIG. 10. Screenshot representing the Sept9.2 enriched region (depicted by the black rectangle). Reads that aligned to this region are shown in light grey. This region shows high coverage (illustrated in dark grey) whereas the surrounding regions, as expected, show few if any reads, indicative of good enrichment.

Figure 12:
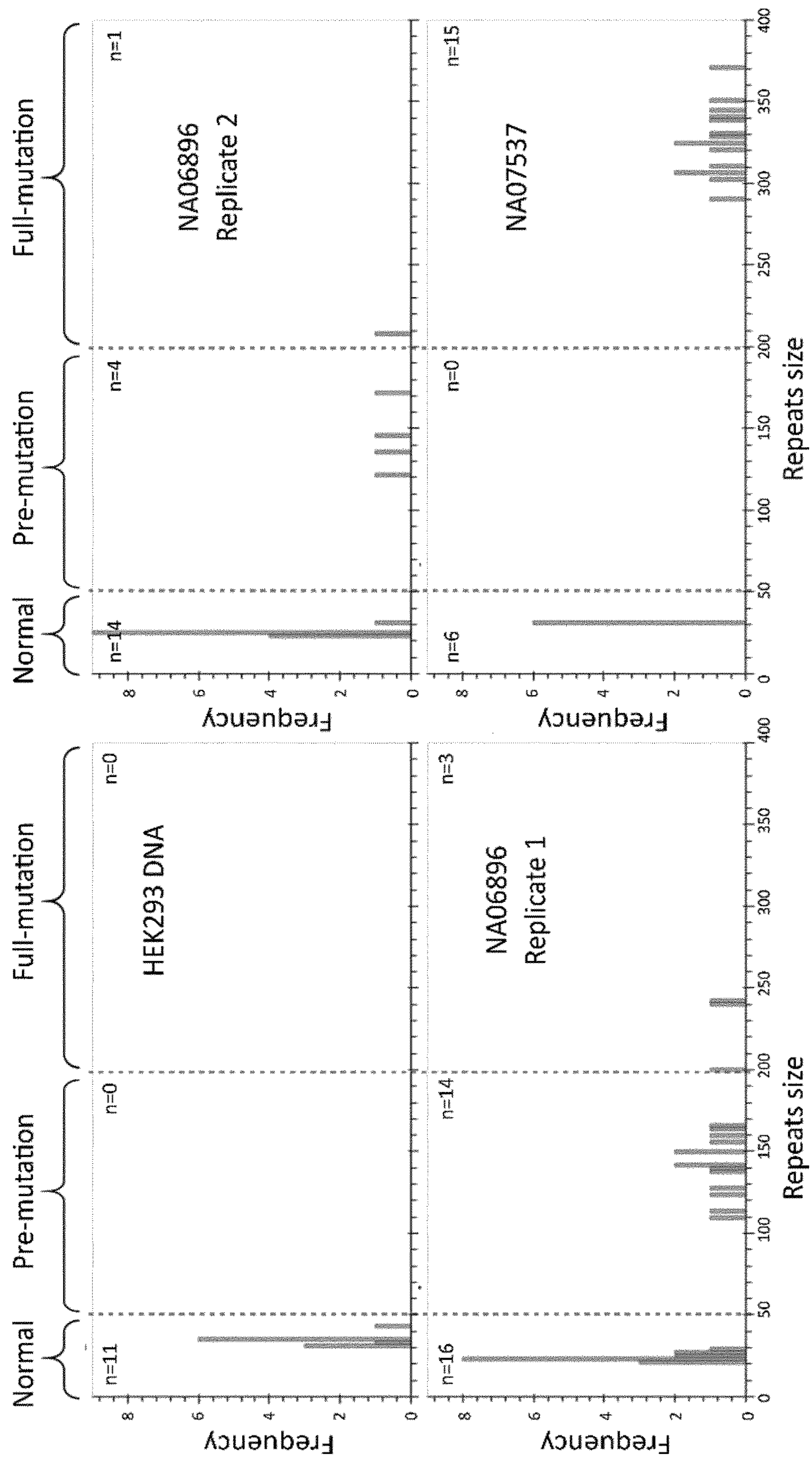

FIG. 12. Analysis of repeat length of the FMR1 locus. The STR (short-tandem repeat) size is analysed using 10 specific 8-base oligonucleotides which specifically bind to the sequences located downstream and upstream of the CGG-repeat position. The estimated number of repeats is then determined by finding the best fit between the theoretical binding and the experimental blocking positions. Histograms of the distribution of CGG repeat lengths ("repeat size") for FMR1 for four DNA samples (HEK293 cell DNA, and two clinical samples, NA06896 and NA07537). n represents the number of molecules identified in each of the following three categories: normal (<50 repeats), pre-mutation (between 50 to 200 repeats) et full-mutation (>200 repeats).

FIG. 13: Summary of the various libraries prepared and results obtained from these samples. [1]Amount of DNA used to prepare the library, [2]Amount of the starting material injected in the flow cell, [3]Proportion of the flow cell analysed, [4]Relative quantity of starting material analysed (calculated by multiplying columns 1×2×3), [5]Number of molecules analysed on SIMDEQ and their repartition according to fingerprint, [6]Quantification of the number of FMR1 repeats, N/A: Not included in the library preparation.

Figure 14:
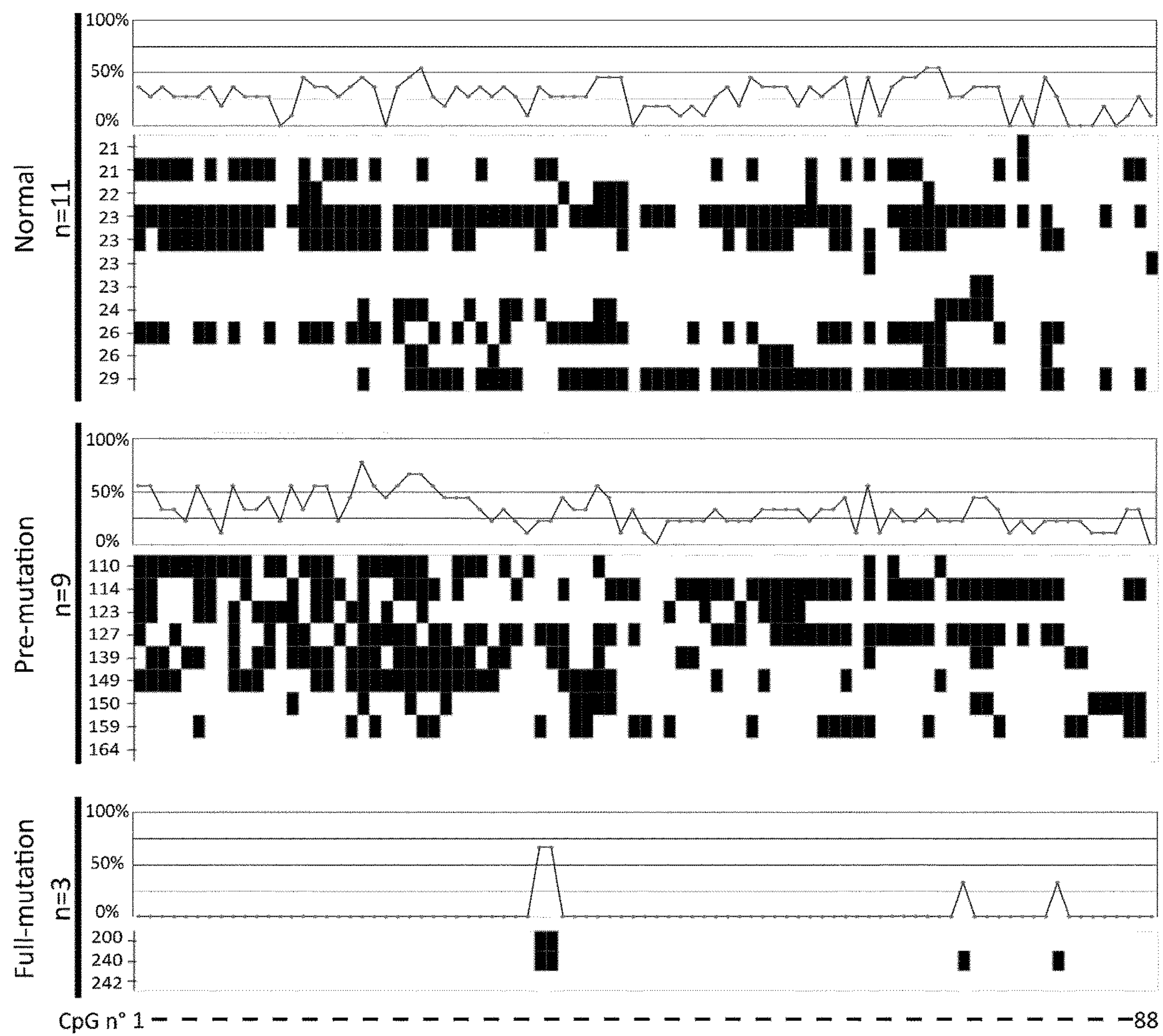

FIG. 14. Analysis of methylation status of the FMR1 promotor. For one DNA sample (NA06896-Replicate 1), the methylation status of the CpG island region located within the promotor region of FMR1 was analyzed. The same molecules were characterized for both the size of CGG repeats and the methylation status across all of the predicted CpG and non-CpG sites. For base modification detection, the anti-$m^5C$ antibody clone ICC/IF (Diagenode) was injected at a 1/500 dilution in ABBE buffer (20 mM Tris HCl, 150 mM NaCl, 2 mg/mL BSA, 0.6 mg/mL sodium azide). These molecules were grouped according to their repeat length and the methylation status was plotted according to the CpG position. All CpG or non-CpG sites are represented along the x-axis (the list and position of these sites is detailed in FIG. 15). Line graphs represent the frequency of molecule identified as methylated for a specific CpG or non-CpG site within this population.

FIG. 15. CpG and Non-CpG sites on the FMR1 locus. List of all of the positions and the rate of methylation across the molecule of the NA06896 DNA sample.

EXAMPLES

The following examples are included to demonstrate preferred embodiments of the invention. All subject-matter set forth or shown in the following examples and accompanying drawings is to be interpreted as illustrative and not in a limiting sense. The following examples include any alternatives, equivalents, and modifications that may be determined by a person skilled in the art.

Example 1: Methods of Selecting gRNAs

For all strategies described below, one or more guide RNAs are designed using available online tools. RNA guides can then either be synthesized in vitro using a viral transcriptional system (for example, T7, SP6 or T3 RNA polymerase, etc.) or be chemically produced using an automated synthesizer as a single guide or as a two part guide consisting of a crRNA (which contains the sequence complementary to the target region) and an invariant tracrRNA (that contains a region complementary to the crRNA as well as a sequence introducing a specific structure required for the activity of the enzyme). The efficiency of each gRNA is evaluated in vitro on a standardised/control sample (e.g. PCR fragments) using the wild type Cas nuclease (e.g. Cas9-gRNA, Cpf1-crRNA, etc.). This is to ensure that each Cas protein-gRNA complex will cleave with high efficiency (e.g. at least 80% of the initial PCR fragment is cleaved). Indeed, it has been previously shown that the protection level of the target fragments, even with a catalytically dead version of a Cas enzyme, is directly related to the ability of the wild-type (WT) enzyme (in conjunction with a specific gRNA) to cleave the DNA in vitro. In other words, a WT Cas protein-guide RNA complex that inefficiently cuts at a given sequence will also inefficiently protect said sequence from exonuclease digestion, even when a catalytically dead version of the Cas protein is used.

In the present example, Cpf1 guide RNA(s) are chemically produced using an automated synthesizer according to a common generic sequence (SEQ ID NO: 1). Cas9 guide RNA(s) are synthesized in vitro using a viral transcriptional system as described above according to a generic sequence (SEQ ID NO: 4) or chemically produced using an automated synthesizer. In some cases, a universal tracrRNA (SEQ ID NO: 3) may be annealed to the target specific crRNA (generic sequence shown in SEQ ID NO: 2).

gRNAs are incubated in the corresponding buffer for 5 minutes at 95° C., followed by a progressive ramp at 80° C., 50° C., 37° C. and room temperature for 10 minutes at each step for annealing and/or secondary structure formation.

Example 2: General Reaction Protocols 2.1 Exemplary Method for the Preparation of a Nucleic Acid Molecule Comprising a Target Region for Isolation 1. Guide RNA (notably crRNA when the Class 2 Cas protein belongs to Type V or gRNA when the Class 2 Cas protein belongs to Type II) is loaded onto the Class 2 Cas protein by incubation for 10 minutes at room temperature (e.g. 25° C.) in the appropriate reaction buffer, thereby allowing for formation of the protein-RNA complex.

For Type V Cas proteins, the reaction buffer comprises 50 mM NaCl, 10 mM Tris-HCl, 10 mM $MgCl_2$, 10 mM DTT, 100 μg/ml BSA, pH 7.9, while for Type II Cas proteins, the reaction buffer comprises 20 mM Tris-acetate, 10 mM Magnesium acetate, 50 mM Potassium Acetate, 100 μg/ml BSA, 0.1% TRITON X-100 (also known as t-Octylphenoxy-polyethoxyethanol), pH 7.9.

2. The loaded complexes prepared in step 1 are added to a sample comprising nucleic acid molecules and incubated for 1 hour at 37° C. in order to allow the class 2 Type V Cas protein-gRNA complex to bind and cleave the nucleic acid comprising the target region.
3. A cocktail of exonuclease(s) (e.g. λ exonuclease and exonuclease I) is added and the mixture is incubated for 1 hour at 37° C. Enzymes are then inactivated at 75° C. for 15 minutes.
4. The reaction is stopped by adding "Stop buffer" (comprising a mixture of 1.2 units of Proteinase K and 20 mM EDTA), thereby removing the protein-gRNA complex from the target region. In some cases, RNaseA may be added to digest the gRNA. RNaseA and Proteinase K treatments may notably be performed successively for 15 minutes at 37° C. In this case, addition of EDTA may be optional.
5. The sample is incubated with a DNA polymerase that repairs recessed 3' ends.

2.2 Exemplary Method for Isolating a Target Region

1. A catalytically inactive Class 2 Cas protein is loaded with gRNA by incubation for 10 minutes at room temperature (e.g. 25° C.) in the appropriate Cas protein reaction buffer, as described above.
2. The loaded complexes are then added to the DNA prepared according to protocol 2.1, and incubated for 1 hour at 37° C. in order to allow the Cas protein-gRNA complex to bind to the target region.
3. One or more exonucleases (e.g. λ exonuclease) is added to the reaction and the mixture is incubated for 1 hour at 37° C. Enzymes are then inactivated at 75° C. for 15 minutes.
4. The reaction is stopped by adding Stop buffer (described above), thereby removing the Cas protein-gRNA complex from the target region.

The 3' ssDNA overhang created by the λ exonuclease may then be used as a template for oligonucleotide to produce specific molecules for downstream application (e.g. hairpin or sequencing libraries).

Example 3: Illustration of the General Reaction Protocols on a PCR Fragment

As a specific example of the above-mentioned protocols, a 2 kilobase (kb) PCR fragment was generated from the SEPT9.2 target region (SEQ ID NO: 5) using the GXL PrimeStar Polymerase (Takara) with the oligonucleotides PS1131 and PS1132 (respectively SEQ ID NO: 6 and 7) according to the manufacturer's instructions. This fragment was incubated with two different Cpf1 complexes preloaded respectively with Cpf1-SEPT9.2-crRNA #1 or #2 (respectively SEQ ID NO: 8 and 9) in Type V Cas protein reaction buffer for 1 hour at 37° C. in order to allow the Cpf1 protein-gRNA complexes to bind nucleic acid sequences flanking the target region and cleave. The reaction was then supplemented with λ exonuclease and exonuclease I for 1 hour at 37° C. to digest unprotected DNA. After cleavage with Cpf1, and without being bound by theory, the distal 3' strand DNA from the PAM site may be released from the complex and become a substrate for exonuclease digestion. Reactions were stopped by adding Stop buffer and nucleic acid molecules were purified using KAPA Pure beads (Roche Life technology). These two reactions were then treated (or not) with the End Repair Reaction Mix (NEB) to blunt the dsDNA and/or repair any 5' ssDNA ends that may have been created.

Following purification using KAPA beads, the resulting nucleic acid molecule was incubated with two dCas9 complexes preloaded respectively with Cas9-SEPT9.2-gRNA #1 or #2 (respectively SEQ ID NO: 10 and 11) for 1 hour at 37°

Figure 2A:
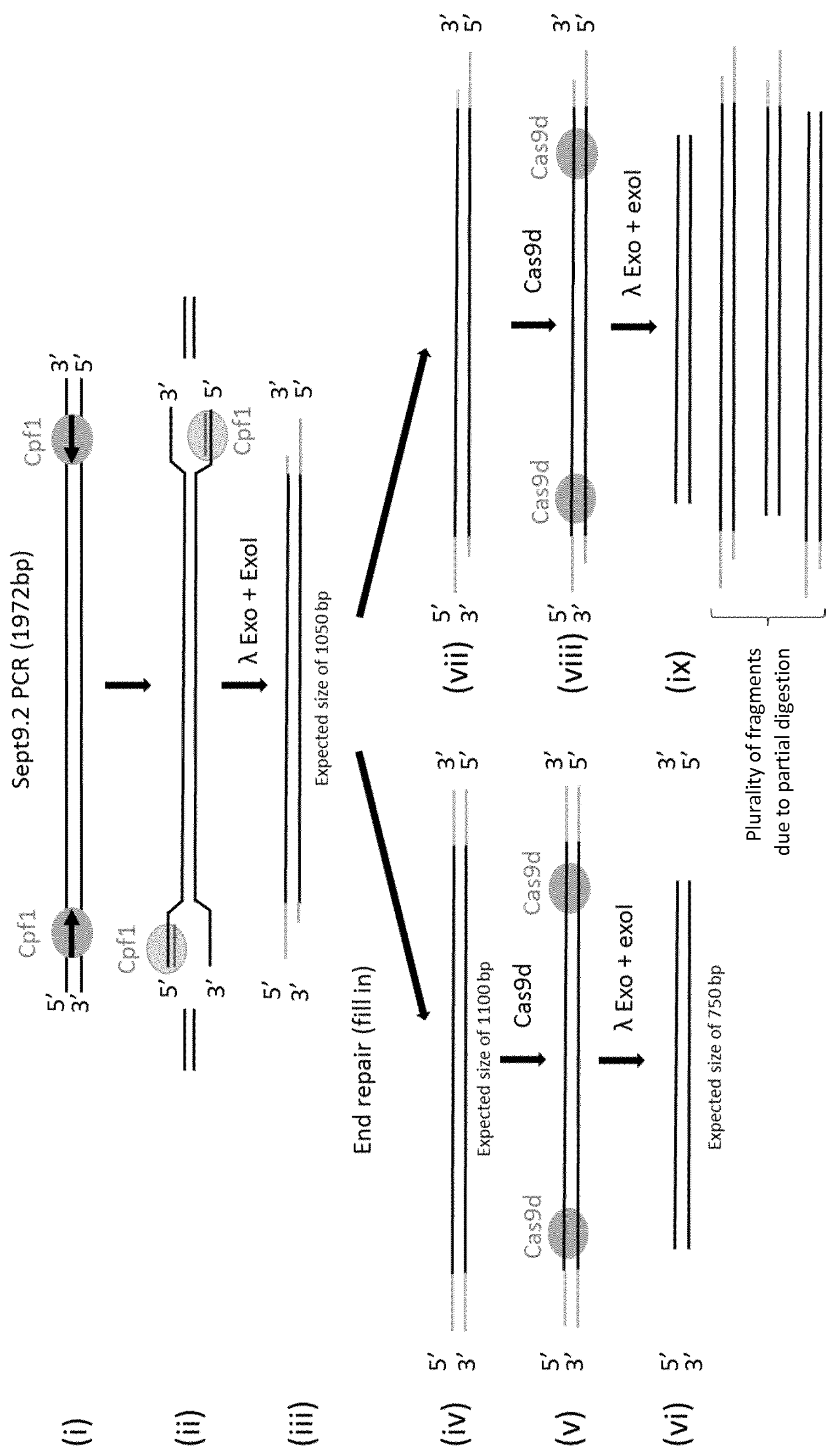
Figure 2B:
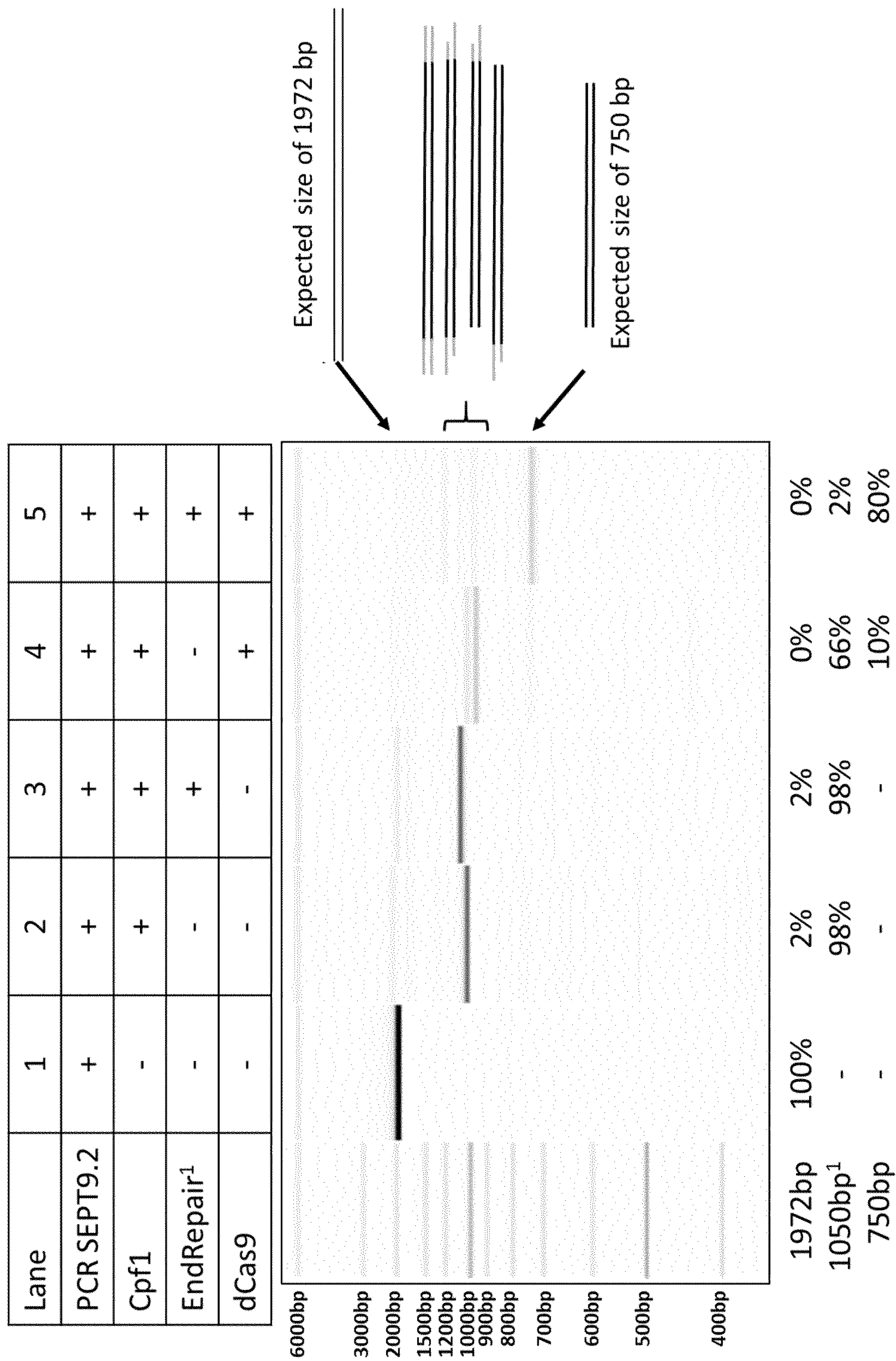

C. in the Type II reaction buffer. A cocktail of λ exonuclease and exonuclease I was added to determine if the ends of the target were a better substrate for λ exonuclease after end repair. If this is the case, the resulting 3' ssDNA is expected to be eliminated by the Exonuclease I and the length of the resulting fragment should correspond to the fragment protected by the two Cas9d-gRNA complexes (as illustrated in FIG. 2A, (vi)); said third and fourth sequences are located at the extremities of said target region). In cases where the λ exonuclease cannot initiate digestion from the one or both 5' overhangs, the length of the resulting fragments will correspond to distance between the first and second sequences bound by Cpf1-crRNA complexes or between a first (or second) sequence bound by a Cpf1-crRNA complex and a third (or fourth) sequence bound by a Cas9d-gRNA complex (as depicted in FIG. 2A, (ix)). Reactions were stopped using Stop buffer and purified using KAPA beads before running on a Fragment Analyzer® (AATI©) with the High Sensitivity NGS Fragment Analysis Kit (1 bp-6,000 bp). Advantageously, contacting the nucleic acid with a processive polymerase (end repair step) eliminated the fragments of varying sizes that were present in the absence of this step, generating uniform fragments having the expected size of 750 bp (FIG. 2B, comparison of lanes 4 and 5).

Figure 3A:
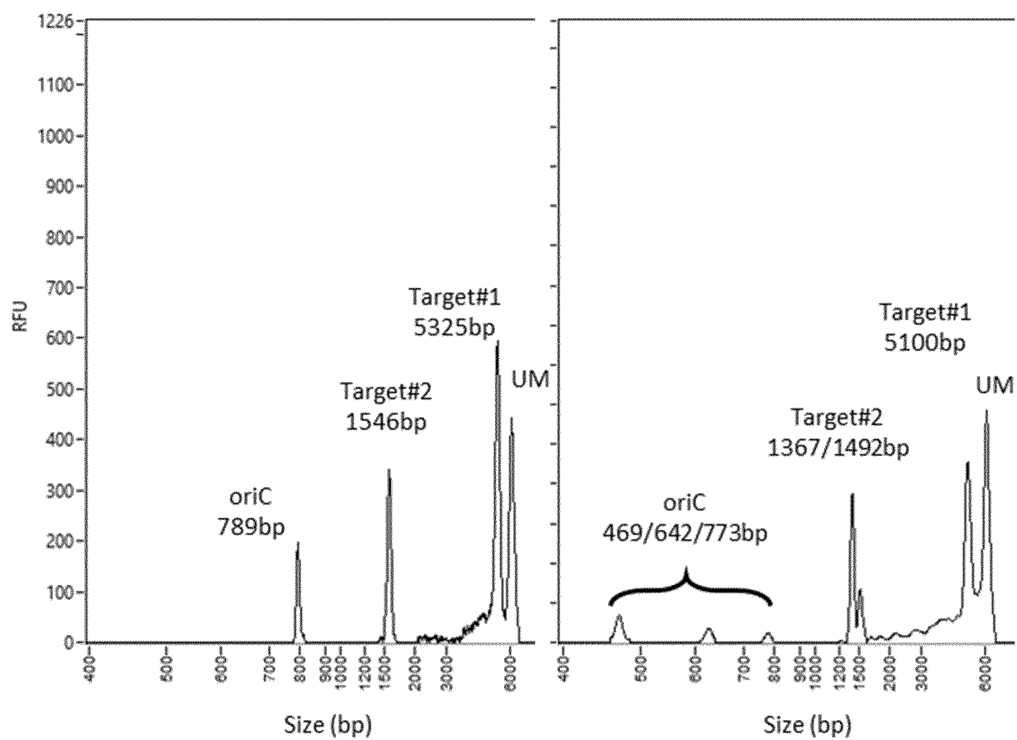
Figure 3B:
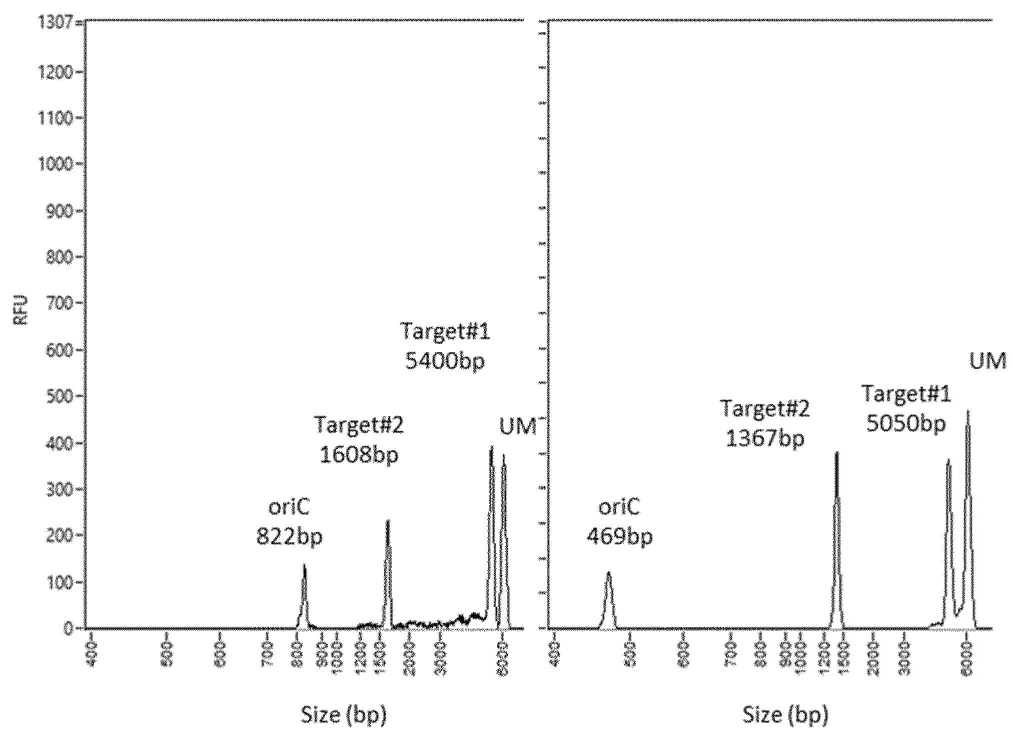

Example 4: Illustration of the General Reaction Protocols Using *E. coli* Genomic DNA Using a similar protocol as in Example 3, we evaluated the effect of repairing DNA fragment ends when using *E. coli* genomic DNA as the starting material. We designed 6 different Cpf1-crRNA complexes targeting 3 different regions (Cpf1-*E. coli* #1-crRNA #1 and #2 (SEQ ID NO: 13 and 14) for *E. coli* Target #1 (SEQ ID NO: 12), Cpf1-*E. coli* #2-crRNA #1 and #2 (SEQ ID NO: 16 and 17) for *E. coli* Target #2 (SEQ ID NO: 15) and Cpf1-oriC-crRNA #1 and #2 (SEQ ID NO: 19 and 20) for *E. coli* Target oriC (SEQ ID NO: 18)). Preloaded Cpf1-crRNA complexes were incubated with 4 μg of *E. coli* genomic DNA for 1 hour at 37° C. The reaction was then supplemented with λ exonuclease and exonuclease I to degrade unprotected DNA for 1 hour at 37° C. The reaction was stopped by adding Stop buffer and purified using KAPA Pure beads. To determine efficiency of end repair, the resulting DNA was divided into 2 tubes which were treated with the EndRepair Reaction Mix (NEB) or not. Both reactions were incubated with Cas9d complexes preloaded with Cas9-*E. coli* #1-crRNA #1 and #2 (SEQ ID NO: 21 and 22) for *E. coli* Target #1, Cas9-*E. coli* #2-crRNA #1 and #2 (SEQ ID NO: 23 and 24) for *E. coli* Target #2 or Cas9-oriC-crRNA #1 and #2 (SEQ ID NO: 25 and 26) for *E. coli* Target oriC. Reactions were incubated at 37° C. for 1 hour followed by the addition of λ exonuclease and exonuclease I. The reactions were stopped by adding Stop buffer and purified using KAPA Pure beads. Both reactions, with and without end repair, were analysed on a Fragment Analyzer® (AATI©) with the High Sensitivity NGS Fragment Analysis Kit (1 bp-6,000 bp). Results are shown in FIGS. 3A and 3B. As opposed to when end repair is not performed (FIG. 3A, right panel), only a single peak per target corresponding to the size of the fragments protected between the sequences bound by the two Cas9d-gRNA complexes, was observed when end repair was performed (FIG. 3B, right panel).

Example 5: Hairpin Construction from Isolated Target Regions

The protocol described in Example 3 was used on *E. coli* genomic DNA using Cpf1-crRNA targeting 4 different regions, Cpf1-*E. coli* #1-crRNA #1 and #2 (SEQ ID NO: 13 and 14) for the *E. coli* Target #1 (SEQ ID NO: 12), Cpf1-*E. coli* #2-crRNA #1 and #2 (SEQ ID NO: 16 and 17) for the *E. coli* Target #2 (SEQ ID NO: 15), Cpf1-oriC-crRNA #1 and #2 (SEQ ID NO: 19 and 20) for the *E. coli* Target oriC (SEQ ID NO: 18) and Cpf1-dam-crRNA #1 and #2 (SEQ ID NO: 28 and 29) for *E. coli* Target dam (SEQ ID NO: 27). Preloaded Cpf1-crRNA complex were incubated with 4 μg of *E. coli* genomic DNA for 1 hour at 37° C. The reaction was then supplemented with λ exonuclease and exonuclease I for 1 hour at 37° C. to degrade the unprotected DNA fragments. The reaction was stopped by adding stop buffer and purified using KAPA Pure beads. The purified sample was then treated with the EndRepair reaction Mix (NEB) before being purified again using KAPA Pure beads. The remaining DNA was incubated at 37° C. for 1 hour with preloaded Cas9d complexed with Cas9-*E. coli* #1-crRNA #1 and #2 (SEQ ID NO: 21 and 22) for *E. coli* Target #1, Cas9-*E. coli* #2-crRNA #1 and #2 (SEQ ID NO: 23 and 24) for *E. coli* Target #2, Cas9-oriC-crRNA #1 and #2 (SEQ ID NO: 25 and 26) for the *E. coli* Target oriC and Cas9-dam-crRNA #1 and #2 (SEQ ID NO: 30 and 31) for the *E. coli* Target dam. /\ exonuclease was then incorporated to create a 3'-ssDNA overhang on each side of the target. The reaction was stopped by adding Stop buffer and purified using KAPA Pure beads. Oligonucleotides that hybridize to the 3' single stranded overhang generated by λ exonuclease digestion are added to create a desired nucleic acid structure. As illustrated in FIG. 4, the reaction was supplemented with 3 different oligonucleotides per target region: 1) First, a 5' biotinylated oligonucleotide with a 3' end complementary to the sequence located roughly 50 bases from the PAM sequence (PS1150 for *E. coli* Target #1 (SEQ ID NO: 32), PS1219 for *E. coli* Target #2 (SEQ ID NO: 33), PS1396 for *E. coli* Target oriC (SEQ ID NO: 34) and P51395 for *E. coli* Target dam (SEQ ID NO: 35)) was added. A second set of oligonucleotides with a 3' phosphate group were then hybridized to the 3' ssDNA overhang to generate a BsaI site following its polymerization (PS1421 for *E. coli* Target #1 (SEQ ID NO: 36), PS1422 for *E. coli* Target #2 (SEQ ID NO: 37), PS1425 for *E. coli* Target oriC (SEQ ID NO: 38) and PS1423 for *E. coli* Target dam (SEQ ID NO: 39)). Finally, a third set of oligonucleotides with their 3' end complementary to the 3' single stranded overhang on the other end of the target generates a BsaI restriction site after polymerisation (PS1268 for *E. coli* Target #1 (SEQ ID NO: 42), PS1221 for *E. coli* Target #2 (SEQ ID NO: 43), PS1378 for *E. coli* Target oriC (SEQ ID NO: 44) and PS1424 for *E. coli* Target dam (SEQ ID NO: 45)).

Polymerisation was performed using the Bst full length DNA polymerase and nicks were sealed using the Taq DNA Ligase in ThermoPol Buffer (20 mM Tris-HCl, 10 mM $(NH_4)_2SO_4$, 10 mM KCl, 2 mM $MgSO_4$, 0.1% Triton® X-100) supplemented with 200 μM dNTP and 1 mM NAD, for 20 minutes at 50° C. The reaction was treated with exonuclease I for 30 minutes at 37° C. to eliminate excess oligonucleotide and purified using KAPA Pure beads. The DNA fragments were digested with BsaI to generated specific overhangs that allow the ligation of a surface specific oligonucleotides (PS1420 and PS867, SEQ ID NO: 40 and 41) to anchor the hairpin structure to a SIMDEQ flowcell and the second overhang created at the opposite end is used to ligate the loop (PS421 SEQ ID NO: 46). The resulting hairpins were purified using KAPA Pure beads and were attached on MyOne Streptavidin beads to be analysed on a SIMDEQ platform.

To successfully identify the four DNA molecules present in the sample, we used a 4 base oligonucleotide (5'-CAAG-3') which creates a specific pattern (genetic fingerprinting), as shown in FIG. 5-8, panel A. As illustrated in these figures, blockages corresponding to the 5'-CAAG-3' oligonucleotide were successfully identified.

We also successfully detected $m^5C$ base modifications present at the CCWGG motif (W can either be an A or a T) within these molecules using antibody clone ICC/IF from Diagenode as shown in FIG. 5-8, panel B. Data were generated in 3 technical replicates.

Example 6: Efficacy of Isolation is Improved when Contacting a Nucleic Acid Comprising a Target Region with a Processive Polymerase To demonstrate the increase in efficacy of isolation when the nucleic acid molecule comprising a target region is contacted with a processive polymerase in the final step of the method of preparing, we performed the same protocol with and without the end repair step and measured how many functional molecules could be observed on the SIMDEQ platform in each condition. Starting from 2 μg of *E. coli* genomic DNA, four targeted regions have been enriched using the same reagents as described in Example 5 and tested on the SIMDEQ platform. Based on the number of functional hairpins observed on our platform, the total number of potential hairpins present in the preparation after all these steps (comprising both the method of preparing nucleic acid molecules comprising target regions and the method of further isolating said target regions) was estimated. Surprisingly, the number of functional hairpins was advantageously increased by a factor of more than 10,000-fold.

Example 7: Enrichment of Target Regions from Human Genomic DNA

The protocol described in Example 3 has been used to produce enriched fragments with 3' ssDNA ends for 15 different human targets known to be either epigenetic markers implicated in cancer or composed of STR (Short-tandem repeats) known to cause disease in humans (see FIG. 10; sequences of these regions correspond to SED ID NOs: 47 to 60 and 5). Cpf1 guides RNA have been designed to hybridize to sequences flanking each target (SEQ ID NOs: 61 to 88, 8 and 9) and Cas9 guides RNA were designed within these regions protected by Cpf1 (SEQ ID NOs: 89 to 116, 10 and 11). Human genomic DNA was extracted from HEK293 cell culture. The protocol was performed on 10 μg of genomic DNA by incubation with 390 fmol of each Cpf1-crRNA complex for 1 hour at 37° C., followed by the addition of 400 U of both λ exonuclease and exonuclease I to digest any DNA that is not protected by Cpf1 complexes. The genomic DNA was incubated with all Cpf1-crRNA complexes simultaneously. The reaction was stopped by adding Stop buffer. DNA ends were repaired using NEBNext® End Repair Module for 30 minutes at room temperature and purified.

DNA prepared as described above was then incubated with all dCas9-gRNA complexes binding to third and fourth sequences of each target for 1 hour at 37° C. followed by λ exonuclease treatment to generate 3' ssDNA overhangs at both ends of the target regions. The reaction was stopped by adding Stop buffer. Oligonucleotides were designed for each isolated target region with 20 base pairs complementary to the cleavage position of Cpf1 as well as an adaptor sequence at their 5' end (SEQ ID NO: 117 to 146). These oligonucleotides were used to initiate polymerization by the Bst Full length DNA polymerase to fill-in the ssDNA overhang and the nick was sealed by the Taq DNA Ligase. Both reactions were performed simultaneously in ThermoPol Buffer supplemented with 200 μM dNTP and 1 mM NAD, for 20 minutes at 50° C. This fill in reaction was followed by an exonuclease I treatment for 30 minutes at 37° C. to eliminate excess oligonucleotides. The reaction was purified using KAPA Pure beads (Roche Life technology). The preparation was quantified using the Qubit® DNA HS Assay Kit (ThermoFisher Scientific). After enrichment, a total of 2.5 ng of DNA was recovered from the initial 10 ug of genomic DNA.

Library preparation for Illumina sequencing was performed using the Nextera XT DNA Library Preparation Kit (Illumina). The sequencing reaction was performed on a NextSeq 500 Illumina sequencer with pair-end sequencing (150 base pairs on each side). A total of 167 966 810 clusters were obtained with a quality score higher than 32, which represents 50 726 Mb of sequence. Reads were aligned using the Bowtie algorithm on the human reference genome and coverage calculation was performed using Samtools. Reads were visualized using IGV software. The representative coverage of one of the targeted regions (SEPT9.2) is shown in FIG. 11 (extract of a screenshot from IGV software).

Example 8: Enrichment of Four Different Human Targets from Clinical Samples for their Analysis on the Magnetic Tweezer Platform The protocol described in Example 3 has been used to produce four enriched fragments with 3' ssDNA ends (FMR1, C9ORF72, SEPT9.1 and SEPT9.2, SEQ ID NOs: 5, 48, 51 and 58) for analysis on the magnetic tweezer platform. For each target, two Cas9-crRNA were designed to flank the region of interest to be protected (SEQ ID NOs: 10-11, 89-90, 101-102 and 113-114) and two Cpf1-crRNA (SEQ ID NOs: 8-9, 61-62, 81-82 and 83-84) were designed at least 100 bases away from the Cas9-crRNA position. Various amounts of starting material were used, and the genomic DNA was either isolated from HEK239 cultured cells or the clinical samples NA06896 and NA07537. According to the amount of starting material, the same ratio of Cpf1 versus the DNA was used (for each molecule of DNA, 800,000 molecules of Cpf1 were added). For example, 3 pmol of Cpf1/crRNA complex in NEB2.1 buffer supplemented with 10 mM DTT was used for the first replicate of NA06896 (8.5 μg of genomic DNA (gDNA)) and incubated at 37° C. for one hour. A mixture of exonucleases was added (Lambda Exonuclease (20 U/μg of gDNA), Exonuclease I (20 U/μg of gDNA)), and the reaction was incubated for another 1 h at 37° C. Inactivation of the reaction was performed using 40 ng Proteinase K and EDTA at a final concentration of 20 nM, followed by purification using KAPA Pure beads (1×).

The ends of the resulting DNA fragments were repaired using T4 DNA polymerase (NEB) with dNTP (200 μM) in NEB 3.1 buffer (100 mM NaCl, 50 mM Tris-HCl, 10 mM $MgCl_2$, 100 μg/ml BSA, pH 7.9) to generate blunt ends. The reaction was incubated at 12° C. for 15 min before inactivation of the polymerase at 80° C. for 20 min, followed by a purification step using 0.8×KAPA Pure beads. The resulting DNA was incubated with 1.2 pmol of dCas9-gRNA complex in NEB3.1 Buffer for 1 h at 37° C. Lambda Exonuclease (15 U/μg of gDNA) was added the reaction and incubated for another 1 h at 37° C. Inactivation of the reaction was performed using 40 ng Proteinase K and EDTA at a final concentration of 20 nM, followed by a purification using KAPA Pure beads (0.8×).

The enriched fragments, which contain long 3' ssDNA overhangs at both ends, were incubated with 1 pmol of target specific biotin, surface and loop oligonucleotide (SEQ ID NOs: 147 to 158) along with 40 units of Tag DNA Ligase (Enzymatics) and 0.25 units of Full Length Bst DNA Polymerase (NEB) in ThermoPol® Reaction Buffer (20 mM Tris-HCl, 10 mM $(NH_4)_2SO_4$, 10 mM KCl, 2 mM $MgSO_4$, 0.1% Triton® X-100, pH 8.8; NEB) supplemented with 200 μM dNTPs, 1 mM $NAD^+$ at 50° C. for 30 min. Excess oligonucleotides were digested by adding 25 units of ExoI for 30 min at 37° C., followed by a purification using KAPA Pure beads (1×). The DNA fragments were digested with BsaI to generate specific overhangs that allow the ligation of surface specific oligonucleotides (PS1420 and PS867, SEQ ID NOs: 40 and 41) to anchor the hairpin structure to a SIMDEQ flowcell while the second overhang created at the opposite end is used to ligate the loop (PS189 and PS1472 SEQ ID NOs: 160 and 159).

The resulting hairpin molecules were bound on 5 μl of Dynabeads™ MyOne™ Streptavidin T1 (Invitrogen) in 1× Passivation Buffer (PB) (PBS 1×, 1 mM EDTA, 2 mg/mL BSA, 2 mg/mL Pluronic Surfactant, 0.6 mg/mL sodium azide) for 1 hour at room temperature. Beads were washed and resuspended in 1× PB prior to loading into the flow cell. Functional hairpins were identified using the 5'-CAAG-3' oligonucleotide and, for the FMR1 beads, we measured the repeat length (see FIGS. 12 and 13).

For one of the DNA samples (NA06896-Replicate 1), we also analysed the methylation status of the CpG island located within the promotor region of FMR1, which was included on the same molecule as the repeats. We measured the methylation status across the CpG and non CpG sites according to their number of repeats (see FIGS. 14 and 15). For base modification detection, the anti-$m^5C$ antibody clone ICC/IF (Diagenode) was injected at a 1/500 dilution in ABBE Buffer (20 mM Tris HCl, 150 mM NaCl, 2 mg/mL BSA, 0.6 mg/mL sodium azide).

As illustrated here, various nucleic acid fragments were successfully isolated using the method described herein. Moreover, the proposed method is highly specific as only the targeted regions were observed in our instrument. Moreover, we were able to observe the expected number of repeats in the clinical samples. Finally, because our method doesn't require any amplification, it was possible to determine the methylation status of CpG islands located within the promoter region of FMR1.

The invention claimed is:

1. A method of preparing a nucleic acid molecule comprising a target region for isolation from a sample comprising the steps of:

a) contacting a population of nucleic acid molecules with:
   - a Class 2 Type V Cas protein-gRNA complex, wherein the gRNA comprises a guide segment that is complementary to a first sequence within a nucleic acid molecule, the first sequence being located adjacent to the target region, thereby forming a Class 2 Type V Cas protein-gRNA-nucleic acid complex, and
   - a first protector molecule, to form a Class 2 Type V Cas protein-gRNA-nucleic acid complex, b) contacting the population of nucleic acid molecules containing the Class 2 Type V Cas protein-gRNA-nucleic acid complex formed in a) with at least one enzyme having exonuclease activity, thus degrading unprotected nucleic acid molecules, c) recovering the nucleic acid molecule treated with exonuclease in step b) comprising the target region from the Class 2 Type V Cas protein-gRNA-nucleic acid complex formed in step a), and d) contacting the recovered nucleic acid molecule of step c) with a processive polymerase, thus performing end repair on the nucleic acid molecule.

2. The method of claim 1, wherein the Class 2 Type V Cas protein is Cpf1 or C2c1.

3. The method of claim 1, wherein the protector molecule is a hairpin adaptor or a site-specific endonuclease selected from the group consisting of a TALEN, a zinc-finger protein, and a Class 2 Cas protein-gRNA complex, wherein the gRNA comprises a guide segment that is complementary to a second sequence within the nucleic acid molecule, the second sequence being located adjacent to the target region, wherein the first sequence and the protector molecule flank the target region.

4. The method of claim 1, wherein the at least one enzyme having exonuclease activity of step b) comprises lambda exonuclease, exonuclease I, exonuclease III, or any combination thereof.

5. The method of claim 1, wherein step c) comprises contacting the Cas protein-gRNA-nucleic acid complex with EDTA and/or at least one protease.

6. A method of isolating a nucleic acid target region comprising the steps of:

a) providing a nucleic acid molecule comprising a nucleic acid target region wherein the nucleic acid molecule has been prepared using the method of claim 1, b) contacting the nucleic acid molecule with a Class 2 Cas protein-gRNA complex, wherein the gRNA comprises a guide segment that is complementary to a third sequence, the third sequence being between the first sequence and the first protector molecule, thereby forming a Class 2 Cas protein-gRNA-nucleic acid complex, c) contacting the nucleic acid molecule with at least one enzyme having exonuclease activity, thus degrading unprotected nucleic acid molecules, and d) recovering the isolated nucleic acid target region from the Class 2 Cas protein-gRNA-nucleic acid complex.

7. The method of claim 6, wherein the Class 2 Cas protein of step a) is Cpf1 or Cas9.

8. The method of claim 6, wherein the at least one enzyme having exonuclease activity of step c) is lambda exonuclease or exonuclease III.

9. The method of claim 6, further comprising an additional step e) of hybridizing at least one single-stranded nucleic acid molecule to a single-stranded region of the target region.

10. The method of claim 9, wherein the single-stranded nucleic acid molecule hybridizes at least 50 nucleotides from the Class 2 Cas protein protospacer adjacent motif (PAM).

11. The method of claim 9, further comprising an additional step f) of extending the single-stranded nucleic acid molecule by polymerization and ligating the single-stranded nucleic acid molecule to a double-stranded nucleic acid molecule.

12. The method of claim 1, wherein the nucleic acid target region comprises a repeat region, a rearrangement, a duplication, a translocation, a deletion, or a modified base.

13. The method of claim 1, wherein at least two nucleic acid target regions are isolated.

14. The method of claim 2, wherein the Class 2 Type V Cas protein is catalytically active.

15. The method of claim 6, further comprising a step of contacting the nucleic acid molecule with a second protector molecule prior to step c).

16. The method of claim 6, wherein the second protector molecule is a Class 2 Cas protein-gRNA complex, wherein the gRNA comprises a guide segment that is complementary to a fourth sequence, thereby forming a second Class 2 Cas protein-gRNA-nucleic acid complex, the fourth sequence being between the first sequence and the first protector molecule.

17. The method of claim 16, wherein the third and fourth sequences are located at the extremities of the target region.

18. The method of claim 7, wherein the Class 2 Cas protein is catalytically inactive.

19. The method of claim 9, wherein the at least one single-stranded nucleic acid molecule comprises a label.

20. The method of claim 19, further comprising and an additional step g) of purifying the nucleic acid of step f) via the label.

* * * * *